(12) United States Patent
Whitaker

(10) Patent No.: US 12,396,554 B1
(45) Date of Patent: Aug. 26, 2025

(54) EQUIPMENT DISINFECTION CABINET

(71) Applicant: PURioLABS, LLC, Dallas, TX (US)

(72) Inventor: Mike Whitaker, Plano, TX (US)

(73) Assignee: PURioLABS, LLC, Dallas, TX (US)

( * ) Notice: Subject to any disclaimer, the term of this patent is extended or adjusted under 35 U.S.C. 154(b) by 579 days.

(21) Appl. No.: 17/693,238

(22) Filed: Mar. 11, 2022

Related U.S. Application Data

(63) Continuation-in-part of application No. 17/374,890, filed on Jul. 13, 2021.

(60) Provisional application No. 63/051,372, filed on Jul. 13, 2020.

(51) Int. Cl.
  *A47B 49/00* (2006.01)
  *A47B 57/22* (2006.01)
  *A61L 2/10* (2006.01)

(52) U.S. Cl.
  CPC ............ *A47B 49/004* (2013.01); *A47B 57/22* (2013.01); *A61L 2/10* (2013.01); *A61L 2202/122* (2013.01)

(58) Field of Classification Search
  CPC .. A61L 2202/122; A61L 2/10; A61L 2202/11; A47L 15/0076; A47L 15/4236; A47L 15/4251; A47L 15/50; A47B 57/50; A47B 57/22; A47B 49/004; A47B 63/062; A46B 17/065
  See application file for complete search history.

(56) References Cited

U.S. PATENT DOCUMENTS

| | | | | |
|---|---|---|---|---|
| 1,791,736 | A | * | 2/1931 | Mccosh ................... A47F 7/16 312/138.1 |
| 3,880,484 | A | * | 4/1975 | Sicina .................. A47B 49/004 312/197 |
| 4,100,973 | A | | 7/1978 | Freudenthal |
| 4,625,119 | A | * | 11/1986 | Murdock, III ............ A61L 2/10 250/455.11 |

(Continued)

FOREIGN PATENT DOCUMENTS

| CN | 111166902 A | 5/2020 |
|---|---|---|
| CN | 211027204 U | 7/2020 |
| CN | 211301256 U | 8/2020 |

OTHER PUBLICATIONS

Condon, "Short on PPE, facilities reuse", Washington Post, Jul. 7, 2020, Section B, p. 1.

(Continued)

*Primary Examiner* — Hiwot E Tefera
(74) *Attorney, Agent, or Firm* — Foley & Lardner LLP

(57) ABSTRACT

A disinfection or sterilization cabinet includes a cabinet frame defining an interior space, a door coupled to the cabinet frame, and an internal cabinet framework coupled to the cabinet frame and disposed within the interior space. The door is movable between a first position that substantially prevents access to the interior space and a second position that enables access to the interior space. The internal cabinet framework includes at least one bracket coupling structure. At least one bracket is removably coupled to the internal cabinet framework via the at least one bracket coupling structure. The at least one bracket includes a low contact object configured to reduce a contact area of an object supported by the at least one bracket and the at least one bracket. The cabinet includes a disinfectant or sterilization element configured to at least partially disinfect or sterilize the object.

10 Claims, 43 Drawing Sheets

(56) References Cited

U.S. PATENT DOCUMENTS

| | | | | |
|---|---|---|---|---|
| 4,740,706 | A * | 4/1988 | Murdock, III | A61L 2/10 250/455.11 |
| 5,160,699 | A * | 11/1992 | Siegal | A61L 2/10 250/455.11 |
| 5,653,349 | A * | 8/1997 | Dana | F16B 12/34 248/221.12 |
| D396,238 | S | 7/1998 | Schmitt | |
| 5,827,487 | A * | 10/1998 | Holmes | A61L 2/26 206/483 |
| D546,473 | S | 7/2007 | Xu | |
| 8,454,901 | B1 * | 6/2013 | Snyder, III | A61B 50/13 422/26 |
| 8,584,999 | B2 * | 11/2013 | Liu | G06F 1/187 248/222.12 |
| 9,162,001 | B2 | 10/2015 | Sunkara et al. | |
| 9,433,694 | B1 * | 9/2016 | Hsu | A61L 2/202 |
| 9,522,201 | B2 | 12/2016 | Sunkara et al. | |
| D822,846 | S | 7/2018 | Shimobayashi et al. | |
| D833,986 | S | 11/2018 | Vierjärvi et al. | |
| 10,675,369 | B1 | 6/2020 | Ricciardi et al. | |
| 10,716,871 | B1 | 7/2020 | Ricciardi et al. | |
| D930,181 | S | 9/2021 | Milliff | |
| 2003/0160060 | A1 * | 8/2003 | Hornblad | A47F 5/08 221/256 |
| 2006/0008400 | A1 | 1/2006 | Gutman | |
| 2006/0263275 | A1 | 11/2006 | Lobach | |
| 2007/0215780 | A1 * | 9/2007 | Eichert | A47G 1/162 248/497 |
| 2010/0266445 | A1 | 10/2010 | Campagna | |
| 2011/0305597 | A1 * | 12/2011 | Farren | A61L 2/10 422/24 |
| 2012/0153783 | A1 | 6/2012 | Shoenfeld | |
| 2013/0256560 | A1 * | 10/2013 | Yerby | A61L 2/24 250/455.11 |
| 2014/0061402 | A1 * | 3/2014 | Bernstein | A47F 5/04 248/125.3 |
| 2014/0161663 | A1 * | 6/2014 | Farren | A61L 2/10 250/492.1 |
| 2016/0008498 | A1 | 1/2016 | Boysset et al. | |
| 2017/0095071 | A1 * | 4/2017 | Osmond | A46B 17/065 |
| 2018/0030634 | A1 | 2/2018 | Doyle et al. | |
| 2018/0231176 | A1 * | 8/2018 | Sabounjian | A47F 5/0838 |
| 2018/0357886 | A1 | 12/2018 | Tavori et al. | |
| 2019/0314535 | A1 | 10/2019 | Golkowski et al. | |
| 2019/0321500 | A1 | 10/2019 | Anderson et al. | |
| 2019/0345968 | A1 * | 11/2019 | Guilfoyle | A61G 7/1078 |
| 2020/0129650 | A1 | 4/2020 | Kim et al. | |
| 2021/0299304 | A1 * | 9/2021 | Concannon | A61L 2/26 |
| 2022/0031884 | A1 * | 2/2022 | Whyte | A61L 2/26 |
| 2022/0062482 | A1 * | 3/2022 | Farrell | A61L 2/10 |
| 2022/0175998 | A1 * | 6/2022 | Vargas | A61L 2/186 |
| 2022/0265876 | A1 * | 8/2022 | Dudycha | A61L 2/10 |
| 2022/0313061 | A1 * | 10/2022 | Kim | F26B 21/04 |
| 2022/0313849 | A1 * | 10/2022 | Robinson | A47B 49/004 |

OTHER PUBLICATIONS

Steris Corporation; "Pro-Lite Sterilization Tray"; Document #10300689 (Rev A); https://ww1.steris.com/onbDocs/V433/1/928807.pdf; 2017; 2 pages.

Steris Corporation; "Sterile Processing Department: Optimize Your Investment: Pro-Lite Sterilization Trays"; Document #M9278EN. 2019-03, Rev.B; https://ww1.steris.com/onbDocs/V448/0/1864485.pdf; Mar. 2019; 2 pages.

Steris; "Pro-Lite Sterilization Trays"; https://www.steris.com/healthcare/products/v-pro-sterilizers/pro-lite-sterilization-trays; Mar. 1, 2021; 2 pages.

Steris; "SPD and OR Solutions: Driving Innovation. Delivering Throughput"; Document #M4176EN.2021.09 Rev. E; https://ww1.steris.com/onbDocs/V496/0/3762330.pdf; Sep. 2021; 5 pages.

Steris; "Sterile Processing Department: Consumables for V-Pro Low Temperature Sterilization Systems"; Document #M10425EN. 2020-01, Rev. A; https://ww1.steris.com/onbDocs/V468/0/3145489.pdf; Jan. 2020; 6 pages.

Start-Up PURioLABS Aims to Revolutionize Infection Prevention with Mobile Disinfection Cabinet, from businesswire.com, Article Date: Nov. 2, 2021, pp. 1-3, from https://www.businesswire.com/news/home/20211102005107/en/Start-Up-PURioLABS-Aims-to-Revolutionize-Infection-Prevention-with-Disinfection-Cabinet (Year: 2021).

* cited by examiner

HORIZONTAL PLANE

HORIZONTAL PLANE

Fig. 10E

| START | | |
|---|---|---|
| | UV-C | <TIME> |
| | HEAT | <TEMP>, <TIME> |
| | VAPOR | <TIME> |
| | COOL-DOWN | <TEMP>, <TIME> |
| END | | |

Fig. 10F

| SENSOR | CONDITION |
|---|---|
| TEMPERATURE | Controls the heat and cooling cycles |
| HUMIDITY | Controls the vapor, heat and cooling cycles |
| UV-C INTENSITY | Controls the UV-C cycle and bulb status monitor |
| CAROUSEL MOTION | Controls the 360 degree movement status |
| DOOR CLOSED | Controls the safety of enclosure exterior |

Fig. 10G

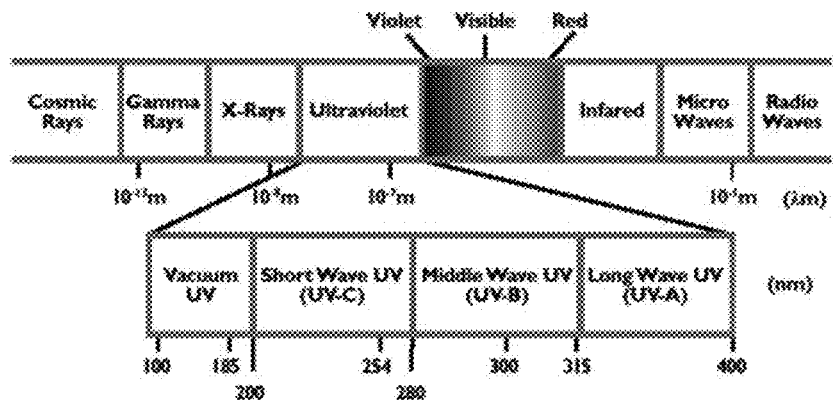

EQUIPMENT DISINFECTION CABINET

CROSS-REFERENCE TO RELATED PATENT APPLICATIONS

This application is a continuation-in-part of U.S. application Ser. No. 17/374,890, filed Jul. 13, 2021, which claims the benefit of and priority to U.S. Provisional Application No. 63/051,372, filed on Jul. 13, 2020, each of which are hereby incorporated by reference herein in their entireties.

BACKGROUND

Decontamination involves processes or treatments that render devices, instruments, or items and their surfaces safe to handle. Sterilization, disinfection, and antisepsis are all forms of decontamination. Disinfection refers to the elimination of virtually all pathogenic organisms on inanimate objects and surfaces thereby reducing the level of microbial contamination to an acceptably safe level.

The need to disinfect is arguably a more urgent part of our lifestyles today as awareness of our unseen microbial risk has become exponentially greater. Our society may carefully integrate ways to significantly reduce the risk of contaminate transmission between people, animals and objects and surfaces. Governments, institutions, schools, businesses, hospitals, clinics, remote hospitals, ships at sea, casinos, and many other unique environments need to acquire the capability to disinfect the items in use and the current art is extremely limited in the technology, practicality, flexibility and efficiency it offers. In similar historical innovations, institutions installed commercial dishwashers on site as the proven means to disinfect and sanitize eating utensils and dentists and orthodontist offices installed autoclaves on site to disinfect and sterilize dental devices/tools. Those new methods were created and adopted to address the health risks that were known at the time and became the operating standard. With the COVID-19 virus and many other possible contaminants throughout the world, the current art does not have an easily adoptable solution that can help any institution reduce the risk of transmission of potentially fatal viruses or bacteria and other contagions by an improved method for disinfection of items in use.

There is a substantial market and urgent demand for machines and methods of disinfection of many different objects and surfaces that may have come in contact with bacteria, viruses, or other contagions/diseases, collectively referred to as contaminants for this purpose. The market demand centers around the desire to prevent new exposures or additional exposures of these contaminants to people or animals or environments or objects. These contaminants have the common characteristic of being able to harm the health of those exposed. Exposure to contaminants can be fatal.

Humans and animals, when exposed to a contaminant can carry the contaminant and become a transmitter with (symptomatic) and without (a-symptomatic) personal symptoms. Transmission can occur between people or objects or surfaces without the transmitter experiencing the contaminant. Exposure to contaminants can come from unaware transmitters. When a human or animal reports symptoms of exposure to a contaminant, they often seek medical care. They are aware of an abnormality in their health yet are undiagnosed by a formal process and thus, they are a transmitter just before and during their being infected/ affected by the contaminant.

For any institutional environment wanting to achieve a lower risk of contamination, definitive measures are required. The health care setting provides the most acute example. Medical patients (human or animals) and the workers who serve them are the most at-risk for contamination due to the worker's frequency and amount of exposures and the existing patient health vulnerabilities. Medical patients enable risk of contamination by submitting to a foreign environment of unknown sterility. Medical workers enable risk to their health by reporting for work duties while also becoming the transmission mechanism patient-to-patient, room-to-room, floor-to-floor, worker-to-worker. Contaminants are invisible and highly transmittable via touch, sneeze, cough, breathing, talking, or any close contact with the contaminant that is then passed along to the next person, object, surface or environment. In any institutional setting (e.g. hospitals, clinics, schools, offices, etc.) organizations spend many billions each year to prevent health consequences of contamination as well as attempt to cure instances of contamination. Objects most commonly contaminated fall into the categories of equipment, devices, and supplies.

Preventive approaches include worker use of disposable products and materials that may come in contact with contaminants and are therefore discarded after one or few uses (e.g.: gloves, masks, face shields, face helmets, testing materials, gowns, slippers, safety glasses/goggles, and more). The current art of disposable products fails when the supply chain fails to supply the demand, leading to shortages and the need to reuse disposable products and add additional risk to workers and customers/patients. The current art does not address the need to reuse disposable items when there are supply shortages. The current art does not make it practical to disinfect and reuse disposable items when it makes sense to do so. For example, a health worker going from room to room in a hospital could reuse certain disposable items if they were disinfected between rooms, or every few hours, or at the end of a work shift, etc.

Preventive approaches include the manual wiping or spraying of surfaces and products and materials that are not disposable include periodic cleaning with user-applied disinfection method (e.g. chemical solutions). Further, preventive approaches include the training of workers on best practices to avoid spreading contaminants as well as applied cleaning methods. The contaminants that remain upon any object or surface following any disinfection effort are directly determined by the thoroughness of the human effort and machine or chemical capability. As contaminants are invisible, the probability of 100% disinfection is very low with the current art as practiced by institutions and the people or animals they serve. As an example in a medical environment, items such as testing equipment, digital thermometers, stethoscopes, blood pressure cuffs, monitoring pads/sensors, clip boards, pens, pencils, digital tablets, worker phones, safety glasses/goggles, worker shoes, durable gloves, and many more items, will come in contact with workers and patients whereby these items are potential transmitters of contaminants and current preventive manual measures are either unavailable or inadequate. In fact, when health care workers are surveyed, they report being scared to go home with their shoes, phone, and other personal effects potentially contaminated. As an example in a school or institution, items such as backpacks, phones, tablets, laptops, lunch boxes, basketballs, footballs, markers, erasers, tape dispensers, staplers, and many more common items will come in contact with workers, guests and students whereby these items are potential transmitters of contaminants and current preventive manual measures are either unavailable or inadequate.

Aside from preventive efforts, governments and institutions spend billions each year on antibiotics and anti-viral drugs administered to human and animal patients after they have been infected due to transmission. If the current art was more effective in preventing transmission, these reactionary expenses could be significantly reduced.

Practicality becomes an important factor in any effort to prevent transmission of contaminants. Since we cannot easily identify transmitters or contaminants, efforts are scrutinized for cost vs. benefit and feasibility. For example, it isn't feasible to disinfect every person, animal, the objects they carry and the clothes they wear upon entry in any doorway. If that were possible, an environment could be made 100% contaminant-free. Per above, people or animals cannot be disinfected in a practical sense. The current art can attempt to isolate if symptomatic but the environment, other people, workers, objects, devices, tools, etc. remain potential transmitters. It is not practical to manually disinfect every inch of surface of every floor, wall, object, device, machine, test material, button, etc. every time it is touched. Because of impracticality of the above, every worker, their equipment, surfaces, objects, devices and anything that could have made contact with a transmitter or contaminant is suspect-which is the primary reason for fear that drives the market demand.

There are many methods that can be used to disinfect objects and surfaces, but the current art has severe limitations. Contaminants can include viruses, bacteria and all contagions. There are many ways to "kill" each of these when encountered on a surface or embedded in material. One proven disinfection method includes the use of ultraviolet light in the "C" classification, UV-C, which operates at light wavelengths 200-280 nm (See FIG. 10G). There are handheld UV-C emitting devices on the market. One handheld product requires a user can use a wand to flash-disinfect a surface. Uneven and inadequate and incomplete exposure to UV-C rays is probable with this type of device. UV-C is a known carcinogen for skin and can damage corneas among other sensitive tissues. For any hand-held solution, the operator is responsible to assure 100% exposure to the needed surface for disinfection and requires the operator to assure the needed exposure time for every amount of surface area, calculated in the art as:

$$UV \text{ dose } \mu Ws/cm^2 = UV \text{ intensity } \mu W/cm^2 \times \text{exposure time (seconds)}$$

Thus, the proper disinfection "dose" of UV-C light is dependent upon the UV-C light intensity, distance, and exposure time, whereby distance and time are subjective to the user and highly likely to be rushed or skipped as there is no way to see or measure disinfection progress/success (e.g. imagine mowing a lawn and not seeing the cut grass). Also, any blockage of light-of-sight exposure leaves areas unexposed and therefore untreated by this disinfection method.

There are disinfection boxes available on the market whereby consumer users can place their phone, keys, wallet or other small objects inside the container and a dose of UV-C light is introduced. While this box keeps harmful light from reaching outside, objects are placed atop surfaces that fully or partially occlude the light from reaching the objects. The box cannot achieve equal light-of-sight exposure or even assure any light-of-sight exposure based upon the placement of the objects in the container. Adequate exposure is suspect. Timing for what is adequate for the objects and their position within the box to achieve the proper dose is also suspect. Also, these boxes are designed for small objects and their overall design is one for consumer use of personal, small items with extended exposure times required. In general, for containment boxes offering to disinfect objects, there is a high risk of recontamination if the same door and edge outside surfaces are touched after a disinfection effort has been completed on the inside (i.e., "going out thru the in door"). Someone's hand opened the door when contents are suspect and that same hand will open the door to unload disinfected items. The single door approach requires incredible discipline to overcome the recontamination risk.

Another method in the current art involves a large container with a series of holding clips (e.g. the clothesline) strung across many strings or wires and UV-C light bulbs alongside the container walls whereby user(s) can enter the container to attach various items to be disinfected (devices, supplies, masks, shields, gloves, gowns, coats) and then close the container and turn on the UV-C light for 30-180 minutes or more. The limitations to this method are many: The container is too large and heavy to be brought into a normal interior working environment. Contaminated materials/objects may be transported through clean environments to reach the container, exposing additional rooms, floors, HVAC systems, and people to contamination. Items are hung in a way to create uncertain light-of-sight exposure, clips can cover contaminated areas of each item, and the same doors are used to get access to disinfected items as were used to load contaminated items. Additionally, a small "load" is impractical or requires more volume to justify a disinfection cycle due to the size of container or duration of the treatment.

Generally, all forms of the current art for using UV-C light as a disinfection method have the items to be disinfected and the UV-C light bulbs in fixed positions, assuring blind spots for line-of-sight exposure, uneven light dosage, and higher required duration to overcome the above weaknesses, with added sensibility dependency on operators who may not understand how a proper dose of UV-C is administered based upon intensity and distance and time. Additionally, the current art fails to position the items to be disinfected by UV-C light in a manner that exposes all surfaces, leaving pockets of unreachable potential contamination. Also, the current art of using UV-C light as a disinfection method is ineffective upon contaminant bodies that are clumped or intertwined within layers or fibers just underneath the surface.

Another available method of disinfection is to expose the contaminates to high heat, varying levels of humidity, and air flow. High temperatures above 140 degrees Fahrenheit degrade and kill bacteria, viruses and other known pathogens. The current art does not have a practical way of heating surfaces and spaces to achieve disinfection from a portability and containment standpoint. From research, scientists have proven that higher temperatures can destroy living contaminants. Additive to heat is the variable, humidity. Again from research, it is known that high humidity and low humidity have enhanced disinfection effectiveness of living contaminants when combined with high heat. Also from research, it is known that positive air flow (vs. a vacuum) has enhanced disinfection effectiveness upon living contaminants.

Yet another current method of disinfecting items like facemasks or other higher risk items is to contain the items inside large containers and expose them for several hours to vaporized hydrogen peroxide or chlorine-based sanitizing solutions. Liquid compounds when vaporized can reach all exposed surfaces. This approach fails in several ways, including the following. The condensed liquid creates dripping residue from one item to another (following gravity) so that one person's mask residue (for example) drips onto another's. Contaminated items may be transported from a clean space, through clean spaces, to be loaded into a contaminated space. The same doors are used to load contaminated items and their exterior is not disinfected to any known certainty when items are unloaded. The process takes hours to complete and can leave the items moist. User error can result in items stacked to closely to prevent adequate exposure to this disinfection method.

Considering the above described current art of UV-C light exposure, heat and air exposure, and vaporized liquid exposure, each of these approaches fail for certain materials within the items to be disinfected. Not all materials can receive UV-C light, not all materials can withstand high heat, and not all materials can be exposed to hydrogen peroxide, chlorine or many other chemicals that may be used in solution.

The current industry is constantly looking for cheaper, practical, flexible, effective, and portable disinfection products and methods as well as methods and systems for implementation, operating, maintaining, and distribution to the consuming public. Thus, there is a need for a new and improved disinfection product, system, and method of disinfection and general use as disclosed herein.

SUMMARY

One exemplary embodiment relates to a disinfection or sterilization cabinet includes a cabinet frame defining an interior cabinet space, at least one door coupled to the cabinet frame, and an internal cabinet framework coupled to the cabinet frame and disposed within the interior cabinet space. At least one door is movable between a first position that substantially prevents access to the interior cabinet space and a second position spaced apart from the cabinet frame that enables access to the interior cabinet space. The internal cabinet framework includes at least one bracket coupling structure. At least one bracket is removably coupled to the internal cabinet framework via the at least one bracket coupling structure. At least one bracket includes a low contact surface object configured to reduce the contact area of an object supported by at least one bracket. The cabinet includes at least one disinfectant or sterilization element configured to at least partially disinfect or sterilize the object supported by at least one bracket.

Another exemplary embodiment relates to an interior framework for a disinfectant or sterilization cabinet. The interior framework includes a central structure comprising a central shaft, the central structure configured to rotate about a central axis within the disinfectant or sterilization cabinet and an outer structure coupled with the central structure and configured to rotate with the central structure. The central shaft is removably coupled with the central structure. The outer structure includes a plurality of bracket attachment points configured to couple with one or more brackets. The one or more brackets are configured to support an object such that the object rotates with the central structure.

Another exemplary embodiment relates to a bracket for supporting an object within a disinfection or sterilization cabinet. The bracket includes a bracket base defining a first opening and a second opening. The first opening is configured to receive a protrusion of an interior framework of the disinfection or sterilization cabinet. The second opening is configured to detachably receive a bracket attachment. The bracket attachment includes one or more low-contact features configured to fit a specific type of object while also reducing the contact area of the object supported by at least one bracket coupled with the interior framework within the disinfection or sterilization cabinet.

The present disclosure relates to medical and personal protective equipment disinfection systems and methods. More particularly, the disclosure relates to a new and improved item disinfection cabinet and method, method for making, distributing, using, and system thereof. Rendering various living contaminants such as viruses and bacteria inert to prevent transmission to other objects and people involves applying a disinfection method to an item. Prior art cases involve a single disinfection method unevenly applied to each item in costly, time-consuming and impractical manners with unknown effectiveness. The disclosed cabinet provides an affordable, convenient, and flexible disinfection method and result. The cabinet includes a portable industrial-grade sealed enclosure for the loading of items needing disinfection with one or more access doors whereby multiple and different disinfection methods are available sequentially or concurrently in a disinfection treatment plan that is selected for its effectiveness per the items and their materials and the targeted contaminants. All disinfection methods are more effective due to the movement between item and disinfection source. Items are presented for treatment via time-saving, quick-change mounting brackets designed purposely to secure and present each item type uniquely. The cabinet enables a room partition separation discipline for "dirty" vs. "clean" item loading and unloading through separate access doors. The cabinet uses computer controlled hardware and software to operate, monitor and set testing and treatment cycles. As such, the general purpose is to provide a new and improved disinfection device and method which has all the advantages of the prior art and none of the disadvantages.

A disinfection treatment plan prescription can be based upon [contaminant×materials×disinfection method×duration].

The current art lacks a comprehensive yet fitting approach to matching the disinfection treatment plan to the items requiring disinfection.

The current art fails to be portable in its use. Requirements of the art include that industrial/institutional disinfection containers may be outside, lifted by forklifts, contaminated products may be transported through clean areas to reach the disinfection location, etc. The disinfection capability of the current art is incapable of being located nearest the sources of contamination to avoid spread of contaminants as well as being operationally practical.

The current art fails to be easily accessible for loading and unloading by the operator whereby operators may physically enter a container to arrange items or may work around hardware, racks, shelves, doors, wires and more to place or remove items. This limitation places significant bending, reaching, and other movements that can create injury over time or are movements not possible for aged or small or large persons.

The current art fails to leave the environment inert following vapor treatments whereby users are cautioned when the enclosure is opened that residue can remain that is hazardous to operators or item users. Additionally, the current art involves external evacuation of air/vapor or open door "airing out" of the enclosure to render the items and enclosure air inert to humans or animals. These provisions are further inflexibility, danger, and cost to the institution.

The current art fails to be time-efficient in its use. Waiting an hour or hours for a process to complete requires significant extra inventory of the items to be disinfected. Waiting until a container is full to run a "cycle" creates unnecessary wait time or requires excess inventory. Transporting disinfected items from a disinfection site to the area of use is time-consuming and laborious.

The current art fails to be affordable in its use. During the COVID-19 epidemic alone, governments and institutions have spent hundreds of millions of dollars on 3rd party sterilization services using the above approaches to disinfection, with expenses as high as $7 per mask disinfection. Affordability is possible when the government or institution can self-administer item disinfection on-demand in a controlled manner.

The current art lacks availability for a disinfection solution for common objects that come in contact with contaminants. A school, business, or institution desiring to have a disinfection capability cannot find affordable assets to purchase so that they have such capability in convenient locations when they need it at an operating complexity they can execute with confidence.

The current art lacks a comprehensive approach to matching the disinfection treatment plan to the items requiring disinfection.

The current art lacks the ability to combine two or more disinfection methods in a manner that customizes a disinfection treatment plan (based upon items to be treated or contaminants targeted).

The current art lacks the ability to provide a multi-method attack upon contaminants within the same treatment cycle whereby thoroughness is enhanced by employing multiple disinfection methods simultaneously or in a series within the same cycle.

The current art lacks robustness and discipline whereby the user does not have pre-configured treatment plan options or software controls that are of known efficacy for the varied items and materials and circumstances encountered by the government or institution. Rather, the current art requires the user to manage key aspects of technologies and treatments as a pseudo-expert to assure treatment efficacy without the assistance of technology controls that operate and communicate system and cycle status.

The current art lacks the ability to be a closed system whereby the air and vapor generated for disinfection purposes and fluids can be rendered inert and of nominal impact to operator or item users immediately following treatment. Rather, existing systems require exhausted air, heat, vapor to outdoors which is at either great expense to modify buildings or at great inconvenience as disinfection may be performed outside the normal workspace for the institution.

A disinfection cabinet includes: a transportable cabinet frame having a horizontally disposed base, at least one vertically disposed bounding wall, a horizontally disposed top; at least one rotating framework for holding and presenting items for disinfection within the cabinet, the rotating framework configured to rotate about a vertical axis and having plural attachment points; at least two different types of item holders configured for attachment to the attachment points, each of the two different types of item holders configured for holding a different type of item to be disinfected; and at least one disinfecting light source positioned within the cabinet.

The cabinet can further include: at least one heat source configured to heat the interior of the cabinet; and at least one vapor delivery source configured to deliver a disinfecting vapor within the cabinet. The vapor delivery source can be configured to regulate humidity and chemical saturation level within the cabinet.

The cabinet can further include: at least two access doors mounted to the cabinet frame and providing access to an interior of the cabinet through two separate access door openings, wherein each of the access door openings is positioned on an opposite side of the cabinet frame. The cabinet can further include: at least one means for circulating air in the interior of the cabinet. An air source can be configured to provide a supply of air to or remove air from the interior of the cabinet.

The cabinet can further include: a control system configured to control and regulate application of multiple disinfection methods in accordance with a customizable treatment plan. The customizable treatment plan can be based upon the type or composition of items to be disinfected.

The cabinet can further include: for at least one of the at least one framework, at least one guide feature extending vertically for at least a majority of a height of the framework, the guide feature extending along a parallel to an axis of rotation of the framework so as to nudge items on the rotating carousel into intended positions within a predefined circumference around the axis of rotation as the framework rotates. The framework can include one or more vertically disposed outer members having the one or more attachment points, and wherein at least one item holder attached to one of vertically disposed outer members is positioned with a centerline that is angled between an intersection of a first plane tangent to a circumference of rotation of the vertically disposed outer member and a second plane extending along the axis of rotation of the framework as well as the vertically disposed outer member.

The cabinet can further include: a drive mechanism configured to rotate the rotating framework, wherein the drive mechanism is configured to permit slippage of rotation of the framework in case of blockage or manual movement of the framework during loading or unloading.

A method for disinfecting items includes: opening a first access door providing internal access to a transportable disinfection cabinet through a first opening in the cabinet; loading through the first opening a batch of different items onto at least two different types of item holders, each of the two different types of item holders configured for holding a different type of item to be disinfected, each of the items holders being attached to an attachment point on a rotating framework within the cabinet; closing the first access door after loading the batch of items; causing the cabinet to perform a disinfection process on contents of the cabinet, wherein the disinfection process includes: rotating the framework on a vertical axis of rotation within an interior of the cabinet, and exposing the items to a disinfecting light source positioned within the cabinet; in response to an indication from the cabinet that the disinfection process is complete, opening a second access door providing internal access to the cabinet through a second opening in the cabinet positioned on an opposite side of the cabinet from the first opening; and removing the batch of items from the framework through the second opening.

The disinfection process can further include: exposing the items to air movement and circulation within the cabinet, operating a heat source configured to heat the interior of the cabinet, and operating a vapor delivery source configured to deliver a disinfecting vapor to the interior of the cabinet. The disinfecting vapor can include water vapor, wherein the water vapor raises a humidity level in the cabinet.

The disinfection process can be driven by a control system configured to control and regulate application of multiple disinfection mechanisms in accordance with a customizable treatment plan. The control system can be configured to receive data from one or more sensors within the cabinet to sense: motion of items within the cabinet, and operation of one or more disinfection methods, wherein the control system is configured to control the treatment plan in response to data received from the one or more sensors. The customizable treatment plan can be based upon the type or composition of items to be disinfected.

The method can further include: at least one guide feature of the cabinet nudging items on the rotating carousel into intended positions within a predefined circumference around the axis of rotation as the framework rotates.

The framework can include one or more vertically disposed outer members having the attachment points, and wherein at least one item holder attached to one of vertically disposed outer members is positioned with a centerline that is angled between an intersection of a first plane tangent to a circumference of rotation of the vertically disposed outer member and a second plane extending along the axis of rotation of the framework as well as the vertically disposed outer member. The items can include personal protective equipment.

The invention is capable of other embodiments and of being carried out in various ways. Numerous specific details are provided to impart a thorough understanding of embodiments of the subject matter of the present disclosure. The described features of the subject matter of the present disclosure may be combined in any suitable manner in one or more embodiments and/or implementations. In this regard, one or more features of an aspect of the invention may be combined with one or more features of a different aspect of the invention. Moreover, additional features may be recognized in certain embodiments and/or implementations that may not be present in all embodiments or implementations.

BRIEF DESCRIPTION OF THE FIGURES

The disclosure will become more fully understood from the following detailed description, taken in conjunction with the accompanying figures, wherein like reference numerals refer to like elements, in which:

FIG. 10E illustrates pre-set or variable treatment plans that are a combination of disinfection methods, either in serial or overlapping order, with adjusted thresholds and duration FIG. 10F illustrates use of sensors to assure the needed environmental factors are reached and maintained to assure treatment efficacy and operator safety.

FIG. 10G illustrates the range of UV light in the electromagnetic spectrum.

DETAILED DESCRIPTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

In the following description, references are made to various embodiments in accordance with which the disclosed subject matter can be practiced. Some embodiments may be described using the expressions one/an/another embodiment or the like, multiple instances of which do not necessarily refer to the same embodiment. Particular features, structures or characteristics associated with such instances can be combined in any suitable manner in various embodiments unless otherwise noted. By way of example, this disclosure may set out a set or list of a number of options or possibilities for an embodiment, and in such case, this disclosure specifically contemplates all clearly feasible combinations and/or permutations of items in the set or list.

Figure 1:
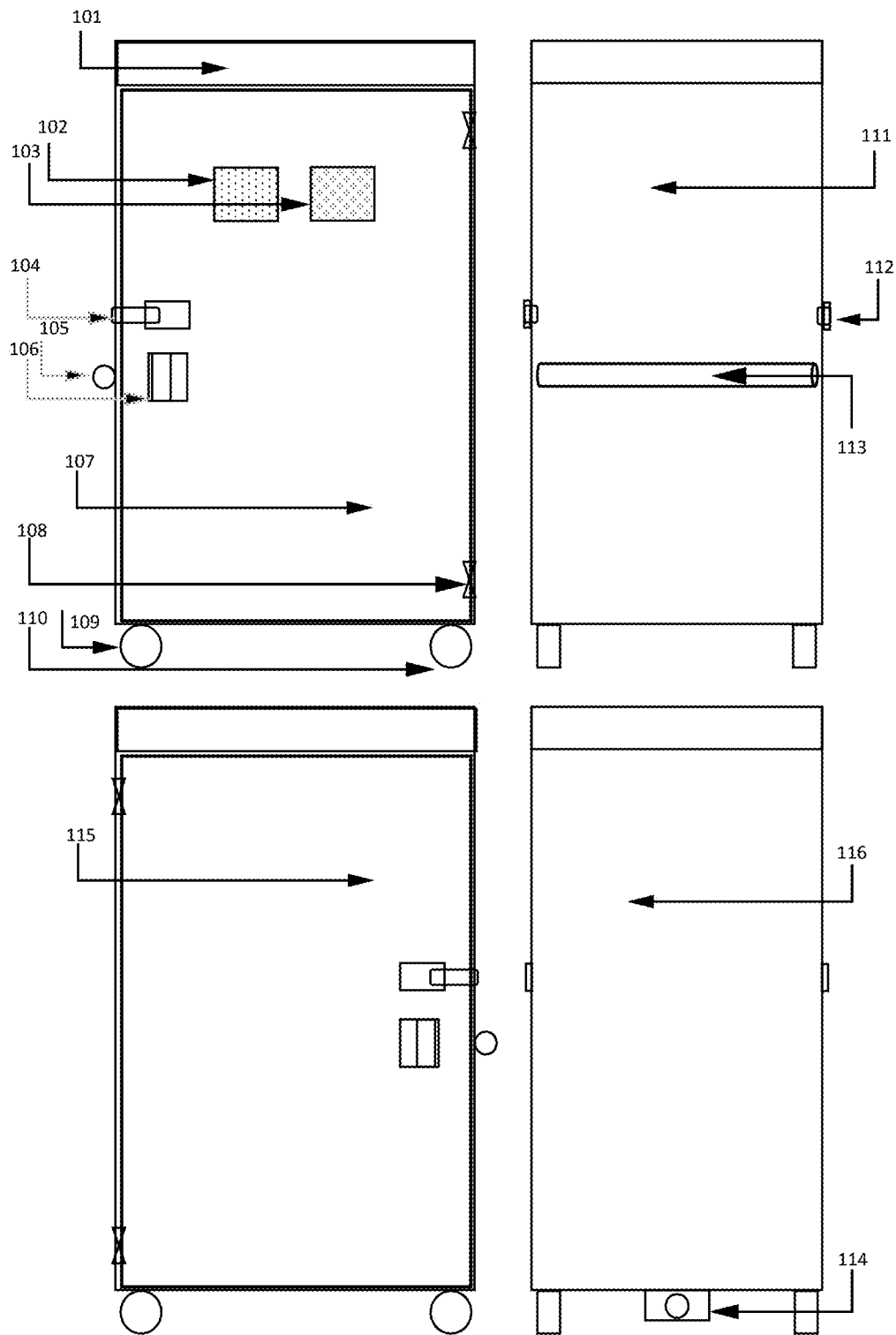
FIG. 1 illustrates a high perspective view of the external surfaces and working components and important features of the cabinet.

FIG. 1 illustrates a view of the external surfaces and working components and important features of a disinfection cabinet. The cabinet contains all electronics and drive and pump and actuating components in the area 101, which can be separate from the interior of the cabinet to protect possible sensitive components from the harshness of disinfection methods, whereby access to area 101 can be via a separate access door from above. For the same purposes, area 101 could be located on any other side of the cabinet. A right side access door 107 the cabinet can include a see-through safety window 102 and operator control panel/screen 103. Alternatively, a see-through window 102 could be located on any surface of the cabinet and operator control panel/screen 103 could be located on any surface of the cabinet. Security latch 104, 112 that applies locked and sealed pressure to the door enclosure can be centrally located along the vertical dimension. One or more security latches can be used for the same purposes. Each access door offers a pull-handle 106, located centrally on the vertical dimension. One or more door handles can be used for door opening. Door hinge 108 allows the door to swing open and contains the wiring necessary for door components whereby the threaded wiring between cabinet and door is not visible to the operator when door is open or closed. One or more door hinges could be utilized in other locations for one or more access doors. For portability ease, the cabinet can incorporate a push/pull handlebar 105, 113 and swivel wheels 109 and fixed wheels 110 to allow a single person to easily maneuver the cabinet and steer from the handle side 111 of the cabinet. Alternatively, one or more handles can be used to grip and maneuver the cabinet and can be located elsewhere on the cabinet exterior. A left side access door 115 can feature components common to the right side access door. The wall-side of the cabinet 116 can be designed to be placed against a wall to allow for a natural separation between operating sides and openings. The cabinet can be configured to have no protruding cords or parts that can catch during transport or operation and power inlet 114 is ready to accept a common 120v power connection and is located where any connected power cord will not interfere with operator movement or create a tripping hazard.

Figure 2:
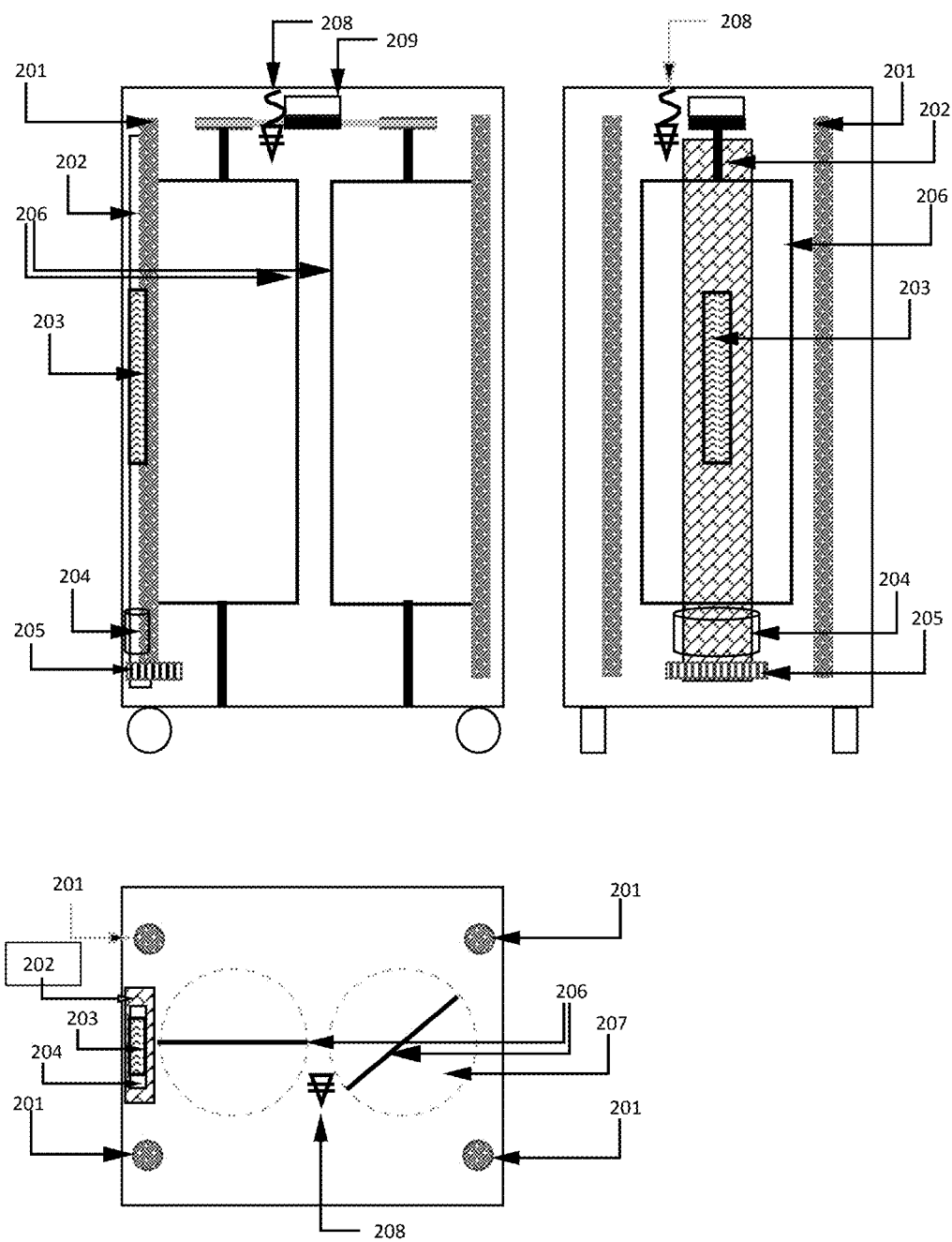
FIG. 2 illustrates a high perspective view of the internal space and working components and item movement and light circulation of the cabinet, including the item movement multi-exposure embodiment.

FIG. 2 illustrates a view of the interior surfaces, working components and important features of the cabinet. Disinfection Method 1 (light) can be positioned in a manner that provides multi-bulb and multi-angle access 201. Disinfection Method 2 (heat) can be delivered from heating element 203 and transported by air duct 202. Disinfection Method 3 (air) can be propelled by a fan or blower 204 providing a means for moving air, pushing or pulling air within the enclosure. The fan or blower 204 can move air through a HEPA filter 205 located either interior or exterior of the cabinet. The fan or blower can be located either interior or exterior of the cabinet. Disinfection Method 4 (vapor) can be delivered from a fogging release unit 208 and dispersed throughout the interior via circulating air propelled by fan or blower 204. The delivered vapor can include, for example, hydrogen peroxide, water, solvent, drying agent, fragrance, or a combination thereof. The fogging release unit 208, accordingly can be used to increase the humidity within the cabinet to a desired or target level for disinfection purposes.

The above multiple disinfection methods are part of the simultaneous and serial multi-disinfection method embodiment. The application of the above disinfection methods upon items contained in the cabinet during a treatment cycle has those items transported on or within a framework 206, the item movement multi-exposure embodiment, as one or more frames move on their center points in the complete 360° carrousel movement area 207, driven by power movement 209, providing uniform treatment application. Alternatively, the item could be stationary and the disinfection method can be moved around the item to accomplish the above embodiment. Alternatively, the item can be moved upon a conveyor or carriage for presentation to various disinfection methods. Alternatively, the movement of items can achieve a partial or full exposure of the item as the direction and total movement of the item can be different than above. In the item movement multi-exposure embodiment, due to increased exposure of all facets of an item to various treatments the efficacy of all disinfection methods is enhanced and the time required to achieve a disinfected state is lowered respectively. One embodiment provides a new and improved item disinfection system and method which provides maximum possible item exposure to all disinfection methods and treatments by changing the position between item and disinfection method whereby simultaneous exposure is possible to each item, on all facets/sides of the item (see FIGS. 10A-D).

Figure 3:
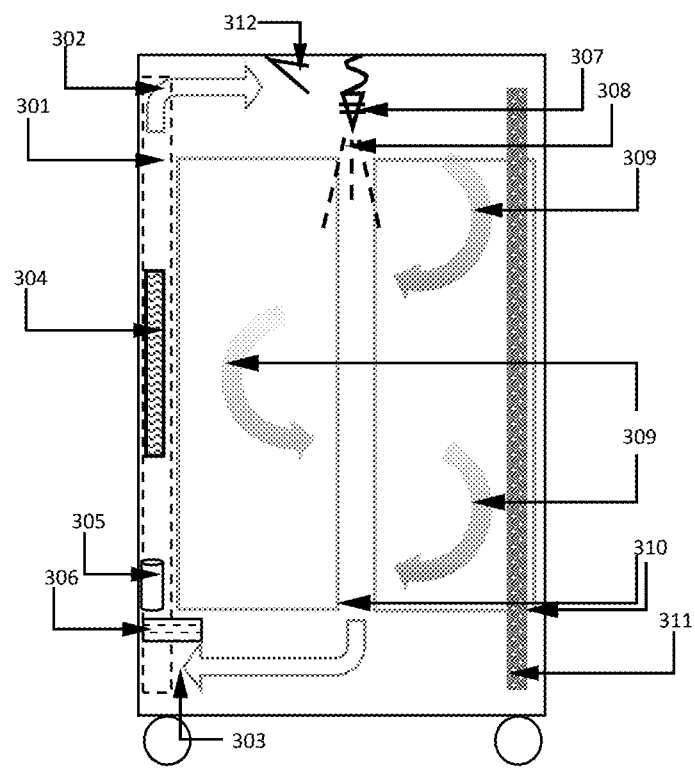
FIG. 3 illustrates a high perspective view of the internal space and the light, air, heat and vapor circulation throughout the cabinet as part of the simultaneous and serial multi-disinfection method embodiment.

FIG. 3 illustrates the simultaneous and serial multi-disinfection method embodiment whereby internal space and the air, heat and vapor circulation throughout the cabinet as air enters the duct 301 at location 303, travels through the air filter 306, through the fan or blower assembly 305, through heating element 304, and exits duct 301 at location 302, and is exposed to one or more light sources 311. Disinfection Method 1 (light 311), Disinfection Method 2 (heat 304), Disinfection Method 3 (air 305) and Disinfection Method 4 (vapor 307, 308) are effective due to enveloping all interior cabinet air and exposed surfaces and materials of items contained in the cabinet during a treatment cycle as the air flow is circulated and tumbled 309 from top to bottom of cabinet as item presentation framework in the form of a carrousel 310 moves the items within the treatment area. Air flow can be guided for balance and best distribution of vapor and air using the air flow guide 312 to selectively deflect portions of the air flow in different directions within the enclosure. The simultaneous and serial multi-disinfection method embodiment can offer two or more disinfection methods that can include ultra-violet light, heating, cooling, air pressure, air movement, and vaporized liquids with or without chemical components, laser light, and more-all of which can be customized as part of any treatment plan based upon the items and materials to be disinfected. The amount, level, intensity, saturation, duration of any disinfection method is adjustable as needed for maximum efficacy of any treatment of any item. The above embodiments can achieve a closed system of air and item movement whereby no air is added or subtracted from the enclosure and requiring no external vents outside the enclosure. Alternatively, the above embodiments can be operated similarly if the fan or blower 204 is moving air sourced from outside the enclosure into the enclosure and moving the air in the enclosure outside the enclosure.

One embodiment provides a new and improved item disinfection system and method which can combine two or more disinfection methods in a manner that customizes a disinfection treatment plan (based upon items to be treated or contaminants targeted) and executes that plan via controls of the hardware. The objective involves a multi-method attack upon contaminants within the same treatment cycle whereby thoroughness is enhanced by employing multiple disinfection methods simultaneously or in a series within the same cycle. For example, sensitive electronic devices may be treated with UV-C and Heat but no Vapor. In another example, sensitive plastic materials may be treated with UV-C and Vapor but no Heat. Additionally, the duration of any disinfection method is part of customized disinfection treatment plan. For example, some materials cannot tolerate long UV-C exposure and so the duration of UV-C can be shortened and other disinfection methods extended.

Figure 4:
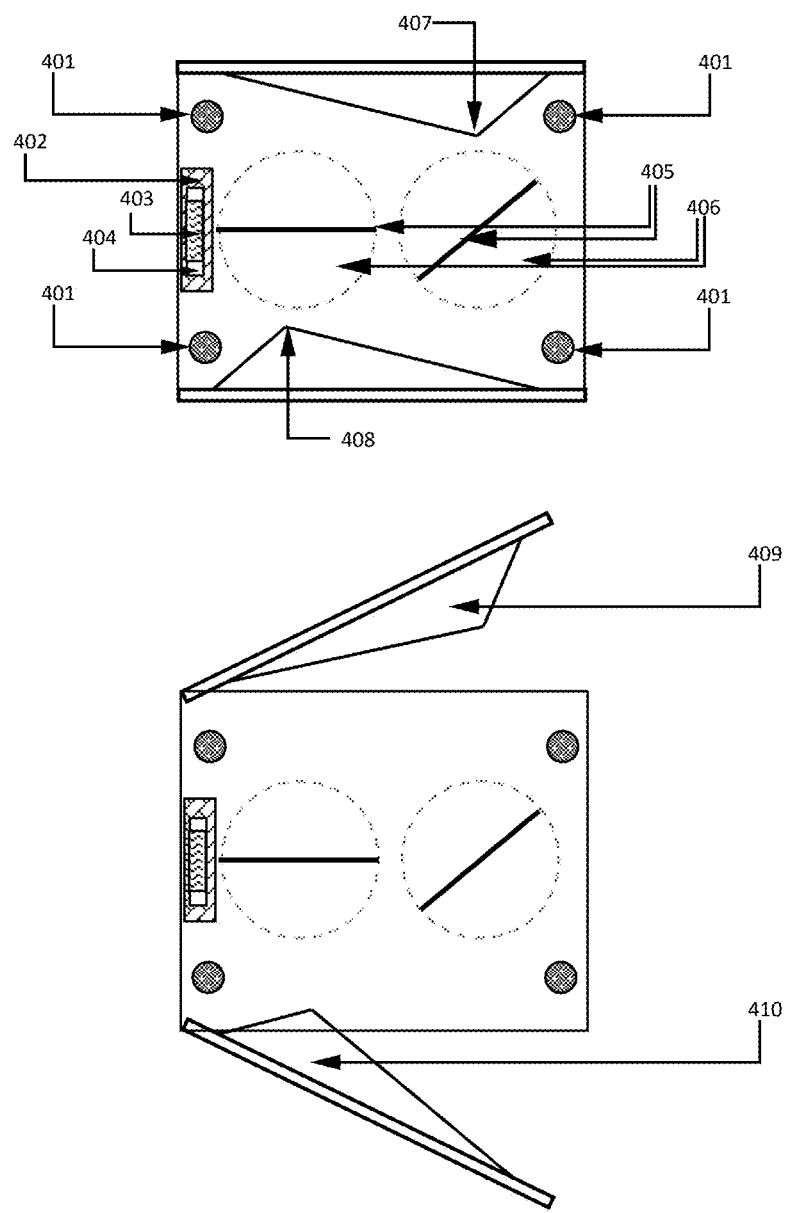
FIG. 4 illustrates a high perspective view of the internal space and the cabinet's item physical guide embodiment and interior space saving embodiment.

FIG. 4 illustrates the cabinet's internal space using item physical guides to save interior space in accordance with one embodiment. As the framework carrousels 405 move at their center point 360° within carrousel movement area 406, items contained within the carrousel could potentially shift whereby all or a portion of any item could extend beyond the carrousel movement area 406 and if so, item physical guide point 407, 408 is positioned to nudge the item toward carrousel movement area 406 and preventing the item from leaving the carrousel movement area 406 where the item would be prevented from receiving or would prevent other items from receiving full treatment by chosen disinfection methods. The triangular form 409, 410 on the interior of the cabinet provides the physical guide points 407, 408 and the triangular form 409, 410 occupies significant interior area that would otherwise be open and require more disinfection efforts if triangular forms 409, 410 did not exist. Physical guide points could protrude from another interior surface of the cabinet to correct the position of any item as a means to the item physical guide embodiment. Interior panels could protrude from one or more surfaces to occupy space as a means to the interior space saving embodiment. The item physical guides provide a new and improved item disinfection system and method which has built-in physical guide material on the interior of the enclosure or door assembly whereby any item that becomes misaligned with its intended position as it rotates is nudged toward its original intended position so that it remains in place for exposure as well as it does not affect any other item or the cabinet's mechanisms. Alternatively, the item can be moved upon a conveyor or carriage and a similar physical guide can be positioned to assure the item remains in its intended position throughout the treatment cycle.

Figure 5:
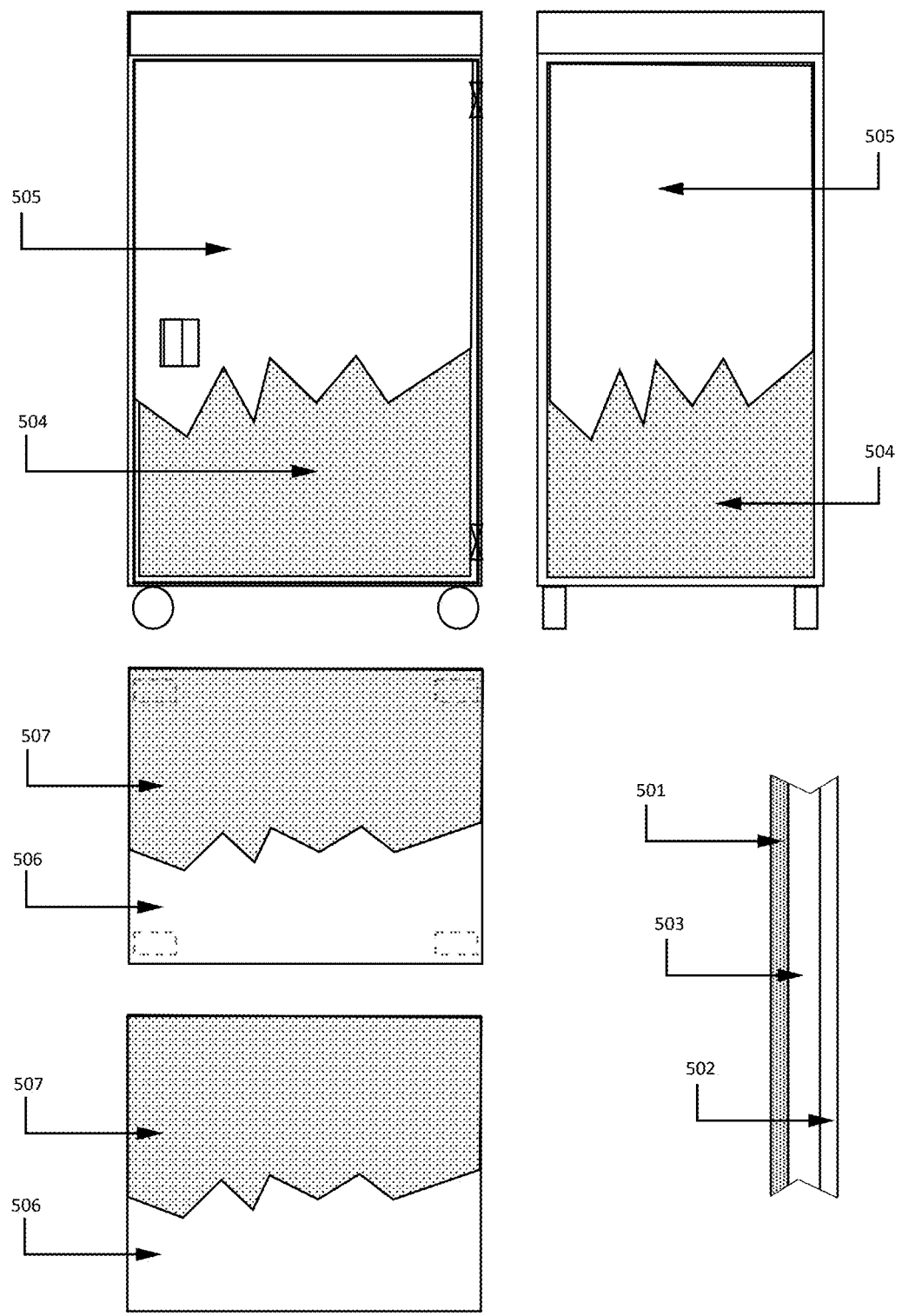
FIG. 5 illustrates a high perspective view of the cabinet's multi-layered frame whereby all facets of the cabinet have at least two layers and a space between those layers, allowing for all wiring and connectivity to be embedded between those layers and also providing insulation and heat dissipation between the interior and exterior of the cabinet.

FIG. 5 illustrates a multi-layered frame whereby any or all facets of the cabinet can have at least two layers, inner layer 501, outer layer 502, and a space between those layers 503, allowing for all wiring and connectivity to be embedded between those layers and also providing insulation and heat dissipation between the interior and exterior of the cabinet. In one embodiment, all sides of the cabinet have inner layer 504 and outer layer 505 and the top and bottom sides of the cabinet have inner layer 507 and outer layer 506.

Figure 6:
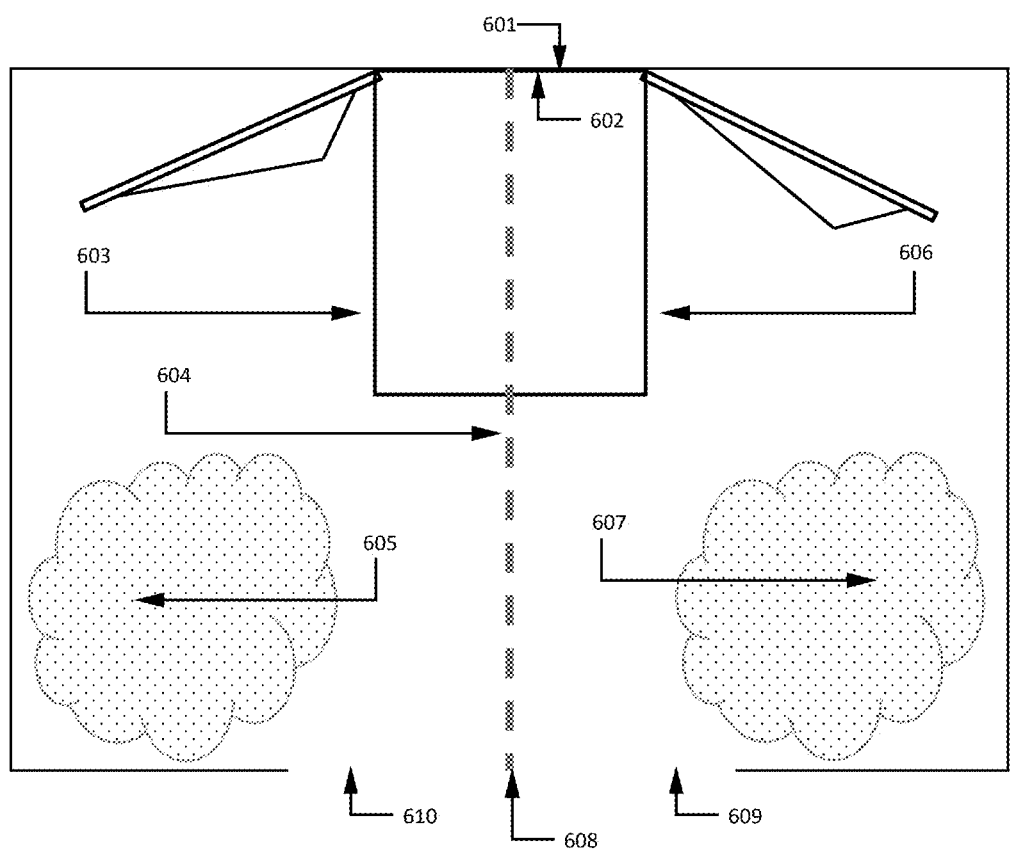
FIG. 6 illustrates a high perspective view of the cabinet as part of the room partition embodiment whereby the cabinet's multiple doors and cabinet combined with a drape or curtain or wall allows for separate work spaces, one for contaminated and one for disinfected.

FIG. 6 illustrates the cabinet positioned as part of a room partition where a side of the cabinet 602 is placed against a wall 601 with operator loading side 606 opposite non-operator unloading side 603, separated by a temporary or fixed partition or wall 608, allowing for separated work areas, "dirty" loading area 607, "clean" unloading area 605, separated loading doorway from unloading doorway 609 from unloading entrance 610. An operator can organize the inbound and outbound items for treatment based upon the ability for the cabinet and its design elements to be part of the room partition embodiment. Alternatively, the "dirty" loading vs. "clean" unloading access doors and their associated loading/unloading areas could be located differently than illustrated. Alternatively, the cabinet can be positioned to be part of a room partition in the middle, left or right location, as part of the room partition embodiment. This embodiment essentially includes a new and improved physical discipline in the disinfection process whereby the cabinet can have more than one access door, one or more doors for "dirty" items and one or more doors for "clean" items, allowing the operator to partition their cycle schedule and loading/unloading discipline with re-contamination risk lowered extensively. The embodiment allows for a 1st operator and 2nd operator, each operator working on separate side of the cabinet so a physical barrier can be erected around the cabinet (e.g. drape) so that the room is separated in half, dirty vs. clean (see FIG. 6).

Figure 7:
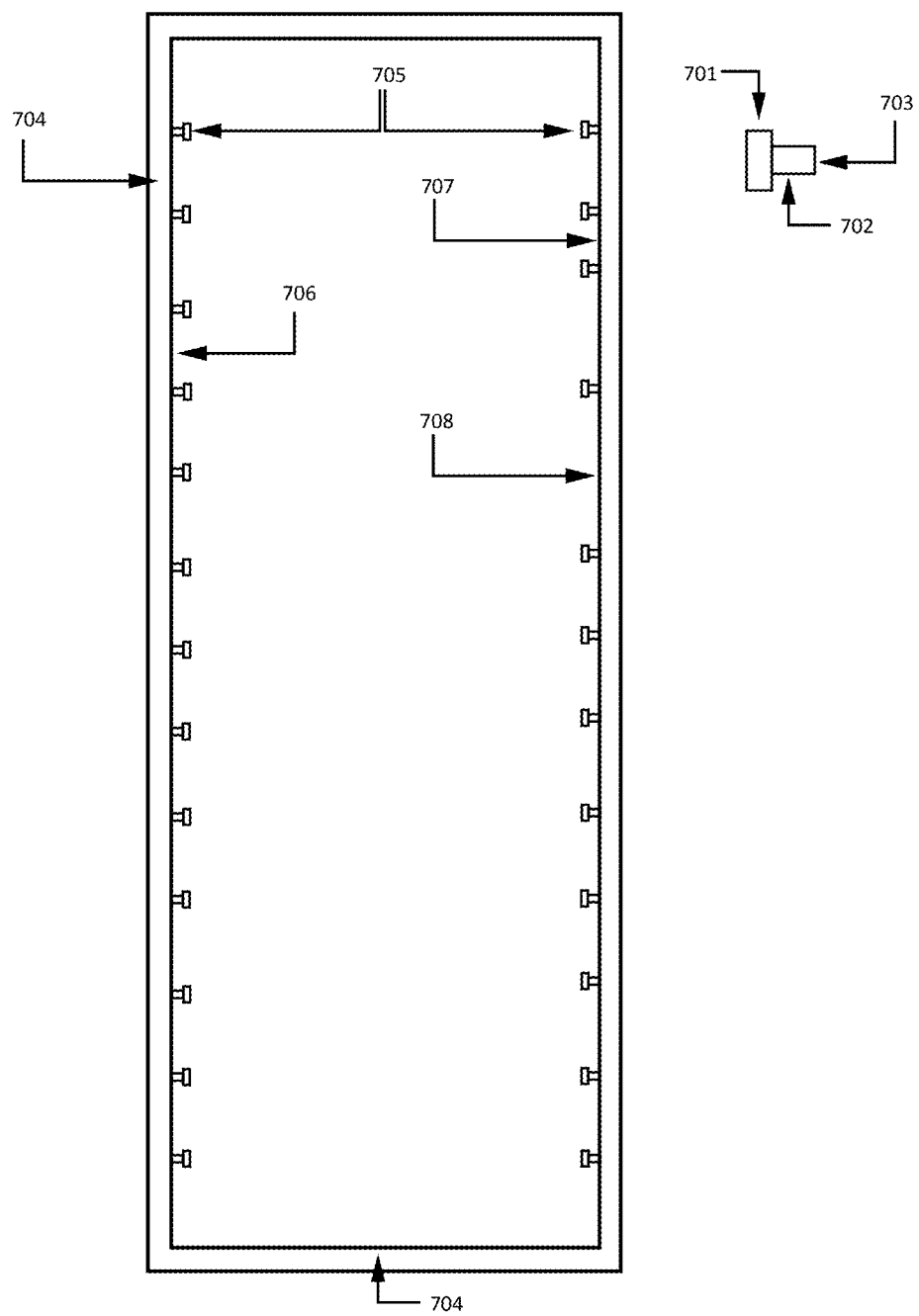
FIG. 7 illustrates a high perspective view of the item presentation framework embodiment of the cabinet whereby item mounting attachment points are located on the framework and item mounting brackets can be attached at one or more item mounting attachment points.

FIG. 7 illustrates the item presentation framework and attachment embodiment of the cabinet whereby item mounting attachment points 705 are located on the framework 704 in accordance with one embodiment. Item mounting attachment points refer to members, connectors, couplers, attachment points, connection points, protruding members, apertures, and so on that may be used to support one or more objects/items within the cabinet. Item mounting attachment points can be constructed of an edge 703 adjacent to the framework 704, an extension 702 from the framework that attaches to an anchoring point 701 whereby the anchoring point 701 has a physical attribute that provides anchoring leverage for any object with a reciprocating receiving attribute. Item mounting attachment points 705 can be spaced 706, 707, 708 along the framework or surface plane of the item presentation framework in an arrangement that provides flexible placement of item mounting attachments or the items themselves. Alternatively, the item presentation framework could be a different shape or dimensions while accomplishing the same mounting result for item mounting attachments, as an example, the item presentation framework could be a cylinder and item mounting attachment points can be holes and/or pegs positioned on and/or throughout the surface of the cylinder and selective physical guides can maintain the item's intended position. Alternatively, item mounting attachment points can be achieved for attachment using different attachment methods, including clips, magnets, brackets, notches, and any other means of attaching an item or item mounting bracket to the item presentation framework. For example, the item mounting attachment points 705 can be a protruding member that is detachably coupled with the framework 704, such as shank-style fasteners (i.e., bolts, screws, pins, etc.). The protruding member can be received by an opening or aperture of a bracket, as is shown in detail below with reference to FIGS. 21 and 22. Put another way, the aforementioned mounting attachment points 705 can be a male member, while the bracket can be a female member (i.e., an opening or aperture configured to receive the male mounting attachment point 705). In another example, the mounting attachment points 705 can define apertures or openings that are configured to receive a protrusion, protruding member, shaft, shank, projection, etc. of a bracket, as is discussed below with reference to FIG. 23. In such examples, the mounting attachment point 705 can be a female member that is configured to receive a male protrusion, protruding member, shaft, shank, projection, etc. of bracket. In some examples, the mounting attachment point 705 can comprise an aperture that is configured to receive a fastener (e.g., screw, rivet, pin, etc.), where the fastener is configured to be received by an opening or aperture defined by a bracket. In another embodiment, the mounting attachment point 705 can include an adhesive (e.g., sticky, adherent, epoxy, glue, etc.) element that can be configured to adhere to a bracket. In yet another example, the bracket can include an adhesive (e.g., glue, resin, epoxy, bonding agent, etc.) element that is configured to adhere to a mounting attachment point 705 or to the framework 704 generally.

The item presentation framework and attachment embodiment enables rapid loading and unloading of items within the enclosure via quick-connect item mounting adapters attached to the framework. Unique mounting adapters are provided as part of one embodiment to easily fit specific categories of items without any adaptation or tie-downs or added fixtures, saving the operator loading and unloading time and allowing for a custom mix of items per the needs of the operator. Improved treatment efficacy can be achieved via the item mounting adapters as they are customized to serve each category of item and achieve maximum surface area presentation from all sides of the item which therefore achieves maximum treatment exposure on all sides of the item, thereby lowering cycle times and increasing treatment effectiveness. The movement method and the power applied to the carrousel host framework can allow for 100% slippage if movement is blocked or if manual movement is desired by the operator when loading the enclosure and the carrousel assembly may be rotated to face the operator for loading and unloading purposes.

Figure 8A:
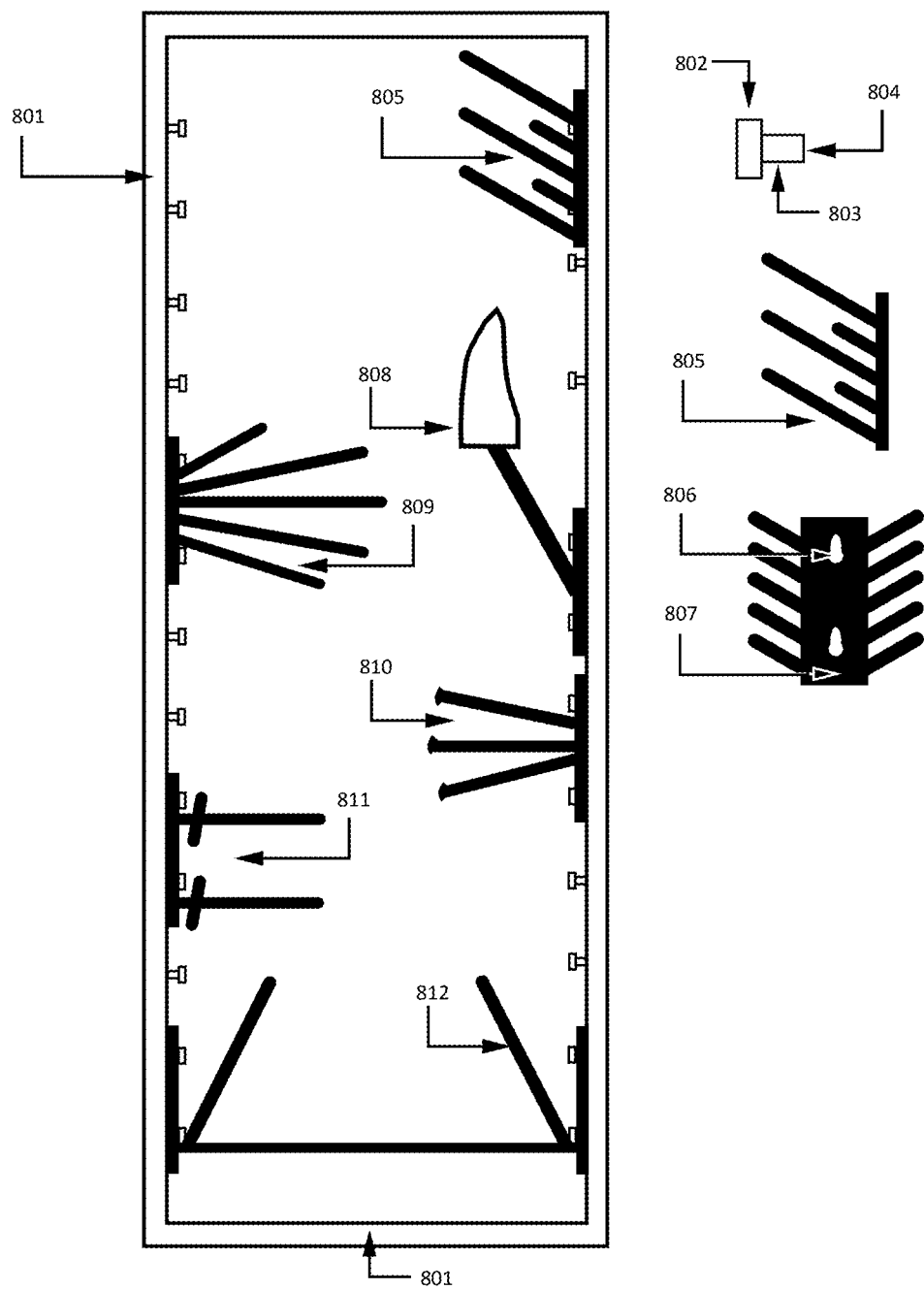
FIGS. 8A and 8B illustrate a high perspective view of the many possible item mounting brackets variably arranged and attached to the framework as item presentation framework embodiment of the cabinet.
Figure 8B:
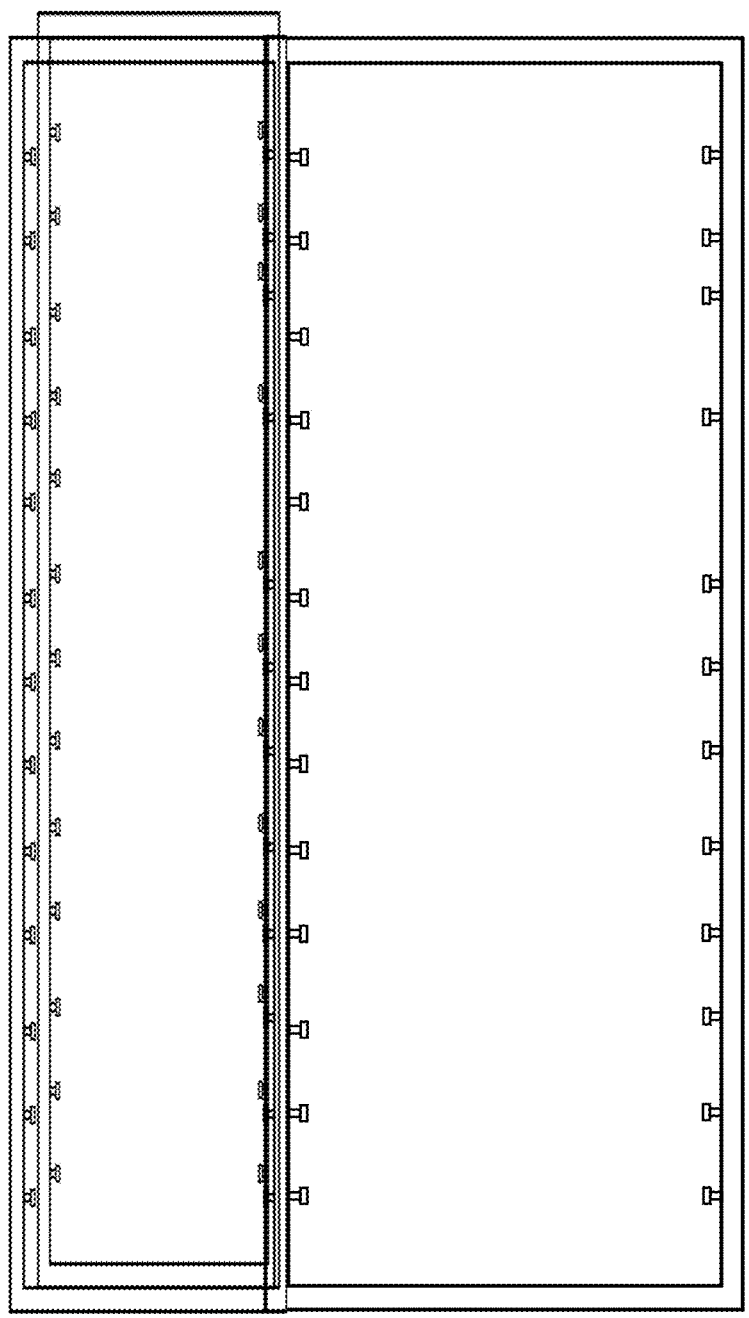

FIG. 8 illustrates possible item mounting brackets 805 that can be used with an item presentation framework, variably arranged and attached to the item presentation framework 801 with the item mounting attachment points 802, 803, 804 as located variably throughout the framework 801. Item mounting brackets 805 can be specifically designed for specific items found in the institution work or user environment. For example, a bracket 805 can be configured to support face shields, such as bracket 812 or the bracket assembly shown in FIGS. 30A and 30B and discussed below. In another example, a bracket 805 can be configured to support eyeglasses or goggles, such as bracket 811 or the bracket assembly shown in FIGS. 36A and 36B. In another embodiment, a bracket 805 can be configured to support paper or cloth facemasks or gloves, such as bracket 809 or the bracket assembly shown in FIGS. 35A and 35B and discussed below. Furthermore, a bracket 805 can be configured to support shoes, such as bracket 808 or the bracket assembly shown in FIGS. 28A and 28B. In yet another embodiment, a bracket 805 can be configured to support a phone, a wallet, keys, rings, and/or various other objects, such as the bracket assembly shown in FIGS. 29A and 29B. For any item mounting bracket 805, the item mounting bracket 805 can include a coupling member 806, such as an aperture or opening as shown in FIG. 8, that may be located within a mounting base 807. Via the coupling member 806, the item mounting bracket slides, snaps, affixes, attaches, couples, etc. to the mounting attachment points 802, 803, 804 of the item presentation framework 801.

One embodiment provides a new and improved item disinfection system and method which employs an item hosting framework with convenient "quick change" item adapter system via universal coupling members 806 and item mounting attachment points 802, 803, 804 so that various brackets 805 can be employed for the desired disinfection cycle. The operator of the cabinet may wish to employ a mix of brackets 805 for a variety of items or a concentration of a specific brackets 805 can be coupled to the item presentation framework 801 (e.g. a batch of masks and face shields). One embodiment provides a new and improved item disinfection system and method which employs the "quick change" item adapter system via universal attachment points whereby the item adapters quickly snap into place and have a small protruding locking pin mechanism to prevent unintentional detachment.

The aforementioned mounting attachment points 802, 803, 804 may correspond to a variety of brackets 805. More specifically, one or more brackets 805 can be configured to couple with one or more of the mounting attachment points 802, 803, 804. In some embodiments, the mounting attachment points 802, 803, 804 are male members that correspond with female coupling members of the brackets 805 (e.g., the female members may be or include apertures 806). In other embodiments not shown in FIG. 8, the mounting attachment points 802, 803, 804 are female members that correspond with male coupling members of the brackets 805 (i.e., protrusions, protruding members, pins, shafts, projections, etc.). Each of the mounting attachment points 802, 803, 804 may be spaced a distance apart from an adjacent mounting attachment point 802, 803, 804. In order to correspond with the mounting attachment points 802, 803, 804, each of the male or female coupling members (e.g., aperture 806) of the brackets 805 can also be spaced apart from an adjacent coupling member 806 at the same distance. In some embodiments, the brackets 805 may include a single coupling member 806 configured to couple with one mounting attachment point 802, 803, 804. In other embodiments, the brackets 805 may include two coupling members 806 configured to couple with two mounting attachment points 802, 803, 804. In yet other embodiments, the brackets 805 may include three coupling members configured to couple with three mounting attachment points. In various embodiments including brackets 805 having multiple coupling members 806, the coupling members 806 may correspond to adjacent mounting attachment points 802, 803, 804. In other embodiments including brackets 805 having multiple coupling members 806, the coupling members 806 may correspond to mounting attachment points 802, 803, 804 that are not adjacent.

As noted above, the brackets 805 can be specifically configured for use with certain items. For example, the brackets 805 may be designed to support a particular object in a particular manner to ensure or attempt to ensure that the object is adequately exposed to UV light, a vaporized chemical solution, circulating air, etc. within the cabinet during a disinfection or sterilization operation. In some embodiments, a particular object may be supported by a plurality of brackets 805 rather than a single bracket 805, which may be necessary for large, heavy, or bulky objects. The variety of objects that can be supported by brackets 805 is highly configurable and related to various industries. For example, the brackets 805 can be configured to support medical devices, personal protective equipment, physical therapy or chiropractic equipment, electronics, sporting equipment, clothing garments and accessories, eye protection equipment, and equipment regarding various other miscellaneous categories. Even more specifically, brackets 805 can be configured to support a mobile device (e.g., cell phone, tablet computer, walkie-talkie, etc.), a length of wire (for medical equipment or otherwise), a lead vest used for x-ray examinations, shoes, a facemask, a computer keyboard, laboratory or sporting goggles, gloves, eyeglasses or sunglasses, a sports ball (e.g., basketball, medicine ball, volleyball, etc.), a foam ball, a dumbbell, a foam roller, a massage device (e.g., massage gun), and so on. Furthermore, brackets 805 may be configured for general use, such as a basket for miscellaneous items, a hook for hanging items, or otherwise. Various bracket configurations are shown in FIGS. 25A-43B, which may in some embodiments, be used in place of or in addition to brackets 805.

Thus, as alluded to above, the brackets 805 can be specifically designed for a particular object or object category. As such, the brackets 805 can be configured to support an object in a manner that maximizes the surface area of the object that is exposed to an atomized liquid disinfectant, heat treatment, circulating air, UV light photodynamic therapy, mechanical wiping or brushing, a combination thereof, etc. within the cabinet during a disinfection and/or sterilization operation. More specifically, the bracket 805 can be configured in a manner that minimizes or substantially minimizes the number of touchpoints required to support the object. The bracket 805 can be configured in a manner that prevents or substantially prevents the bracket itself from reducing disinfectant and/or sterilization exposure on the object. For example, the bracket 805 can include a plurality of small, slender support members (as opposed to thick, bulky, large, etc. support members) configured to support and/or hold the object within the cabinet, where the slender members have a narrow acute edge adjacent to the object supported and thus do not substantially obstruct one or modes of disinfectant delivery to the supported object. In another embodiment, the brackets 805 can be configured to support the object in a manner that maximizes disinfectant and/or sterilization exposure on a portion of the object on which disinfection or sterilization is particularly important or necessary based on how the object is ordinarily used or what portions of the object are most likely to be exposed to bacteria, microbes, pathogens, etc. (e.g., the screen of a phone, the handle of a dumbbell, etc.).

In certain examples, a bracket 805 may be configured to support a heavy object, such as a medicine ball, portable massage device, dumbbell, kettlebell, or otherwise. Accordingly, a bracket configured to support heavy objects can include a plurality of coupling members (e.g., apertures 806) in order to increase the structural integrity of the bracket 805 when supporting a heavy object. Moreover, such brackets can be configured to provide structural integrity by, for example, having a larger cross-sectional shape than other brackets.

Brackets 805 may include visual indicators to describe their intended function (e.g., signage that indicates an intended object to support). In one embodiment, the brackets 805 are color-coded. For example, brackets 805 associated with physical therapy can be one color (e.g., green), while brackets associated with eye protection can be another color (e.g., red). Brackets 805 associated with electronics can be a third color (e.g., blue), while brackets 805 associated with personal protective equipment can be a fourth color (e.g., yellow). Brackets 805 associated with garments (e.g., shoes) can be a fifth color (e.g., white), while brackets 805 associated with miscellaneous items can be a sixth color (e.g., black). When the brackets 805 are color-coded, an operator is less likely to use an incorrect bracket in the cabinet as well as the operator is more likely to recognize their item at the end of the treatment cycle. Accordingly, it is more likely that the correct bracket 805 will be used so that disinfection and/or sterilization efficacy is maintained at a desirable level.

Figure 9:
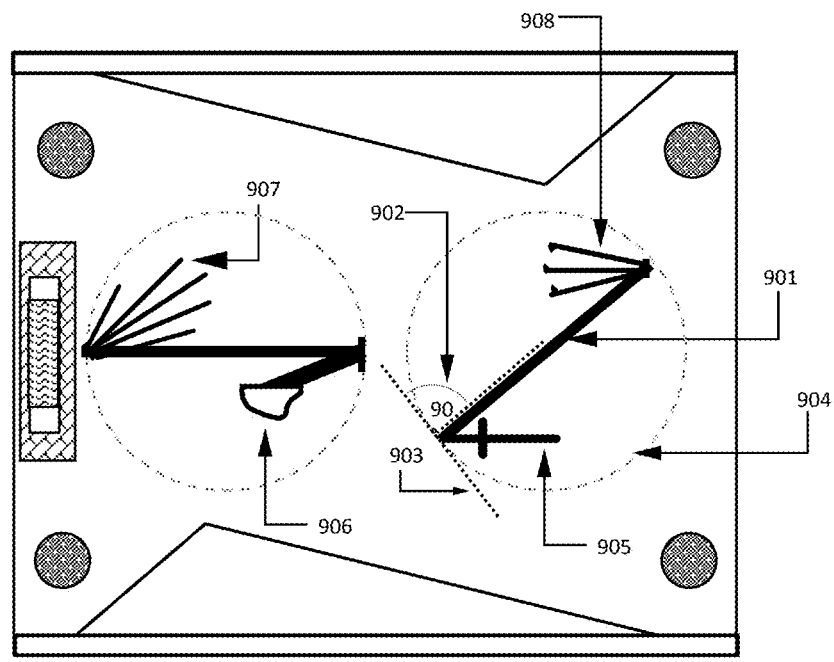
FIG. 9 illustrates a high perspective view of the internal space and item presentation to disinfection methods using the mounting bracket offset embodiment of the cabinet.

FIG. 9 illustrates the internal cabinet space and item presentation to all disinfection methods using an offset mounting bracket whereby the item presentation framework 901 moves within the carrousel movement area 904 and one or more item mounting attachments (i.e., brackets) 905, 906, 907, 908 are attached to the item presentation framework 901. The attachment can be mounted with its centerline at an interior "offset angle" between 0° and 90° from parallel or substantially parallel to the item presentation framework 901. The attachment can alternatively be mounted at an angle between 0° and 90° from a perpendicular line 903 whereby the item mounting attachments 905, 906, 907, 908 remain inside the carrousel movement area 904 yet are faced openly at an offset angle. When offset, items opposite each other on the item presentation framework 901 are presented in opposing offset angles so that they do not obscure any disinfection method presentation and do not physically collide when mounted and dismounted. This can make mounting and dismounting items easier in and around the item presentation framework 901 such that mounting or dismounting an item doesn't disturb another adjacent item. To further illustrate, within any framework or base of attachment, items mounted directly adjacent or directly opposed will force contact with one another during the mounting or dismounting effort, causing items to unintendedly touch or dismount or displace. One embodiment minimizes the opportunity for items to occlude, touch or displace each other at any time.

While FIG. 9 shows brackets mounted to two carrousels, other embodiments of the cabinet can include one carrousel or more than two carrousels. For example, the cabinet shown and described with reference to FIGS. 11-17 can include a single carrousel having a plurality of vertical columns, shafts, or posts coupled to a plurality of wings extending radially outward from a center point. In these embodiments, brackets can be mounted to the carrousel at an offset at a predefined angle (e.g., approximately 20°, approximately 30°, etc.) relative to the vertical columns, shafts, posts, etc. of the carrousel. For example, the brackets may be offset from parallel or substantially parallel to the item presentation framework 901 described above. According to an exemplary embodiment, the brackets may be offset a predefined amount (e.g., 20° plus-or-minus) 5° in a particular direction relative to the a wing of the carrousel of FIG. 11 or relative to the item presentation framework 901, as described above. The brackets may be each be offset in the same direction relative to the item presentation framework 901 (or the wing of the carrousel), such as in a clockwise direction or a counterclockwise direction, in order to further prevent any obstruction or obfuscation of one object by an object on an opposing side of the item presentation framework 901. Preventing obstruction or obfuscation further serves to bolster sterilization and/or disinfection efficacy. In other embodiments having a single carrousel, the brackets can be offset at an angle of more or less than the predefined amount (e.g., approximately) 20°.

In various embodiments, a plurality of different brackets can couple with mounting attachment points of the item presentation framework 901. In some embodiments, the mounting attachment points can comprise apertures configured to receive a male end of a bracket, as is shown and described below with reference to FIG. 23. In other embodiments, the mounting attachment points can comprise protrusions, such as fasteners (e.g., screws, bolts, hooks that are coupled with the item presentation framework 901, as is described below with reference to FIGS. 20-22. In some embodiments, each bracket may comprise a universal bracket base that can be coupled with the item presentation framework 901, while various bracket attachments configured to support a particular object are coupled with the universal bracket base (and therefore coupled with the item presentation framework 901).

Further disclosed herein is an item disinfection system and methods for making, distributing, and using the system with further embodiments.

In accordance with one embodiment, a cabinet can include a new and improved physical enclosure which is portable by one person, can be powered by a single conventional wall outlet or equivalent, self-contained as a closed system, can be operated indoors, can be operated with average personnel with little training, is quiet in operation, and has easy operator access to the enclosure interior.

In one embodiment, sensors, software and lights and screen displays serve as the control mechanisms of one embodiment to allow the operator to use, monitor, and troubleshoot the cabinet thereby assuring a safe and effective execution of the selected disinfection treatment plan.

In one embodiment, the system can be of a durable and reliable construction and may be easily and efficiently manufactured and marketed.

In one embodiment, the system can be made portable so that it can be located nearest the source of contaminants, can be optionally movable by only one person, can be configured to fit through any standard doorway, can be configured to be rolled upon wheels for easier transport, and can be configured to weigh less than 250 pounds.

One embodiment provides a new and improved item disinfection system and method which is constructed of high-grade institution-grade materials such as stainless steel, has no exposed wires, with all drive and control components located outside the disinfection area but located within the cabinet container.

One embodiment provides a new and improved item disinfection system and method which is efficient in the labor required to transport, load, and unload items for treatment as well as efficient in the time required to complete a treatment plan/cycle (generally in 15 minutes or less).

One embodiment provides a new and improved item disinfection system and method whereby the cabinet's software controls indicate the system's status whereby the operator can easily understand the status as "dirty/ready for cycle", "clean/ready to unload" with safety monitoring and messaging if a door is opened prematurely, the "dirty" door is opened before the "clean" door post-cycle, or if both "dirty" and "clean" doors are opened at the same time (these are contaminating events).

Figure 10A:
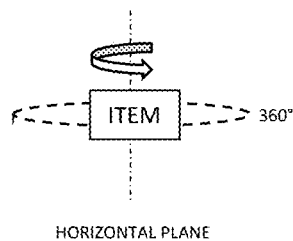
FIGS. 10A-D illustrate exposure to all disinfection methods and treatments by changing the position between item and disinfection method.
Figure 10B:
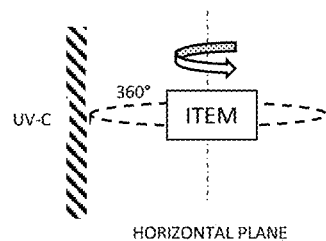
Figure 10C:
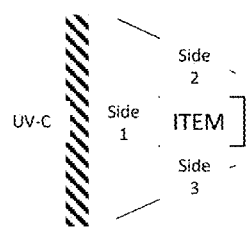
Figure 10D:
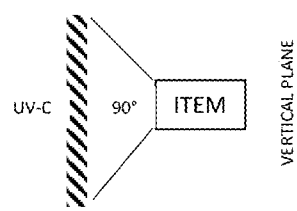

One embodiment provides a new and improved item disinfection system and method which provides 100% light-of-sight UV-C exposure by utilizing one or more UV-C sources whereby we position the item and light exposure to achieve via the item or treatment movement embodiment a 360 degree exposure on the horizontal plane that accomplishes a full exposure to all sides and surfaces of the item within a full range of movement (see FIGS. 10b, 10c).

One embodiment provides a new and improved item disinfection system and method which provides UV-C disinfection method from broad angles with a light-of-sight angle not less than 90 degrees up to 180 degrees in the vertical plane for any point of exposure facing the UV-C source, irrespective of item position within the enclosure. Further, this item presentation to the light achieves UV-C exposure to not less than 3 sides/surfaces of the item in the same instance (see FIG. 10D).

One embodiment provides a new and improved item disinfection system and method which provides a heat disinfection method whereby varying temperatures are achieve inside the enclosure for various durations to render various living contaminants inert or dead. The cabinet monitors interior temperatures to achieve a known surface temperature of the exposed items. Based upon item material sensitivities, the temperature may be increased and time decreased or temperature may be decreased and duration increased. The cabinet can reach temperatures up to 160° F. within 40 minutes or less. The addition of the rotating carrousel embodiment makes distribution of heat treatments among all items very uniform.

One embodiment provides a new and improved item disinfection system and method which provides air pressure and air flow disinfection enhancement method whereby the cabinet will maximize air pressure within the enclosure in order to increase the harshness of the environment upon living contaminants. The addition of the heat embodiment makes internal air especially effective in disinfection. The addition of the rotating carrousel embodiment makes distribution of air among all items very uniform.

One embodiment provides a new and improved item disinfection system and method which introduces and circulates a vaporized fog throughout the interior enclosure, coating all surfaces of contained items for the purpose of disinfection or freshening of appearance or smell. The amount of vaporized liquid and duration of application is controlled per the treatment plan. The liquid is a water-based chemical solution. The addition of the rotating carrousel embodiment makes distribution of vapor treatments among all items very uniform.

One embodiment provides a new and improved item disinfection system and method which provides humidity disinfection enhancement method whereby the cabinet's liquid vaporization capability will increase humidity within the enclosure in order increase the harshness of the environment upon living contaminants more sensitive to heat+ humidity combination. The cabinet can have the ability to apply heat+air flow+low humidity combination for maximum disinfection of one category of contaminants while separately applying heat+air flow+high humidity combination for maximum disinfection of another category of contaminants. The addition of the rotating carrousel embodiment makes distribution of heat and air and humidity treatments among all items very uniform.

One embodiment provides a new and improved item disinfection system and method which provides air flow drying enhancement method whereby the cabinet will move high volume of air across the surface of all contained items to facilitate drying of moist items and surfaces. The addition of the heat embodiment makes air more effective in moisture evaporation from item surfaces. The addition of the rotating carrousel embodiment makes distribution of air among all items very uniform.

One embodiment provides a new and improved disinfection system and method which allows pre-set or variable treatment plans that are a combination of disinfection methods, either in serial or overlapping order, with adjusted thresholds and duration (see FIG. 10E).

One embodiment provides a new and improved item disinfection system and method which has multiple sensors that serve to control the operating environment before, during, and following a treatment cycle. Use of these sensors assures the needed environmental factors are reached and maintained to assure treatment efficacy and operator safety. If any sensor indicates an incorrect status or no status, the system will not operate (see FIG. 10F).

Figure 11:
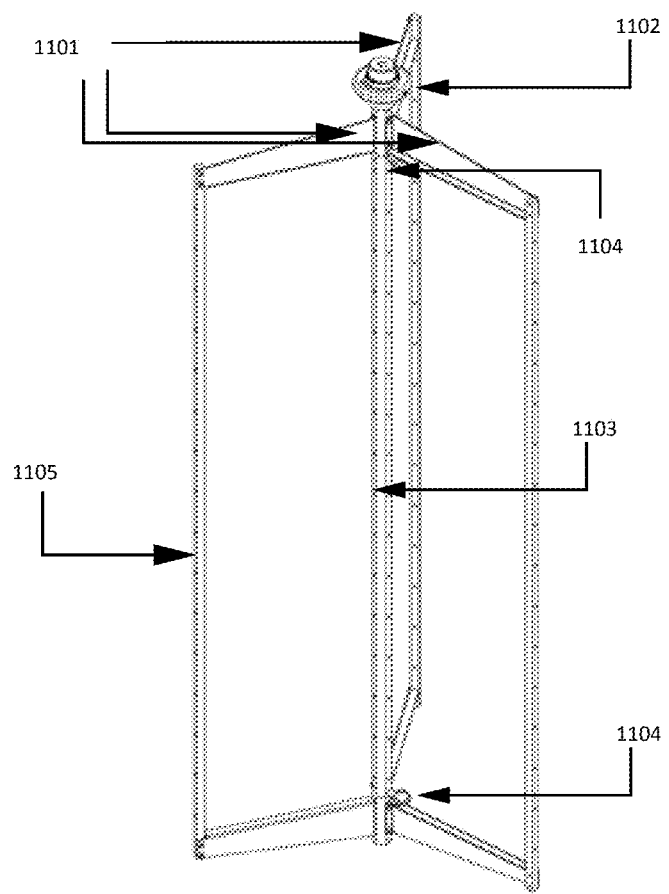
FIG. 11 illustrates a multi-wing carrousel embodiment whereby the carrousel is driven from the drive clutch.

FIG. 11 illustrates a multi-wing carrousel embodiment whereby the carrousel is driven from the drive clutch 102 that rotates the carrousel and allows for adjustable safety slippage, multiple wings 1101 connect to wing frames 1105 that provide maximum use of interior cabinet space around the center shaft 1103 which is removable to create a large interior carrousel space by removing the latch rings 1104. The multi-wing carrousel may be of unitary construction or an assembly of components coupled together. The components may include rod or beam members coupled together via one or more fasteners (e.g., screws, rivets, etc.) with or without adhesive, for example. According to an exemplary embodiment, the multi-wing carrousel can have three wings 1101. In other embodiments, the multi-wing carrousel can have fewer or more than three wings 1101. Each of the wings 1101 can be coupled to a wing frame 1105, which can be formed as a shaft, beam, post, etc. More specifically, each of the wing frames 1105 can be members that extend vertically or substantially vertical (perpendicular or substantially perpendicular relative a horizontal plane) when installed within the cabinet and connect a top member of each wing 1101 to a bottom member of the same wing 1101. Furthermore, each of the wing frames 1105 can include a plurality of bracket mounting means (e.g., item mounting attachment points 802, 803, 804) configured to couple with a bracket for supporting an item within the cabinet, particularly during a sterilization and/or disinfection cycle. In some embodiments, one or more of the wing frames 1105 can include a plurality of apertures configured to receive a male end of a bracket, as is described below in detail with reference to FIG. 23. In another embodiment, one or more of the wing frames 1105 can include a plurality of protrusions configured to be received by an aperture of a bracket, as is described in detail below with reference to FIGS. 20-22. In such embodiments, the protrusion can be a fastener (e.g., screw, bolt, etc.) that is fastened to the wing frame 1105.

As noted above, a center post 1103 of the multi-wing carrousel assembly can be removable to allow for larger objects to be disinfected or to fit the operational needs of the user and bracket positioning. More specifically, the center post 1103 can be configured to detachably couple with the multi-wing carrousel assembly at a top end and a bottom end, where each of the top end and the bottom end are coupled to the multi-wing carrousel assembly via some coupling means, shown as a latch ring 1104. In the example shown, the latch rings 1104 can be removed from the top end and the bottom end of the center post 1103, thereby decoupling the center post 1103 from the multi-wing carrousel assembly. In operation, apertures at the top and bottom of the center post 1103 may align with apertures at the top and bottom of the carrousel. When aligned, latch rings (e.g., pins, rods, etc.) may be inserted through the apertures to couple the center post 1103 to the assembly. In other embodiments, the center post 1103 can be coupled with the multi-wing carrousel assembly via some other means (e.g., spring-loaded pins, threading the center post 1103 into a nut coupled with the multi-wing carrousel assembly, etc.). In an exemplary embodiment, when the center post 1103 is removed, the multi-wing carrousel assembly can be configured to support one or more large, bulky, and/or heavy items via one or more of the wing frames 1105. In some embodiments, a large, bulky, and/or heavy item can be supported by multiple brackets coupled with a wing frame 1105. In another embodiment, a large, bulky, and/or heavy item can be supported by a plurality of brackets couple with a plurality of wing frames 1105 (e.g., a first bracket coupled with a first wing frame 1105 and a second bracket coupled with a second wing frame 1105), as is shown and described below with reference to FIG. 24.

Figure 12:
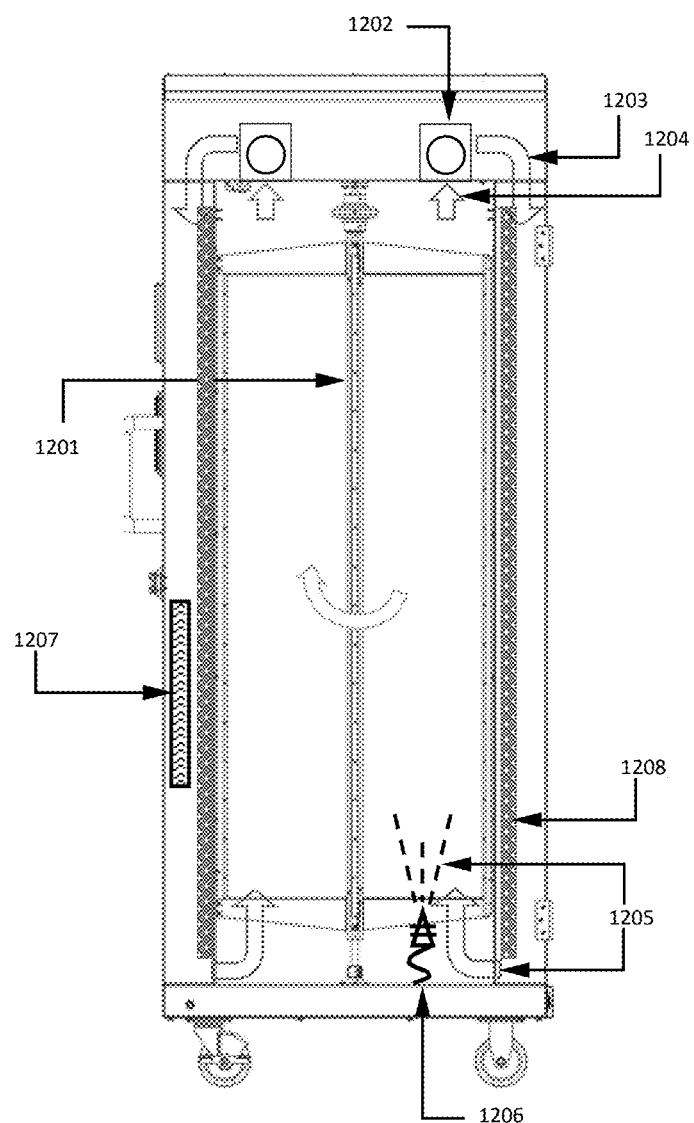
FIG. 12 illustrates a cross sectional elevation view of a four-corner embodiment where the rotating carrousel is surrounded by germicidal light sources.

FIG. 12 illustrates a cross sectional elevation view of a four-corner embodiment where the rotating carrousel 1201 is surrounded by germicidal light sources 1208 as interior air is ingested 1204 into a fan 1202 outside the interior space and air is moved into the nearest corner duct 1203 moving downward to the cabinet bottom, passing by heater 1207 and re-entering the cabinet 1205 whereby the air can force interior microbes and vapor vertically while the carrousel is moving items horizontally. The resulting air flow 1205 1204 passes all along the warm surface of the germicidal light component 1208, providing a cooling effect upon the light.

Figure 13:
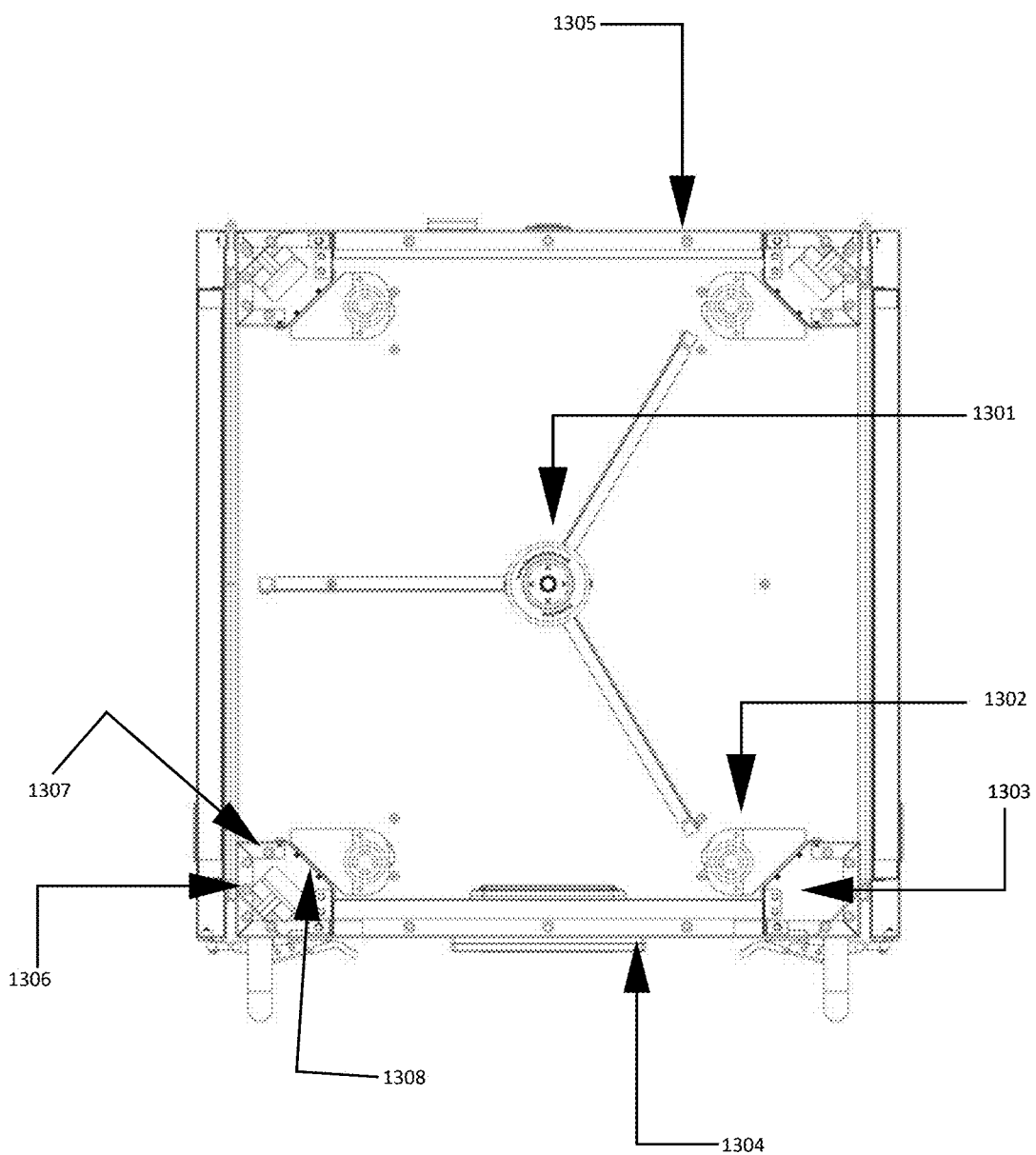
FIG. 13 illustrates a cross sectional overhead view of a four-corner embodiment where the rotating carrousel is surrounded by germicidal light sources.

FIG. 13 illustrates a cross sectional overhead view of a four-corner embodiment where the rotating carrousel 1301 is surrounded by germicidal light sources 1302 as interior air is moved into the nearest corner duct 1303 moving downward to the cabinet bottom. The corner duct 1303 can be formed in part by a front wall 1304 and/or rear wall 1305 of the cabinet, according to one embodiment. The front wall 1304 may be proximate a viewing window and handles of the cabinet, while the rear wall 1305 may be proximate a power switch and power outlet, according to one embodiment. More specifically, the front wall and the rear wall of the cabinet can comprise a C-shaped cross section whereby two ends of the front wall and rear wall curl in-wards towards an interior space or volume of the cabinet. More specifically, the front wall can include a first section 1304 and the rear wall can include a first rear section 1305. Each of the first section 1304 and the second section 1305 can include a second section 1306 extending substantially perpendicularly to the first section 1304 or 1305 (and substantially parallel to side panels or doors), and a third section extending from the second section 1306 parallel to the first section 1304, 1305. A cover or panel 1308 may be coupled with an interior surface of the first section 1304, 1305 and the third section, thereby enclosing forming the corner duct 1303 within a portion of the first section 1304, 1305, the second section 1306, and the third section 1307. According to an exemplary embodiment, the corner duct 1303 can remain enclosed (i.e., separated from the interior or exterior of the cabinet) when a side door of the cabinet is opened. The second section 1306 and the third section 1307 may also be coupled to a top and a bottom of the cabinet to provide structural support, according to one embodiment. As discussed in further detail below with reference to FIG. 16, the corner ducts 1303 can also facilitate the circulation of air (or atomized disinfectant solution, as desired) throughout the cabinet, whether in connection with a disinfection or sterilization cycle or otherwise. For example, the corner ducts 1303 can facilitate the movement of air from a bottom of the cabinet to a top of the cabinet or vice versa.

Figure 14:
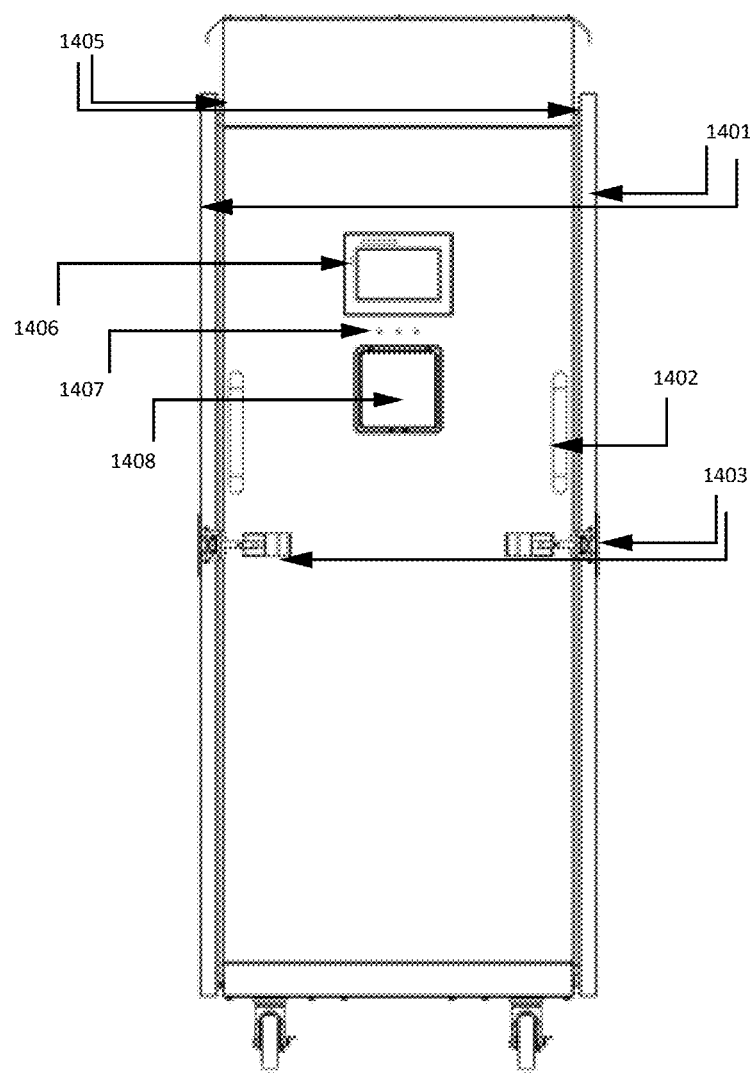
FIG. 14 illustrates a side view of a multiple access door embodiment whereby doors are located on opposite sides of the cabinet.

FIG. 14 illustrates a side view of a multiple access door embodiment whereby doors 1401 are located on opposite sides of the cabinet with a steering handle 1402 on each side, each door with a manual lock 1403. A further safety door embodiment provides an automated lock 1405 on any access door 1401. The front-facing status embodiment allows for complete machine status to be visible from the front plane 1409 containing a computer screen HMI 1406, status indicator lights 1407 and viewing window 1408 and manual door locks 1403.

Figure 15:
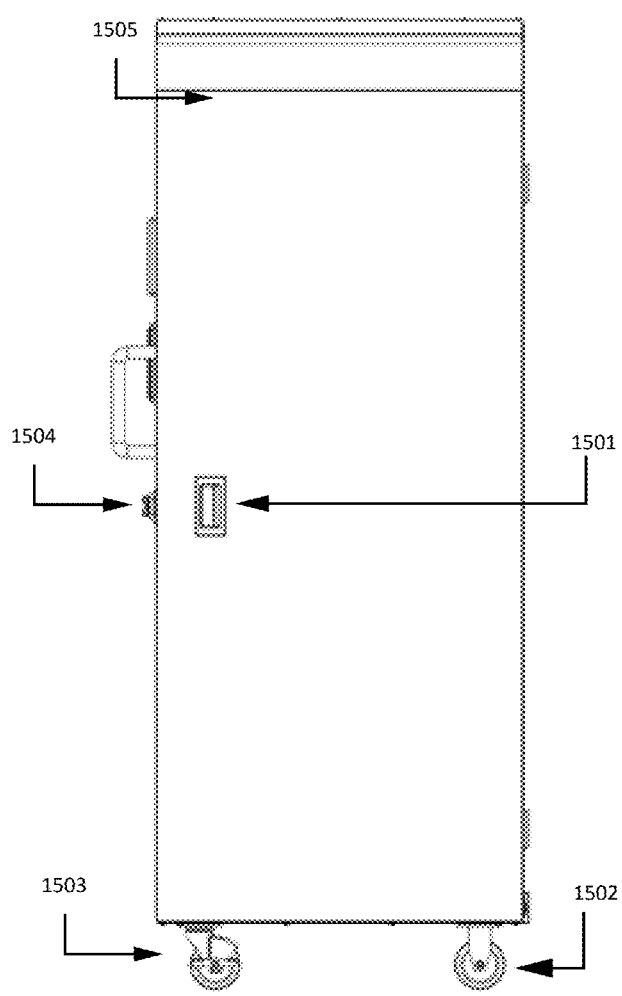
FIG. 15 shows an embodiment including a door with pull handle.

FIG. 15 shows an embodiment including a door with pull handle 1501, manual door lock 1504, automated door lock 1505, fixed wheel 1502 and steerable, lockable wheel 1503. The automated door lock 1505 can be an electromagnetic door lock positioned between the door of the cabinet and an internal structure, such as a frame of the cabinet. The automatic lock can be configured to lock the side door in response to an indication that a disinfection and/or sterilization cycle is occurring or is scheduled to occur within a predetermined amount of time. When the door is locked, the automatic lock 1505 can substantially prevent access to an interior of the cabinet until the disinfection or sterilization cycle is complete, according to one embodiment. In another embodiment, the automatic door lock 1505 can be unlocked in response to an operator command (e.g., manual override command). The automatic locks 1505 can therefore bolster the efficacy of the device by ensuring that access to the cabinet interior is not or is substantially not allowed in certain circumstances, even if an operator forgets to lock the manual lock 1504.

Figure 16:
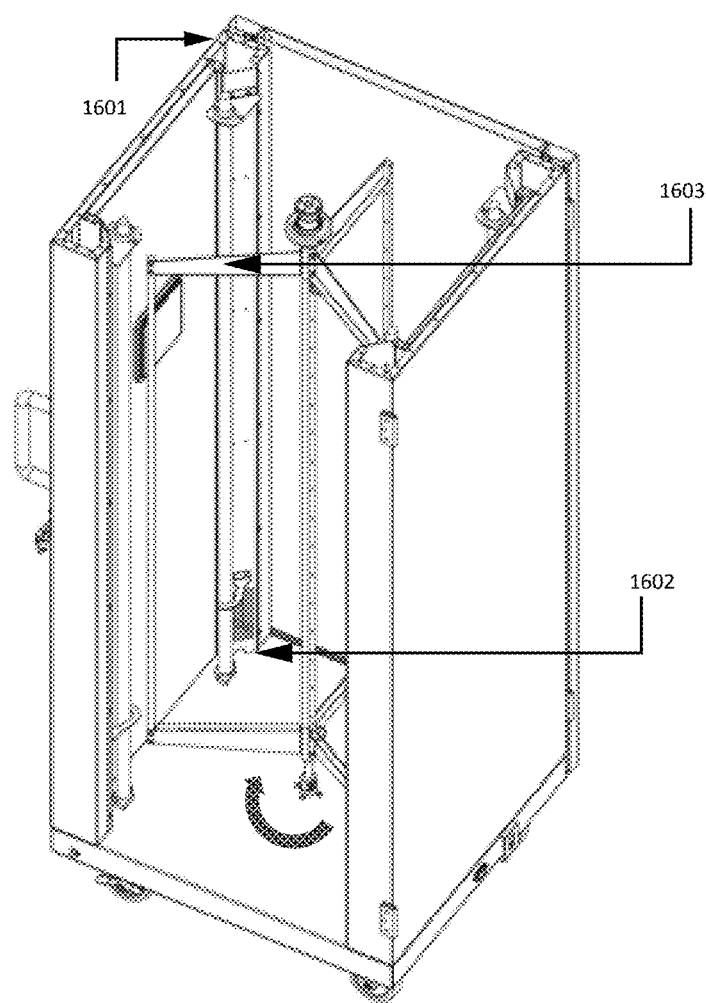
FIG. 16 illustrates a perspective cut away view of a four-corner embodiment where the cabinet's structural frame is also an air duct.

FIG. 16 illustrates a perspective cut away view of a four-corner embodiment where the cabinet's structural frame is also an air duct. More specifically, structural elements (i.e., the first section 1304, 1305, the second section 1306, and the third section 1307 shown in FIG. 13) at each corner of the cabinet's interior can be a duct for moving or circulating air throughout the cabinet interior. The duct can include a top member 1601 and a bottom member 1602. According to an exemplary embodiment, the duct extends as part of the cabinet frame the full or nearly the full length of the interior cabinet space, providing controlled air flow from top of duct 1601 to bottom of duct 1602. In another embodiment, the duct provides controlled air flow from the bottom of the duct 1602 to the top of the duct 1601. As carrousel 1603 rotates within the cabinet interior, the air flow can be moved, directed, or otherwise guided vertically from bottom to top, from top to bottom, or otherwise. In various embodiments, the duct can circulate hot, cold, room, or another desired temperature air (for example, a heater may be used to heat the air prior to circulation, a heat exchanger may be used to cool the air prior to circulation, etc.) throughout the cabinet in connection with a disinfection or sterilization cycle. The duct can also include a plurality of perforations, apertures, vents, or openings between the top of the duct 1601 and the bottom of the duct 1602 to allow air to circulate between the top 1601 and the bottom 1602. In some embodiments, the ducts can be fluidly coupled to one or more blower motors, fans, or other devices configured to generate air flow. Such devices can be fluidly coupled to the duct in a location proximate to the top 1601, proximate to the bottom 1602, or otherwise. In addition to facilitating air circulation within the cabinet, the duct as herein described can also provide structural support and rigidity for the cabinet itself. For example, the duct may be coupled to one or more adjacent walls (e.g., a front wall, back wall, bottom wall, top wall) and can act as an additional structural member within the cabinet to bolster structural rigidity thereof.

Figure 17:
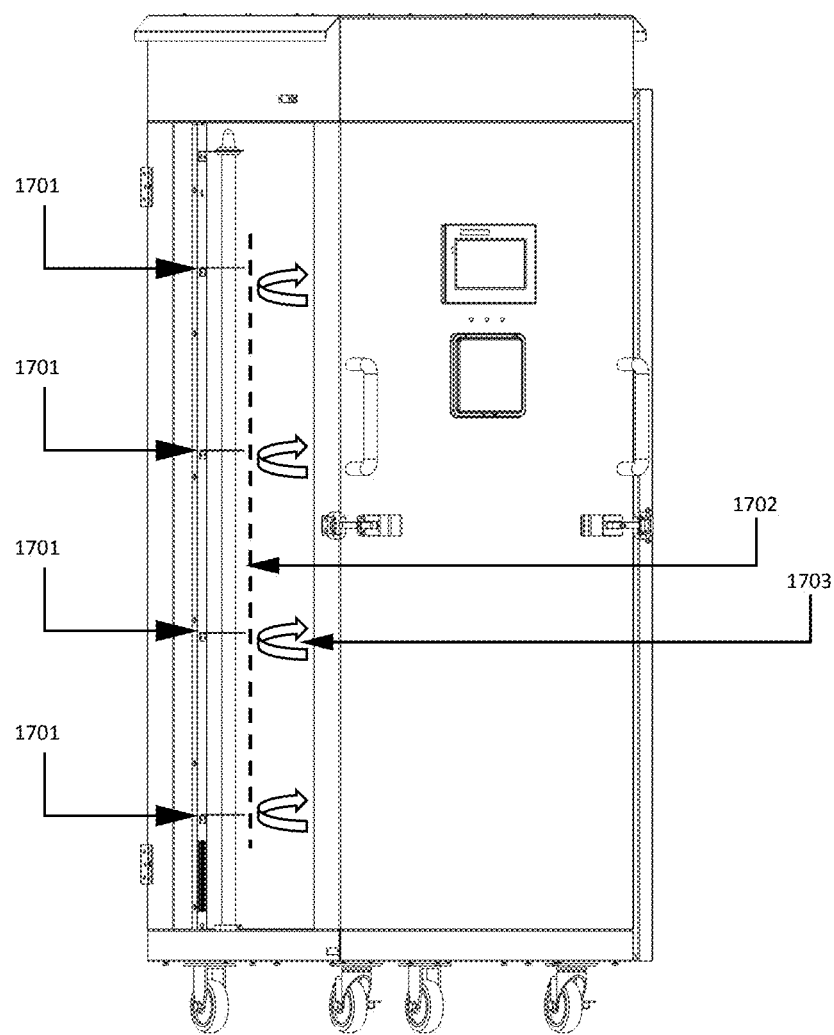
FIG. 17 illustrates an embodiment of the cabinet's internal space using item physical guides.

FIG. 17 illustrates an embodiment of the cabinet's internal space using item physical guides. As the framework carrousel moves at its center point 360° within carrousel movement area 1703 items contained within the carrousel could potentially shift outside of intended movement range 1702 whereby all or a portion of any item could extend beyond the carrousel movement area 1703 and if so, item physical guide points 1701 are positioned to protrude and nudge the item toward carrousel movement area 1703 and prevent the item from leaving the carrousel movement area 1703 where the item would be prevented from receiving or would prevent other items from receiving full treatment by chosen disinfection methods. The item physical guides provide a new and improved item disinfection system and method which has built-in physical guide material on the interior of the enclosure or door assembly whereby any item that becomes misaligned with its intended position as it rotates is nudged toward its original intended position so that it remains in place for exposure as well as it does not affect any other item or the cabinet's mechanisms. Alternatively, the item can be moved upon a conveyor or carriage and a similar physical guide can be positioned to assure the item remains in its intended position throughout the treatment cycle.

Figure 18:
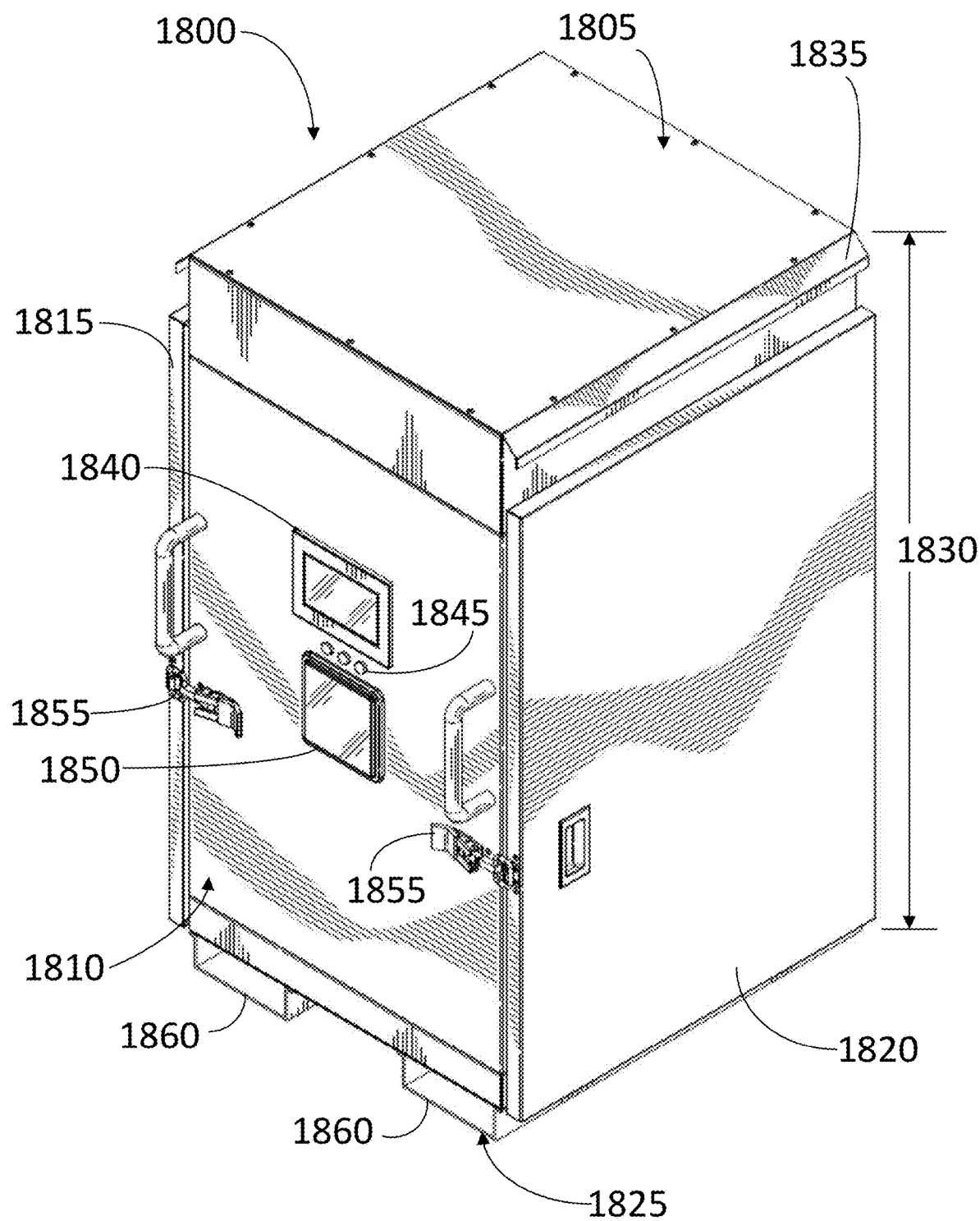
FIG. 18 is a perspective view of a disinfection and/or sterilization cabinet, according to an example embodiment.

Referring now to FIG. 18, a disinfection cabinet 1800 is shown according to another embodiment. The disinfection cabinet 1800 can include a top portion or member 1805, a front portion or member 1810, a first side door 1815 coupled to a rear portion or member, a second side door 1820 coupled to the rear portion or member, and a bottom portion or member 1825. The cabinet 1800 can include a height 1830 that spans from the top 1805 to the bottom 1825. According to an exemplary embodiment, the height 1830 of the cabinet is less than a height of a cabinet of the embodiment shown in FIGS. 12-17. The cabinet 1800 can be configured for use on a desktop, table, countertop, or other surface that is elevated from a ground surface, for example. Because the cabinet 1800 can be used on an elevated surface, the cabinet 1800 can have a shortened height (relative to other cabinet embodiments) so that the top 1805 of the cabinet does not or likely does not interfere with a ceiling of a room or building where the cabinet 1800 is used, for example. Although the cabinet 1800 may have a shorter height 1830 than other cabinet embodiments, the interior of the cabinet can be similar to other cabinet embodiments in many respects. For example, the cabinet 1800 can include a rotating carrousel structure configured to receive one or more brackets for supporting objects during a disinfection or sterilization operation.

The top 1805 of the cabinet 1800 can further include a guard or shield 1835. The guard or shield 1835 can be configured to prevent rain or other materials (e.g., debris, dust, etc.) from entering or likely entering the top 1805 of the cabinet 1800 and interfering with electronics or mechanical devices housed within the top 1805 and associated with operation of the cabinet 1800. Beneficially, the cabinet 1800 may be disposed in outdoor environments with the electronics of the cabinet substantially shielded from various environmental conditions (e.g., rain, etc.). In some embodiments, the cabinet 1800 can be used in military environments where exposure to elements (i.e., debris, dust, vibrations, etc.) may be prevalent and the design of the cabinet 1800 includes features to assure ruggedness in the field. Accordingly the guard or shield 1835 can protect the cabinet 1800 from certain elements to ensure the cabinet 1800 operates at a desired efficacy level.

The front portion or member 1810 can include a display device 1840, one or more indicators 1845, and can define a viewing window 1850. In one example, the display device 1840 can include or be a touch screen device that is configured to receive an input from a user related to the operation of the cabinet 1800 and/or provide one or more graphical user interfaces. More specifically, a user may initiate a disinfection or sterilization cycle, stop the initiated cycle, monitor progress of the initiated cycle, and/or modify a disinfection or sterilization cycle of the cabinet 1800 as discussed above. The display device 1840 may also display a current status of a disinfection or sterilization cycle, such as an amount of time remaining for the cycle, a current stage of the cycle, etc. The indicators 1845 are configured to provide a visual and/or audible indication of a current status of the cabinet 1800, the objects within the cabinet that are subject to the disinfection or sterilization cycle, and/or a combination thereof. In one example, the indicators 1845 can include three lights where each light can be configured to indicate a status of the objects within the cabinet 1800. The lights may be LED lights or another type of light-emitting source. For example, a red light can indicate that the objects within the cabinet 1800 have not been sterilized or disinfected, a yellow light can indicate that the objects within the cabinet are currently undergoing a disinfection or sterilization, and a green light can indicate that the objects within the cabinet 1800 have been successfully disinfected or sterilized (i.e., that the cycle is complete). The indicators 1845 may thus provide a clear and substantially unambiguous visual indication to an operator or attendant of the cabinet 1800.

The viewing window 1850 can be configured to allow an operator to view an interior of the cabinet 1800, according to an exemplary embodiment. Because UV light may be used within the cabinet to disinfect and/or sterilize, the viewing window 1850 may be coated or otherwise treated to prevent harm to the eyes of an individual viewing the interior of the cabinet during a disinfection or sterilization cycle.

The cabinet 1800 can also include two or more latches 1855 that are configured to prevent or substantially prevent an operator from accessing an interior chamber of the cabinet 1800 via doors 1815, 1820. In some embodiments, the latches 1855 can be manually operated latches that are actuated by an operator. In another example, the latches 1855 may be automatically locking locks. For example, the latches 1855 can be electro-magnetic or electromechanical latches that lock in response to a received electrical current, where the electrical current can be received when a disinfection and/or sterilization cycle is initiated. More specifically, an electromagnetic lock may energize mating magnetic surfaces on the side door 1820 or 1815 and the front portion member 1810. In another embodiment, the automatic lock may be a solenoid-actuated lock that is activated to cause the movement of the latch into a latch receptacle to lock the door to the cabinet 1800. Accordingly, the doors 1815 and 1820 may be locked when a disinfection or sterilization cycle is in process.

The bottom 1825 of the cabinet 1800 may include a plurality of slots 1860. The slots 1860 can be configured to receive tines of a hand-operated fork truck, a fork lift, a telehandler, or other equipment with fork tines, for example. In another embodiment, the slots 1860 can contain extendable carrying handles that, when extended, allow for manual movement of the cabinet by one or more operators. According to one embodiment, the bottom 1825 can include slots 1860 instead of any wheels or rollers. In another embodiment, the bottom 1825 can also include wheels, rollers, casters, etc. that allow the cabinet 1800 to be pushed or rolled along a surface. The bottom member or portion 1825 can also include friction-adding elements (e.g., rubberized feet) that are configured to prevent the cabinet 1800 from sliding or moving on a surface. In another embodiment, the bottom member or portion 1825 may further include various fixtures or brackets configured to fixedly couple the cabinet 1800 to a surface via fasteners, an adhesive, welding, etc.

Figure 19:
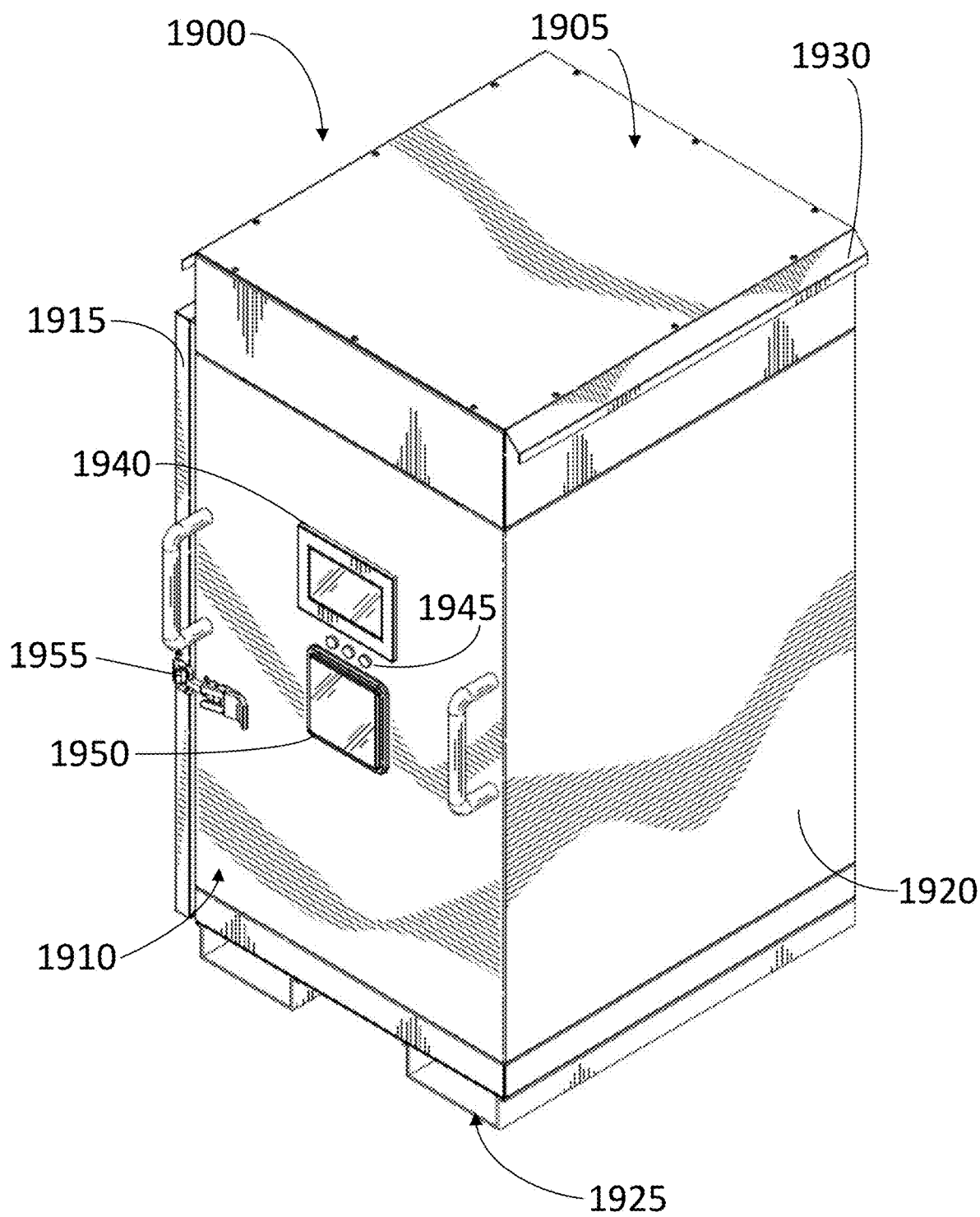
FIG. 19 is a perspective view of a disinfection and/or sterilization cabinet, according to another example embodiment.

Referring now to FIG. 19, a disinfection cabinet is shown, according to yet another embodiment. The cabinet 1900 is shown to include a top portion or member 1905, a front portion or member 1910, a first door 1915 coupled to a rear portion or member, a side panel 1920 coupled to the rear portion or member and the front portion or member 1910, and a bottom 1925. The top portion or member 1905 of the cabinet 1900 is also shown to include a guard or shield 1930 that may be coupled to the top portion 1905 (e.g., via one or more fasteners, such as rivets, screws, etc.) or be integral with the top portion 1905. The guard or shield 1930 is configured to prevent rain or other materials (e.g., debris, dust, etc.) from entering the top portion or member 1905 of the cabinet 1900 and potentially interfering with any electronics or mechanical devices housed within the top portion or member 1905 and associated with the operations of the cabinet 1900.

The front portion or member 1910 is shown to include a display device 1940, an indicator 1945, and defining a viewing window 1950. In some embodiments, the display device 1940 can be similar to the display device 1840 of the cabinet 1800 discussed above and shown in FIG. 18. For example, the display device 1940 can be or include a touch screen device that is configured to receive an input from a user related to the operation of the cabinet 1900 and provide one or more graphical user interfaces. In some embodiments, the indicators 1945 can be configured to provide a visual and/or audible indication of an operational status of the cabinet 1900, objects within the cabinet 1900 that are subject to the disinfection or sterilization cycle, and/or a combination thereof. The viewing window 1950 can be configured to allow an operator or an attendant to view an interior of the cabinet 1900, according to an exemplary embodiment. Because UV light may be used within the cabinet to disinfect and/or sterilize, the viewing window 1950 may be coated or otherwise treated to prevent harm to the eyes of an individual viewing the interior of the cabinet during a disinfection or sterilization cycle.

The first door 1915 of the cabinet 1900 is movably coupled to the cabinet 1900 (particularly, the rear portion or member) (e.g., via a hinge or other means that enables the door to move relative to the cabinet 1900). The first door 1915 is movable, and particularly rotatable, between a first or closed position that prevents access to an interior chamber or space of the cabinet 1900 and a second or open position where the door 1915 is spaced apart from the cabinet 1900 to provide access to an interior chamber of the cabinet 1900. The first door 1915 can include or be coupled to a latch 1955 that, when in a latched (i.e., locked or closed) state can prevent the first door 1915 from opening (i.e., retaining the door in the first position). Rather than having a second door positioned on an opposite side from the first door 1915 (like the cabinet 1800), the cabinet 1900 can include a side panel 1920. The side panel 1920 may be rigidly coupled with and/or integral with the front panel or portion 1910 and a back panel or portion of the cabinet 1900. The side panel 1920 therefore does not provide access to the interior of the cabinet 1900. The interior space of the cabinet 1900 can therefore only be accessed via actuation of the single door 1915, according to an exemplary embodiment. While the door 1915 is shown on a left side of the cabinet 1900 in FIG. 19, in various examples, the first door 1915 can instead be positioned on the right side (in place of panel 1920), on the rear portion or member (i.e., opposite side of the front portion or member 1910 shown in FIG. 19), or on the front side. With respect to the front side configuration, the viewing window 1950, indicator 1945, and/or display device 1940 may be coupled to the door 1915 such that they are movable fore and aft relative to the interior space of the cabinet 1900 based on movement of the door 1915.

Figure 20:
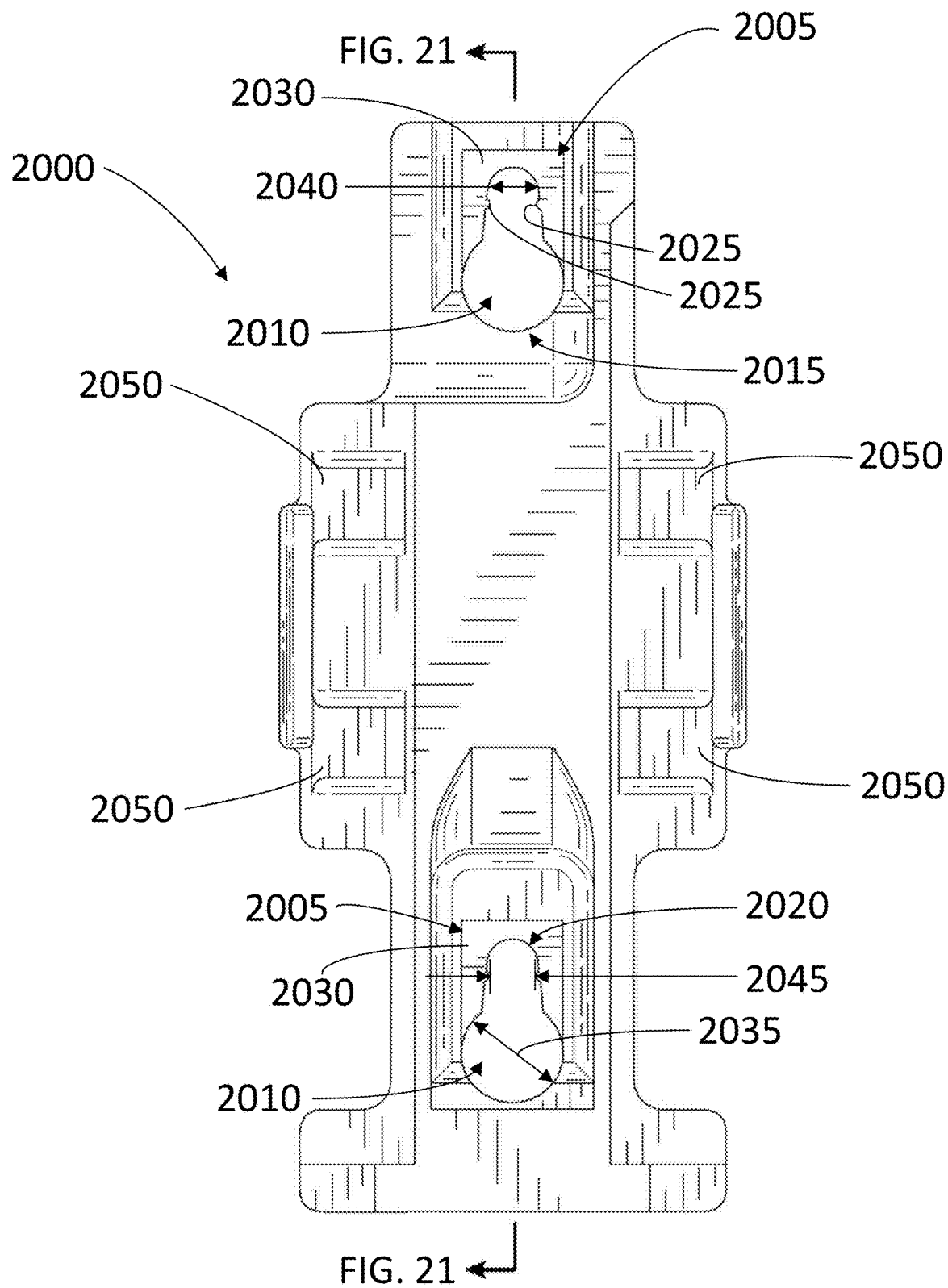
FIG. 20 is a front view of a universal bracket base, according to an example embodiment.

Referring now to FIG. 20, a universal bracket base 2000 is shown, according to an example. As discussed above, the disinfection cabinet can be configured to couple with one or more brackets that support various objects within the cabinet. Each of the brackets can include a universal bracket base or support member 2000, according to an exemplary embodiment. The universal bracket base 2000 can be configured to couple with an interior framework of a cabinet, such as a carrousel similar to that shown in FIGS. 8, 9, 11 and 24, for example. The universal bracket base 2000 is configured to couple to one or more brackets or bracket attachments to support one or more objects within the cabinet to undergo or experience a disinfection and/or sterilization cycle. In some embodiments, the one or more bracket attachments (or "support members") can be detachably coupled with the universal 2000 base. Accordingly, the universal base may remain coupled to the interior framework (particularly, the carrousel) while one or more bracket attachments are coupled with or decoupled from the universal bracket base 2000. In other embodiments, the bracket attachments can be fixedly coupled with or integrally formed with the universal bracket base 2000 such that the bracket attachment is not removable from the universal bracket base 2000.

The universal bracket base 2000 can include one or more couplers or coupling structures 2005. The coupling structures 2005 are configured to facilitate the coupling of the universal bracket base 2000 to an interior framework or frame of a cabinet, namely a protrusion or aperture of the interior framework as described above with reference to FIGS. 7 and 8. For example, the coupling structures may be apertures or openings that are configured to receive a protrusion, protruding member, pin, shaft, fastener, peg, etc. of a rotating carrousel of a cabinet. More specifically, the carrousel can have a plurality of wings extending radially from a center point and columns, posts, or shafts coupled to a distal end of the wings and extending vertically in a downwards direction (i.e., perpendicular or substantially perpendicular to a horizontal plane), where each of the columns, posts, or shafts can have a plurality of protrusions, protruding members, pins, shafts, fasteners, etc. that are received by the coupling structures 2005 (i.e., an aperture). In another example, the coupling structure coupled be a protrusion, protruding member, pin, shaft, fastener, etc. that is configured to be received by one or more apertures defined by the aforementioned columns, posts, or shafts of a rotating carrousel. In the example shown, the coupling structures 2005 are structured as apertures or openings 2010. The opening 2010 is shown to include a first opening 2015 having a first diameter 2035 that flows into a second opening 2020 having a second diameter 2040. According to one embodiment, the first diameter 2035 is greater than the second diameter 2040. The first opening 2015 and the second opening 2020 collectively form the opening 2010. In various embodiments, the first opening 2015 and the second opening 2020 can have the same or a similar shape (e.g., a circular, semi-circular, or curved shape). In other embodiments, the first opening 2015 and the second opening 2020 can have a different shape (e.g., the first opening 2015 can be circular shaped while the second opening 2020 has a rectangular shape).

The coupling structures 2005 of the universal bracket base 2000 are also shown to include one or more protrusions 2025 (e.g., projections, notches, etc.) extending into the opening 2010 and, in the example shown, located between the first opening 2015 and the second opening 2020. In the example shown, the coupling structures 2005 include two protrusions 2025 positioned on opposing sides of the opening 2010 relative to each other. Ends of each of the two protrusions 2025 are separated by a protrusion distance 2045. According to an exemplary embodiment, the protrusion distance 2045 is less than the second diameter 2040 of the second opening 2020. As a result, the protrusions 2025 narrow the opening 2010. More specifically, the opening 2010 can be at its narrowest between the protrusions 2025.

The universal bracket base 2000 may further include one or more bracket attachment (or support member) coupling structures, also referred to as bracket couplers 2050. In the example shown, the bracket couplers 2050 are structured as openings or apertures 2050 defined by the base 2000. In other embodiments, different types of bracket couplers may be employed in addition to or in place of the apertures or openings 2050 (e.g., mechanical fasteners, such as screws or bolts may be employed, the brackets may be integral with the universal base 2000, a bonding agent may be used to couple the brackets to the base 2000, etc.). Each aperture is structured to receive a projection of a bracket attachment to support the bracket attachment and couple the bracket attachment to the base 2000. As noted above, the universal bracket base 2000 can be configured to couple with one or more bracket attachments. The bracket attachments can be configured to support one or more objects positioned within a disinfection and sterilization cabinet as herein described (e.g., cabinet 1800 and 1900). Example bracket attachments (also referred to as support members), bracket bases, and bracket couplers are shown and described with respect to FIGS. 25A-42B herein.

In some embodiments, the bracket attachment or support member may be a hook configured to support a lab coat or other hanging item. In another example, the support bracket can be a small basket configured to support miscellaneous small items (e.g., medical devices, medical supplies, jewelry, fitness bands, ear buds, etc.). In yet another example, the support bracket may be a plurality of hooks configured to support a dumbbell. The support bracket may be specifically designed to support a particular object. For this reason, certain support brackets may not be compatible with certain objects. Therefore, it may be necessary for the support bracket to be changed as a certain object is placed within the cabinet. To facilitate convenient and rapid changing of bracket attachments, the universal bracket base 2000 may be configured to remain coupled with an interior framework of the cabinet (as discussed in further detail below with reference to FIGS. 21 and 22) while the bracket attachment or support bracket is changed.

In the example shown, the universal bracket base 2000 is primarily rectangular in shape, includes two coupling structures 2005 configured to enable coupling of the universal bracket base 2000 to an interior framework or frame of a cabinet, and includes four bracket couplers 2050 for coupling to one or more support brackets for supporting one or more objects within the cabinet. In one embodiment, one support bracket is coupled to one universal base 2000 (e.g., via at least one projection being received by at least one bracket coupler 2050). In another embodiment, more than one support bracket is coupled to one universal base 2000. For example and with reference to FIG. 20, a first support bracket may include two projections that are received by the left most bracket couplers 2050 while a second support bracket may include two projections that are received by the right most bracket couplers 2050. Alternatively, the two top most bracket couplers 2050 may couple to the first support bracket while the two bottom-most bracket couplers 2050 may couple to the second support bracket. Given this configurability, the bracket base 2000 may also be highly configurable: have a different shape than the depicted rectangular shape; include less than or more than four bracket couplers 2050; include less than or more than two coupling structures 2005; include different shapes, sizes, and/or types of bracket couplers 2050 and/or coupling structures 2005; and so on. Thus, the depicted configuration is exemplary only with other variations possible.

Referring now briefly to FIGS. 25A-42B, example bracket attachments or bracket assemblies are shown, are shown according to various example embodiments. In these embodiments, a bracket base is coupled to a support member to form a bracket attachment assembly. The assembly may be coupled to the frame or other internal framework of the cabinet. In other embodiments, the support member(s) and bracket base may be of integral construction (a unitary component).

Figure 25A:
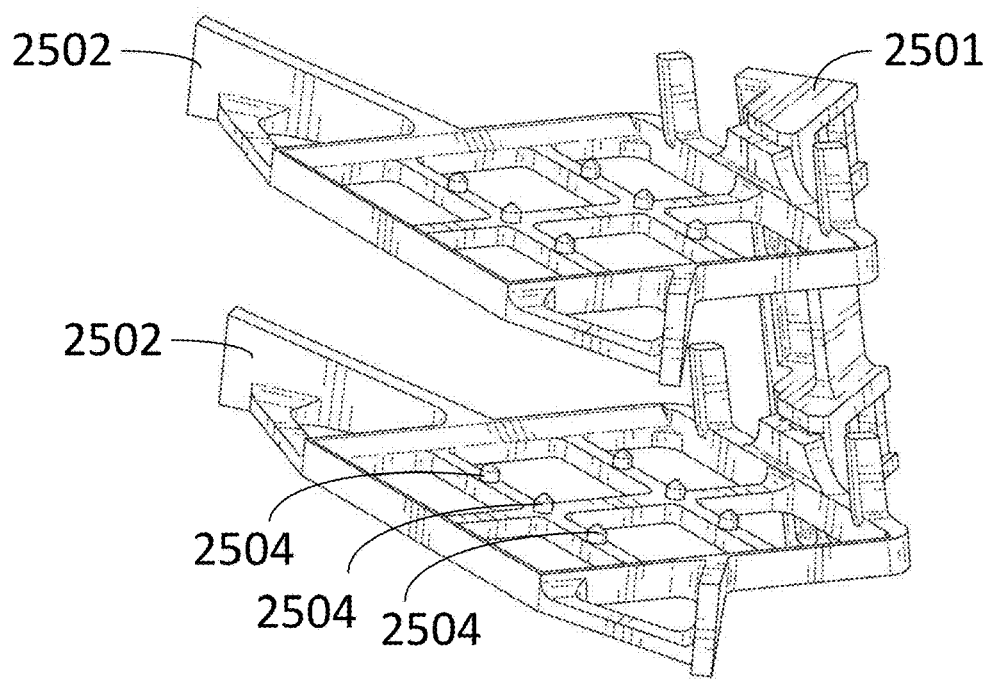
FIGS. 25A and 25B are a front (FIG. 25A) and rear (FIG. 25B) perspective views of a bracket, according to an example embodiment.
Figure 25B:
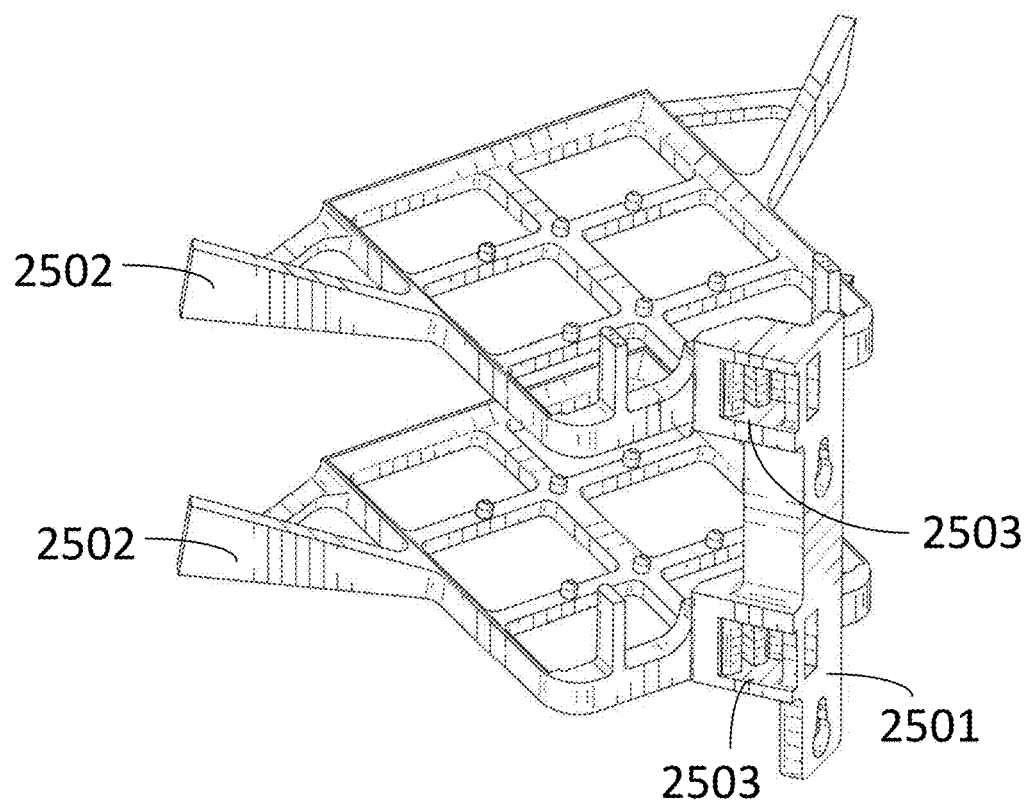

FIGS. 25A-25B show front and rear perspective views of an example bracket assembly that may be used to support a wallet, a mobile phone (or other mobile electronic or other equipment), or a tablet computer, according to an example embodiment. FIGS. 25A-25B shows the bracket assembly including a bracket base 2501, support members 2502 coupled to and extending outward and away from the base 2501, and a plurality of bracket couplers 2503 of the bracket base 2501 configured to couple to the support members 2502 (e.g., apertures that receive projections of the support members 2502). The support members 2502 are configured to support one or more objects (in this case, a mobile device but other objects are conceivable). In the example shown, the support members 2502 include a plurality of low-contact touchpoints or objects 2504, which are shown in this example as projections with a pyramidal or conical shape.

Figure 26A:
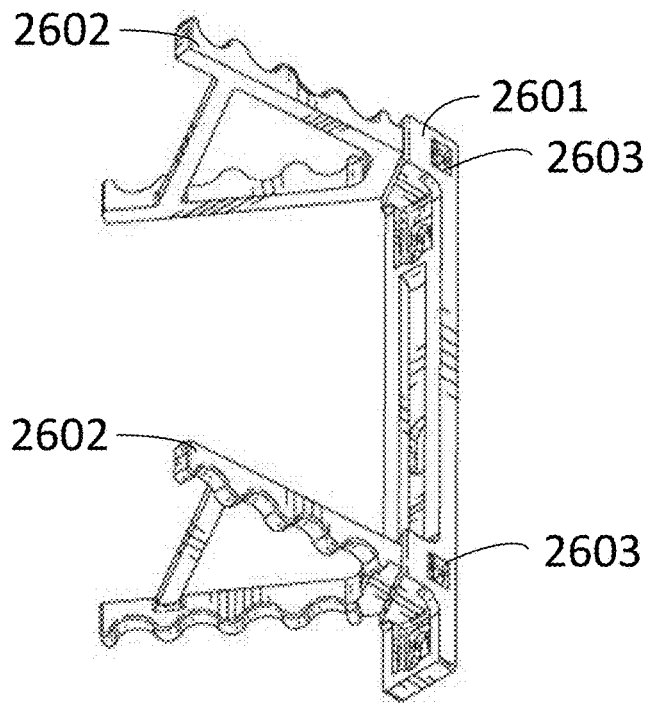
FIGS. 26A and 26B are front (FIG. 26A) and rear (FIG. 26B) perspective views of a bracket, according to another example embodiment.
Figure 26B:
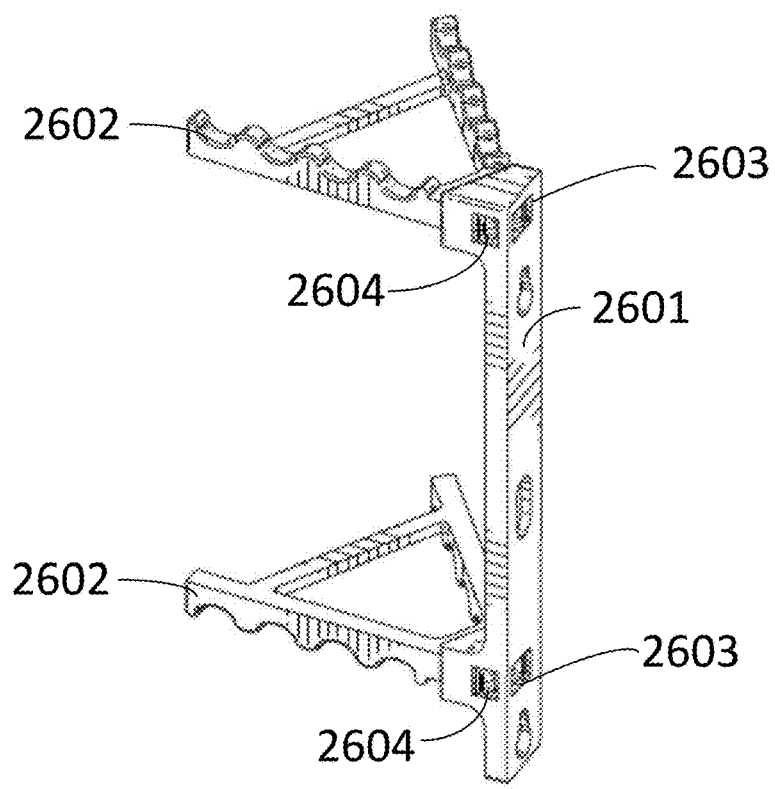

FIGS. 26A-26B show front and rear perspective views of an example bracket assembly that may be used to support a cord or a wire (or other type of flexible object), according to an example embodiment. FIGS. 26A-26B show the bracket assembly including a bracket base 2601, support members 2602 coupled to and extending outward and away from the base 2601, and a plurality of bracket couplers 2603 of the bracket base 2601 configured to couple to the support members 2602 (e.g., apertures that receive projections of the support members 2602). The support members 2602 define a plurality of ridges that may support multiple objects, such as multiple wires.

Figure 27A:
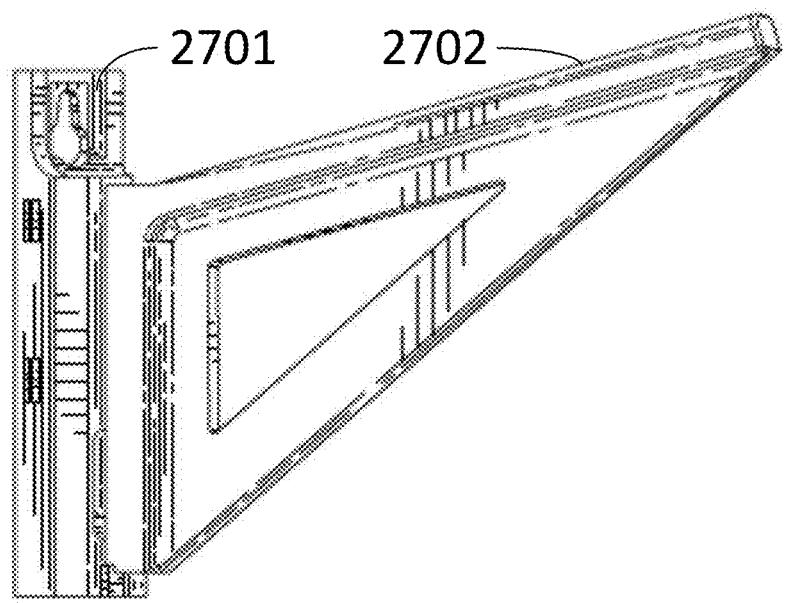
FIGS. 27A and 27B are front (FIG. 27A) and rear (FIG. 27B) perspective views of a bracket, according to still another example embodiment.
Figure 27B:
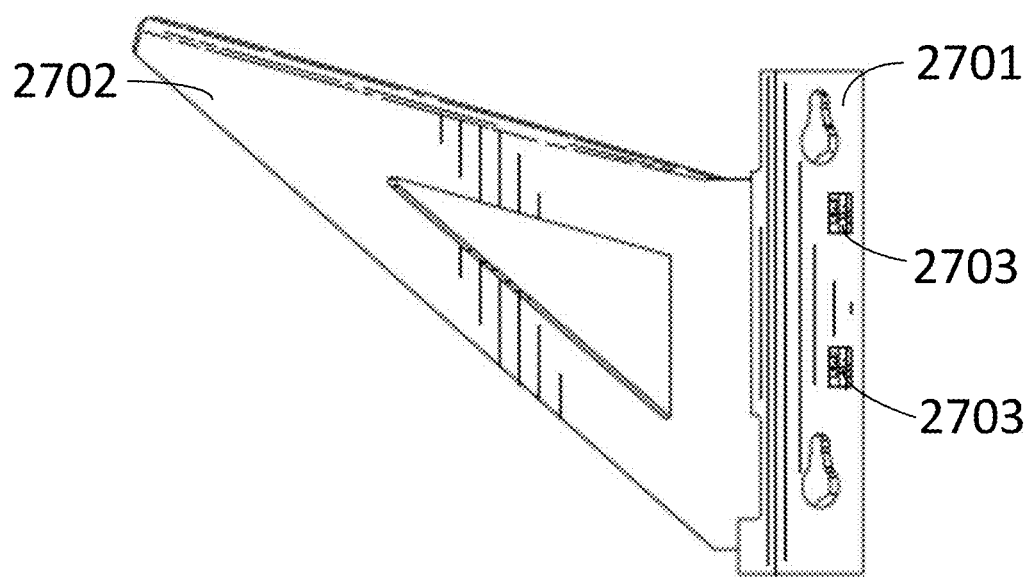

FIGS. 27A-27B show front and rear perspective views of an example bracket support member that may be used to support a garment, such as a lead vest, according to an example embodiment. FIGS. 27A-27B show the bracket assembly including a bracket base 2701, a support member 2702 coupled to and extending outward and away from the base 2701, and a plurality of bracket couplers 2703 that couple the support member 2702 to the base 2701 (e.g., apertures that receive projections of the support members 2702).

Figure 28A:
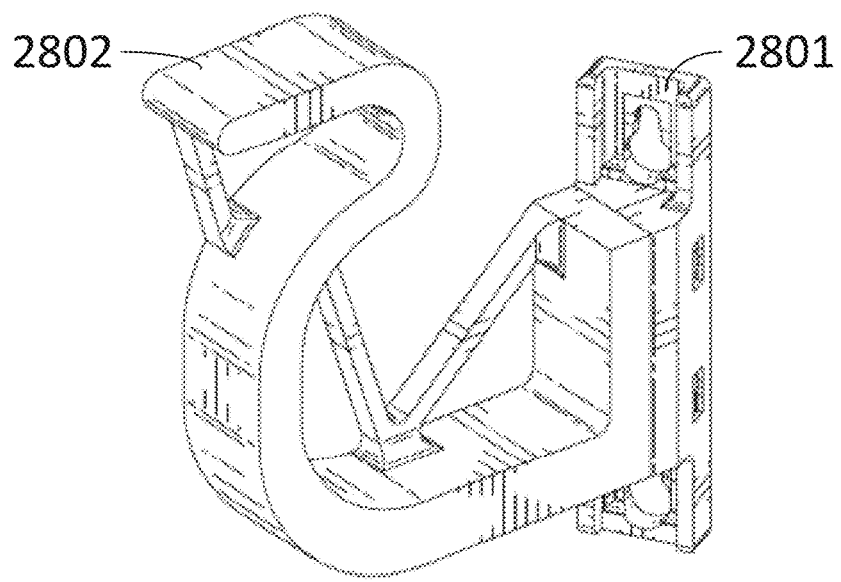
FIGS. 28A and 28B are front (FIG. 28A) and rear (FIG. 28B) perspective views of a bracket, according to yet another example embodiment.
Figure 28B:
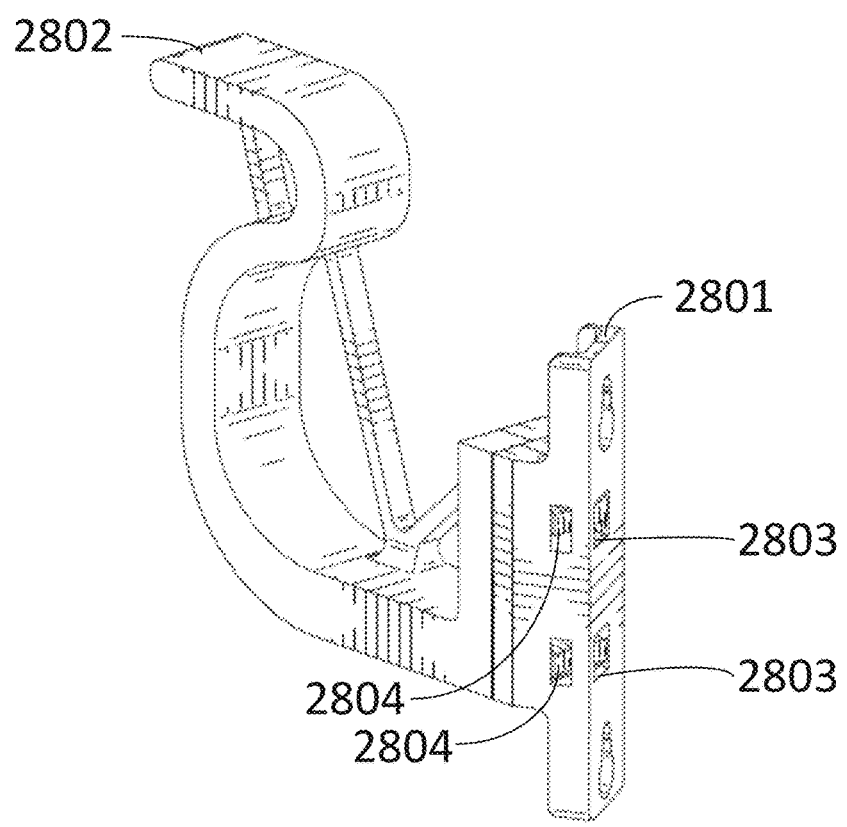

FIGS. 28A-28B show front and rear perspective views of an example bracket assembly that may be used to support a shoe, according to an example embodiment. FIGS. 28A-28B show the bracket assembly including a bracket base 2801, a support member 2802 defining a primarily S-shaped structure coupled to and extending away from the base 2801, and a plurality of bracket couplers 2803 that are used to couple the support member 2802 to the base 2801. In this regard, the support member 2802 can include a projection 2804 configured to be received by the bracket couplers 2803, which are shown as apertures or openings.

Figure 29A:
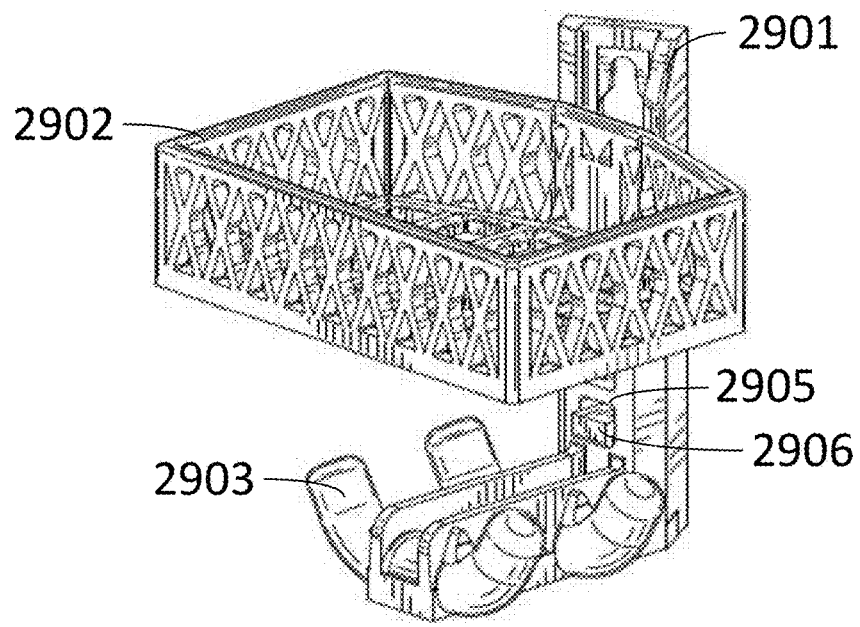
FIGS. 29A and 29B are front (FIG. 29A) and rear (FIG. 29B) perspective views of a bracket, according to yet another example embodiment.
Figure 29B:
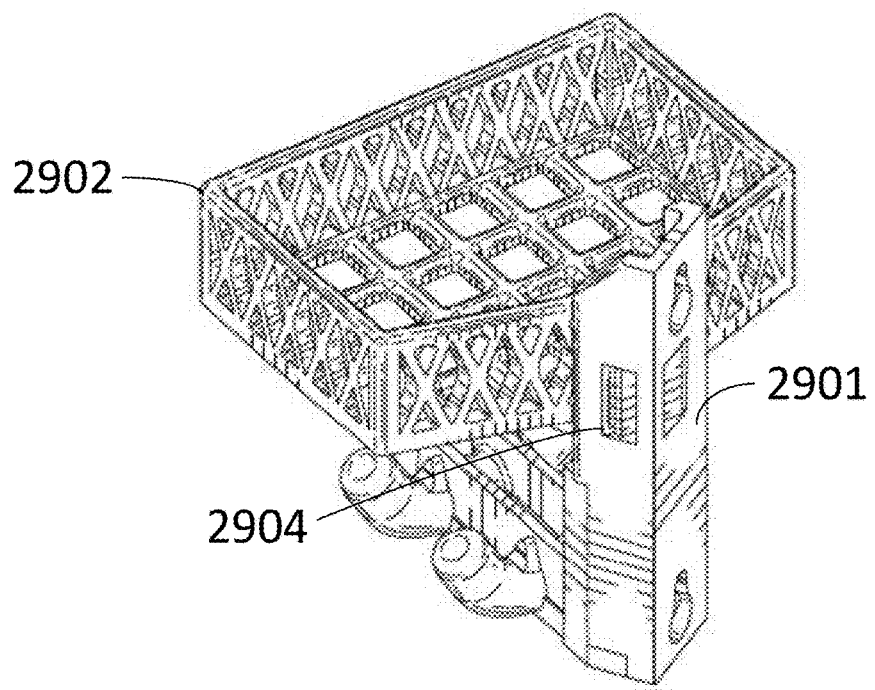

FIGS. 29A-29B show front and rear perspective views of an example bracket assembly that may be used to support rings and miscellaneous items (e.g., medical supplies, jewelry, keys, etc.), according to an example embodiment. FIGS. 29A-29B show the bracket assembly including a bracket base 2901, a first support member 2902 coupled to and extending away from the base 2901, a second support member 2903 coupled to and extending away from the base 2901 and positioned vertically beneath the first support member 2902, a first bracket coupler 2904 of the base 2901, and a projection 2906 of the base 2901. The second support member 2903 may define a second bracket coupler 2905 of that is configured to receive the projection 2906 of the base 2901. This assembly shows the usage of two different types of support members coupled to one base.

Figure 30A:
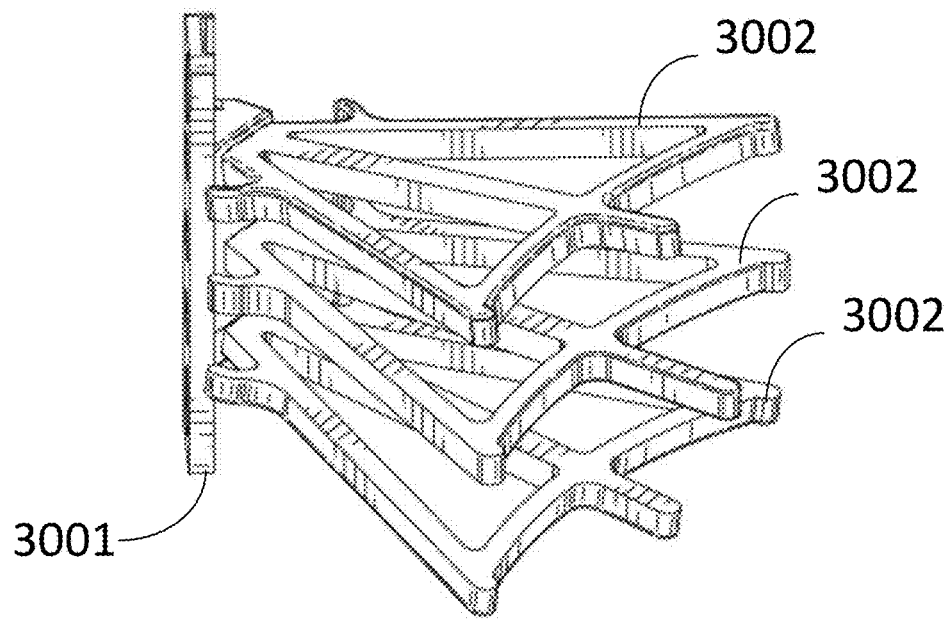
FIGS. 30A and 30B are front (FIG. 30A) and rear (FIG. 30B) perspective views of a bracket, according to yet another example embodiment.
Figure 30B:
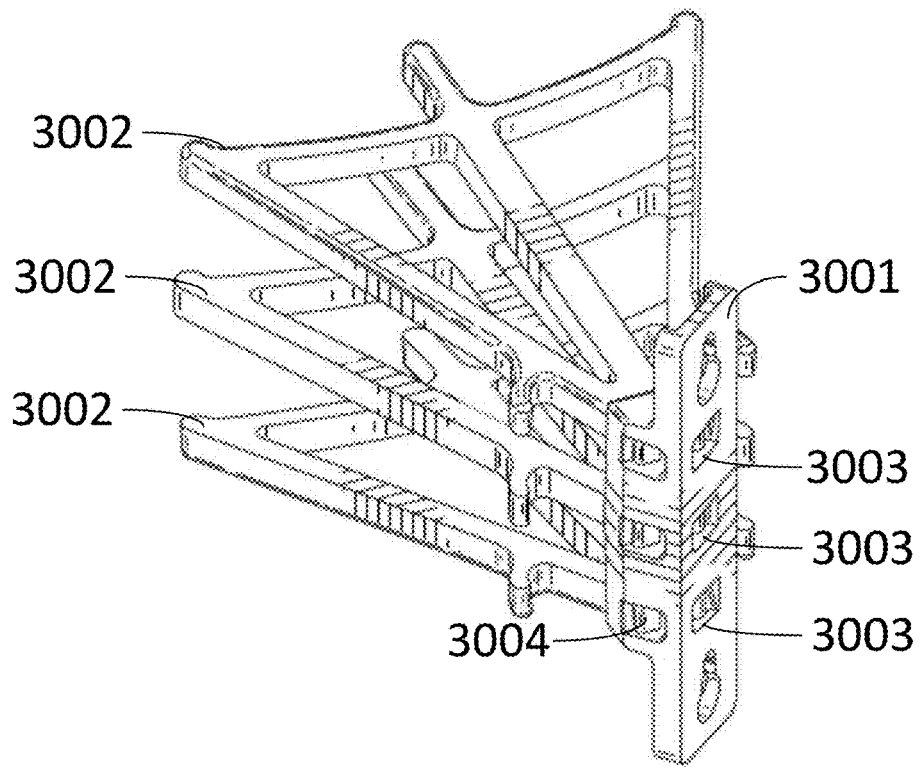

FIGS. 30A-30B show front and rear perspective views of another example bracket assembly that may be used to support a respirator, facemask, other personal protective equipment (PPE), according to an example embodiment. FIGS. 30A-30B show the bracket assembly including a bracket base 3001, a plurality of support members 3002, and a plurality of bracket couplers 3003. The plurality of support members 3002 includes at least one projection 3004 that is configured to be received by the bracket couplers 3003 of the base 3001, which are shown as apertures.

Figure 31:
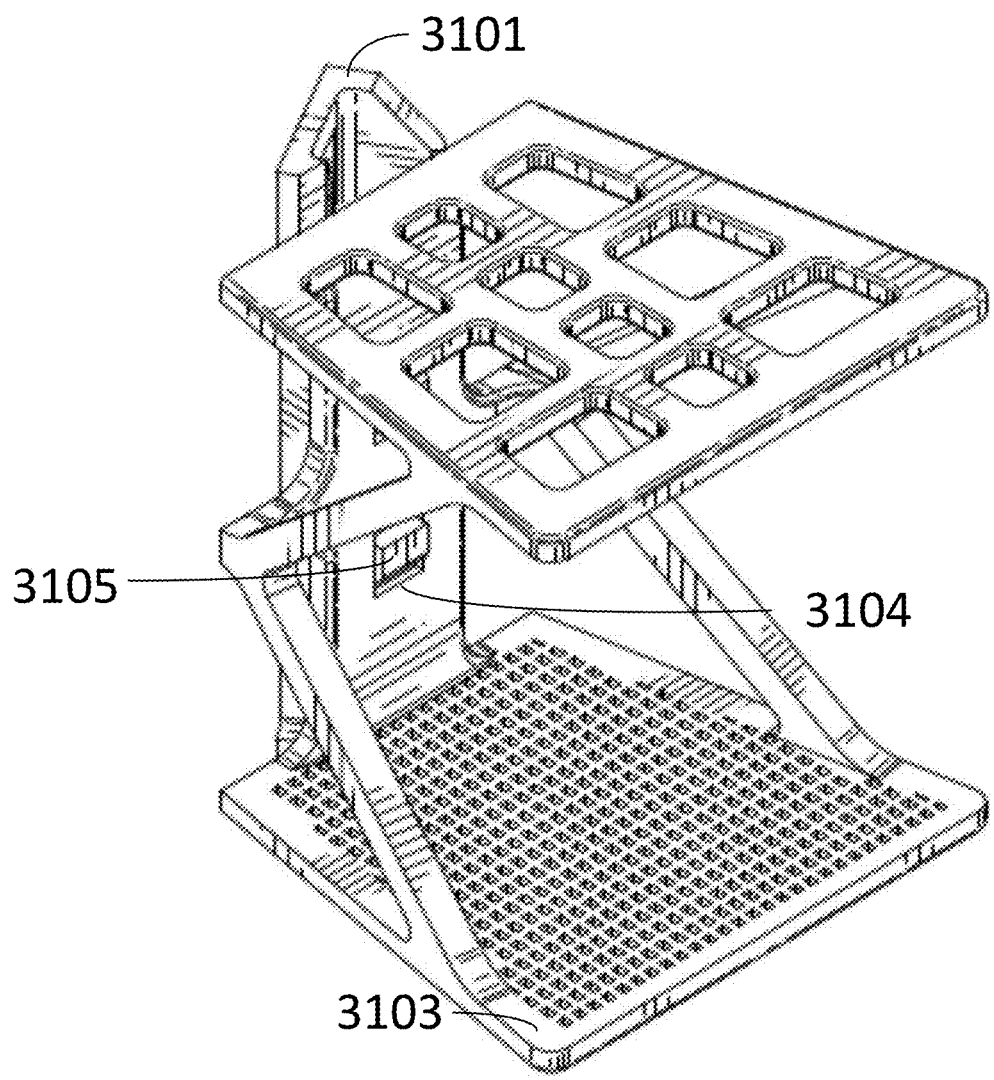
FIG. 31 is a front perspective view of a bracket, according to still another example embodiment.

FIG. 31 shows a front perspective view of another example bracket assembly that may be used to support various miscellaneous items, such as writing instruments (e.g., pens or pencils), electronic devices, bottles, etc. according to an example embodiment. FIG. 31 shows the bracket assembly including a bracket base 3101, a first support members 3102, a second support member 3103, and at least one projection 3105 extending from the base 3101 in substantially a same direction as the first support member 3102 and the second support member 3103. The first support member 3102 and the second support member 3103 can define at least one coupler 3104, shown as an aperture. The coupler 3104 is configured to receive the projection 3105 of the base 3101, according to one embodiment. In the example shown, the first support member 3102 includes a plurality of openings and the second support member 3103 also includes a plurality of openings that are relatively smaller in cross-sectional size than the openings of the first support member 3102.

Figure 32A:
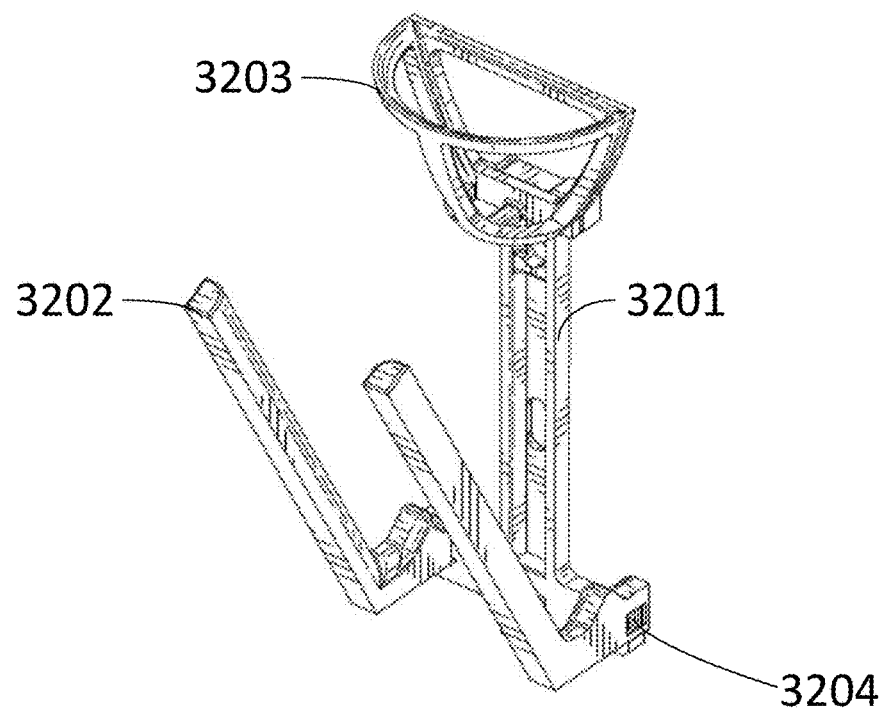
FIGS. 32A and 32B are front (FIG. 32A) and rear (FIG. 32B) perspective views of a bracket, according to a further example embodiment.
Figure 32B:
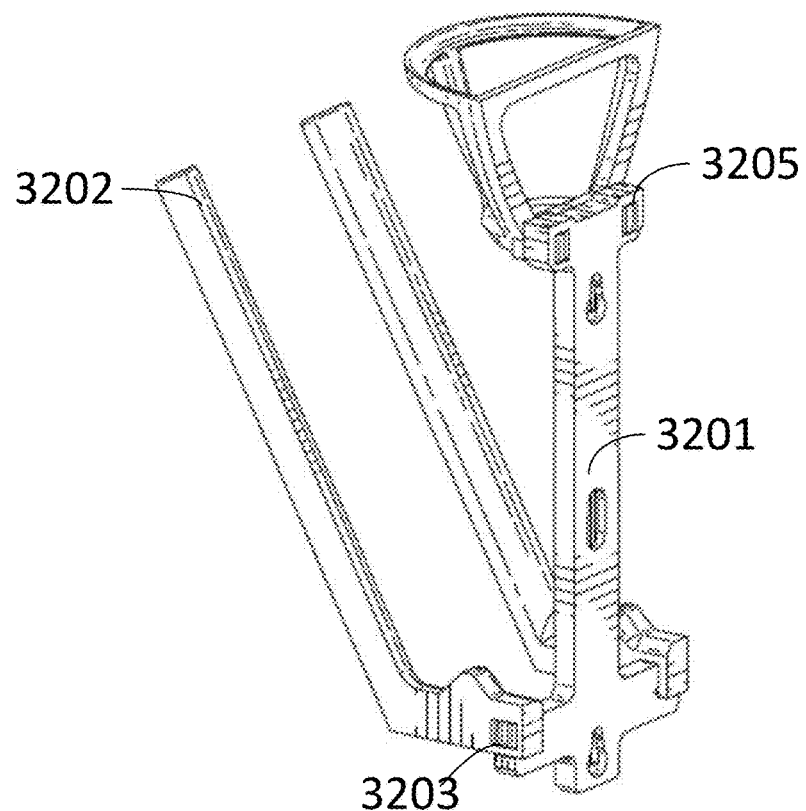

FIGS. 32A-32B show front and rear perspective views of another example bracket assembly member that may be used to support a computer keyboard, computer mouse, or other objects, according to an example embodiment. FIGS. 32A-32B show the bracket assembly including a bracket base 3201, a first support member 3202 coupled to the base 3201, a second support member 3203 coupled to the base 3201 and positioned vertically above the first support member 3202, a first bracket coupler 3204, and a second bracket coupler 3205. The first bracket coupler 3204 is an aperture defined by the first support member 3202 and configured to receive one or more projections extending from the base 3201 to couple the first support member 3202 to the base 3201. The second bracket coupler 3205 is an aperture defined by the base 3201 and configured to receive one or more projections extending from the second support member 3205 to couple the second support member 3205 to the base 3201.

Figure 33A:
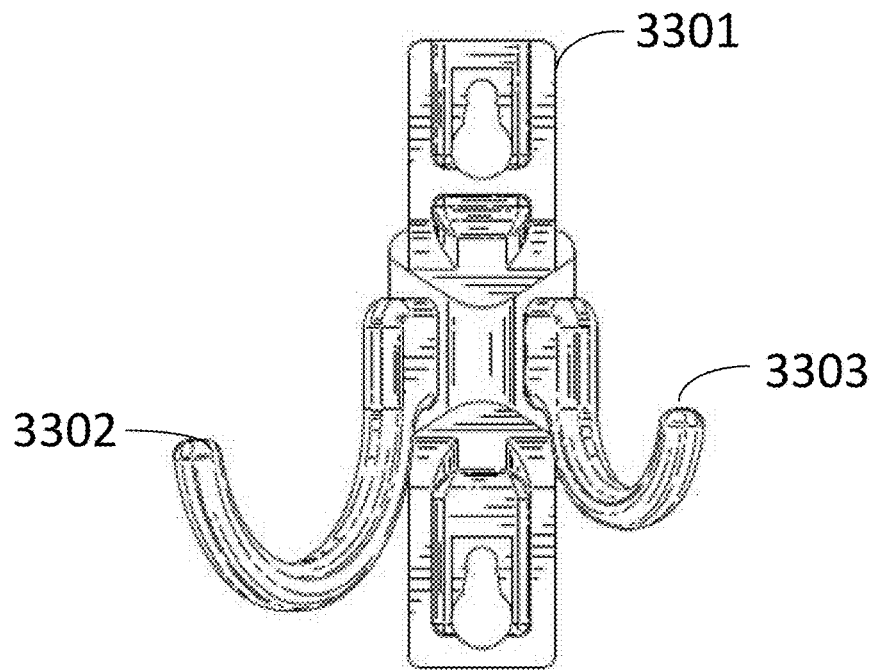
FIGS. 33A and 33B are a front (FIG. 33A) and rear (FIG. 33B) elevation view of a bracket, according to another example embodiment.
Figure 33B:
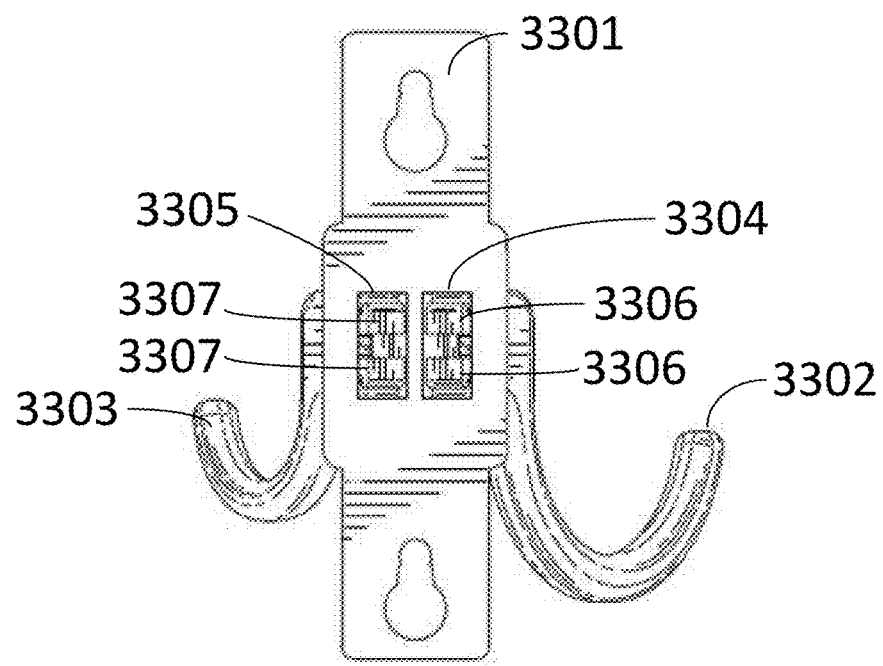

FIGS. 33A-33B show front and rear elevation views of an example bracket assembly that may be used to support hanging items (e.g., a purse, a coat, a ID badge, etc.), according to an example embodiment. FIGS. 33A-33B show the bracket assembly including a bracket base 3301, a first support member 3302 coupled to the base on a left side of the base, a second support member 3303 coupled to the base 3301 on a right side of the base (opposite the first support member), a first bracket coupler 3304 of the base 3301, and a second bracket coupler 3305 of the base 3301. The support members 3302, 3303 may further include projections 3306 and 3307 extending respectively from support members 3302 and 3303 that are received by the bracket couplers to couple the support members to the base 3301. In this example, the base 3301 is structured as the universal bracket base 2000 described herein.

Figure 34A:
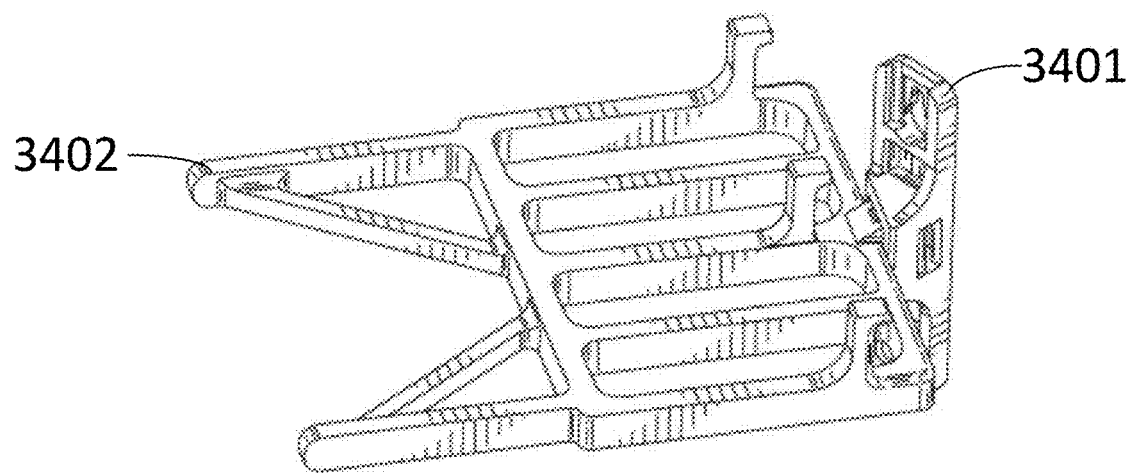
FIGS. 34A and 34B are front (FIG. 34A) and rear (FIG. 34B) perspective views of a bracket, according to still another example embodiment.
Figure 34B:
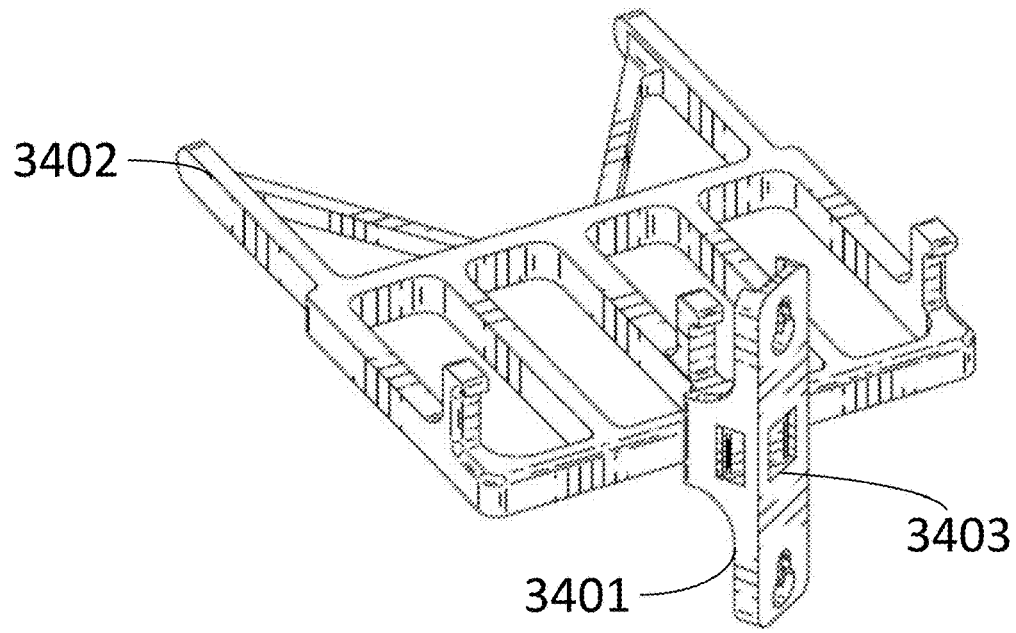

FIGS. 34A-34B show front and rear perspective views of an example bracket assembly that may be used to support goggles (i.e., lab or chemistry goggles) among a variety of other objects, according to an example embodiment. FIGS. 34A-34B show the bracket assembly including a bracket base 3401, a support member 3402 coupled to and extending away from the base 3401, and a bracket coupler 3403 configured as an aperture that receives a projection from the support member 3402 to couple the support member 3402 to the base 3401.

Figure 35A:
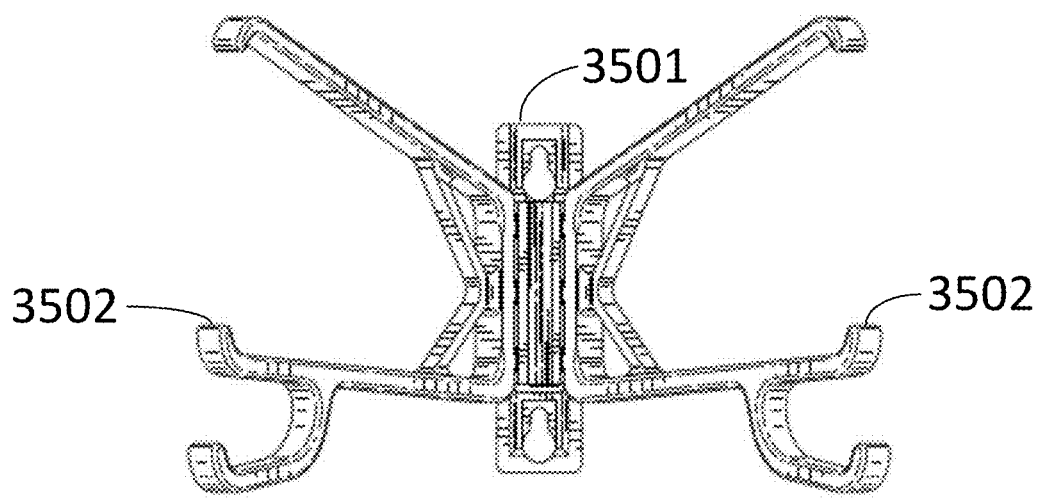
FIGS. 35A and 35B are front (FIG. 35A) and rear (FIG. 35B) elevation views of a bracket, according to another example embodiment.
Figure 35B:
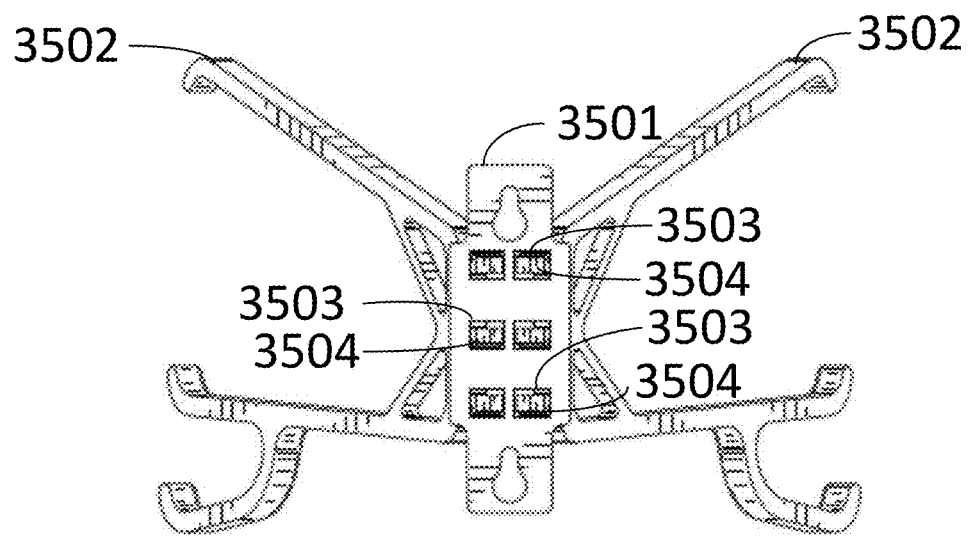

FIGS. 35A-35B show front and rear elevation views of an example bracket assembly that may be used to support one or more items or objects (e.g., gloves, scarves, etc.), according to an example embodiment. FIGS. 35A-35B show the bracket assembly including a bracket base 3501, a plurality of support members 3502 coupled to and extending away from the base 3501, and a plurality of bracket couplers 3503 of the base 3501. The support members 3502 can include one or more projections 3504 extending therefrom and configured to be received by the bracket couplers 3503 (i.e., one projection per coupler/aperture 3503).

Figure 36A:
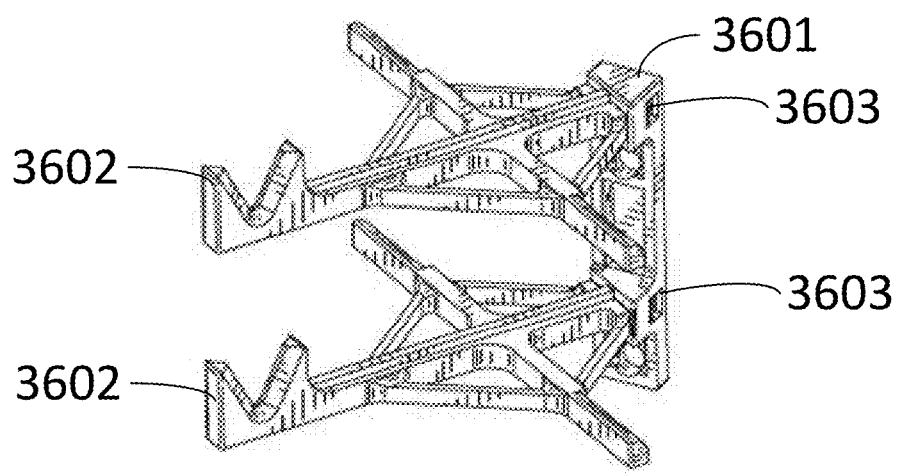
FIGS. 36A and 36B are front (FIG. 36A) and rear (FIG. 36B) perspective views of a bracket, according to still another example embodiment.
Figure 36B:
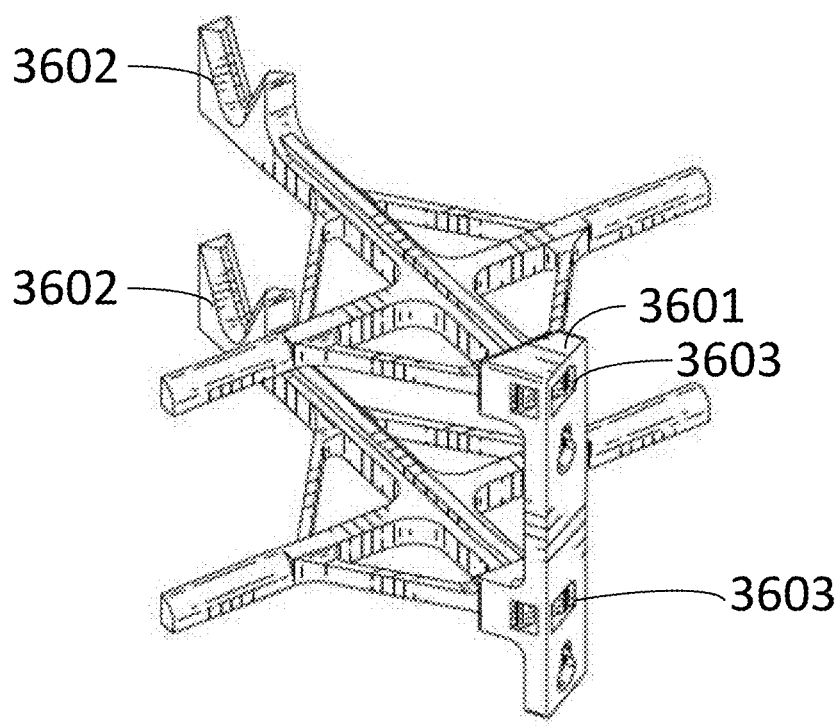

FIGS. 36A-36B show front and rear perspective views of an example bracket assembly that may be used to support eyeglasses, sunglasses, face shields, helmets, etc., according to an example embodiment. FIGS. 36A-36B show the bracket assembly including a bracket base 3601, a plurality of support members 3602 coupled to and extending away from the base 3601, and a plurality of bracket couplers 3603 of the base 3601 that are configured to receive a projection of the support member 3602 to couple the support member to the base 3601.

Figure 37A:
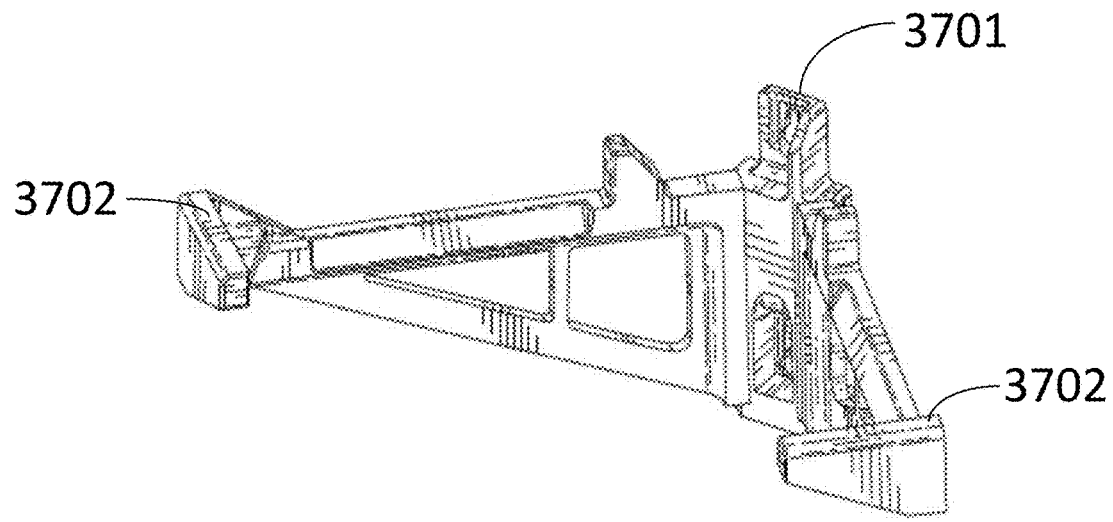
FIGS. 37A and 37B are front (FIG. 37A) and rear (FIG. 37B) perspective views of a bracket, according to yet another example embodiment.
Figure 37B:
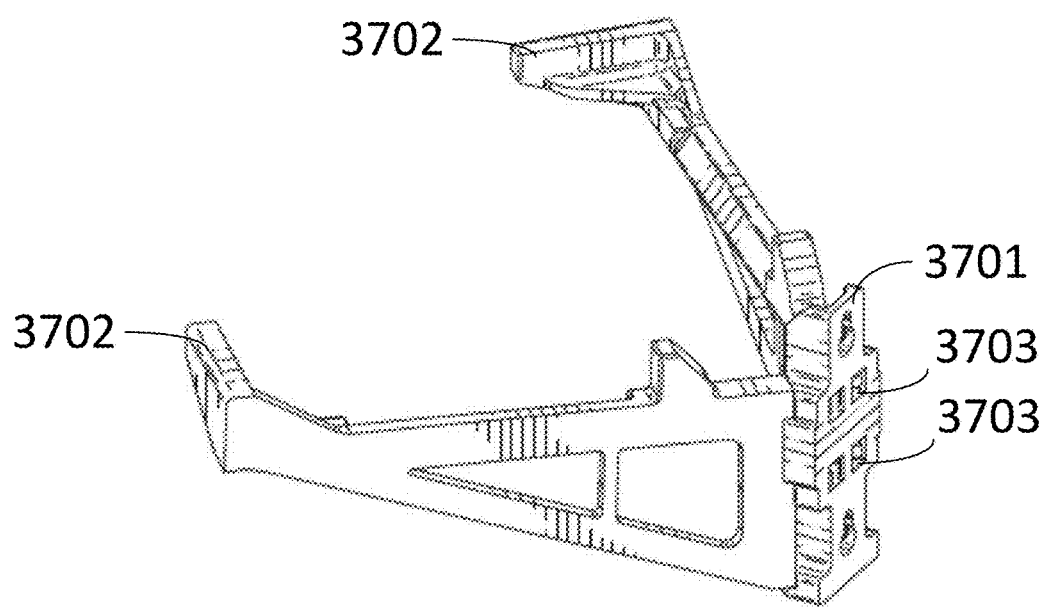

FIGS. 37A-37B show front and rear perspective views of an example bracket assembly that may be used to support sporting equipment (e.g., footballs, basketballs, volleyballs, etc.), according to an example embodiment. FIGS. 37A-37B show a bracket base 3701 (in this example, the base 3701 is structured as the universal base 2000), a plurality of support members 3702 coupled to and extending away from the base 3701, and a plurality of bracket couplers 3703 of the base 3701 that receive projections of the support members 3702 to couple the support members 3702 to the base 3701.

Figure 38:
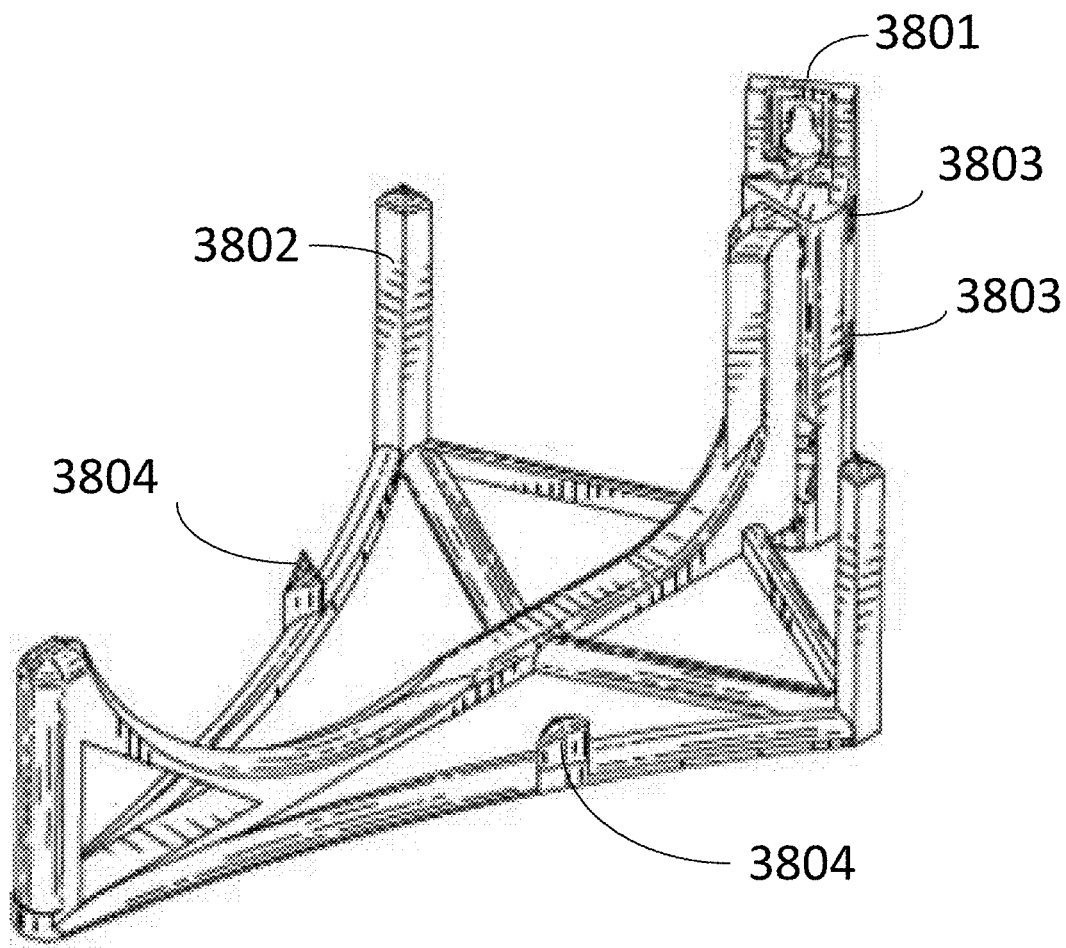
FIG. 38 is a front perspective view of a bracket, according to another example embodiment.

FIG. 38 shows a front perspective view of an example bracket assembly that may be used to support larger objects (e.g., circular objects such as therapy ball, etc.), according to an example embodiment. FIG. 38 shows the bracket assembly including a bracket base 3801, a support member 3802 coupled to and extending away from the base 3801, and a plurality of bracket couplers 3803 (shown as apertures) that receive a projection of the support member 3802 to couple the support member 3802 to the base 3801. The support member 3802 is shown to include a plurality of low-contact touchpoints 3804 that reduce or minimize the contact area between the object and the bracket assembly (particularly, the support member 3802).

Figure 39A:
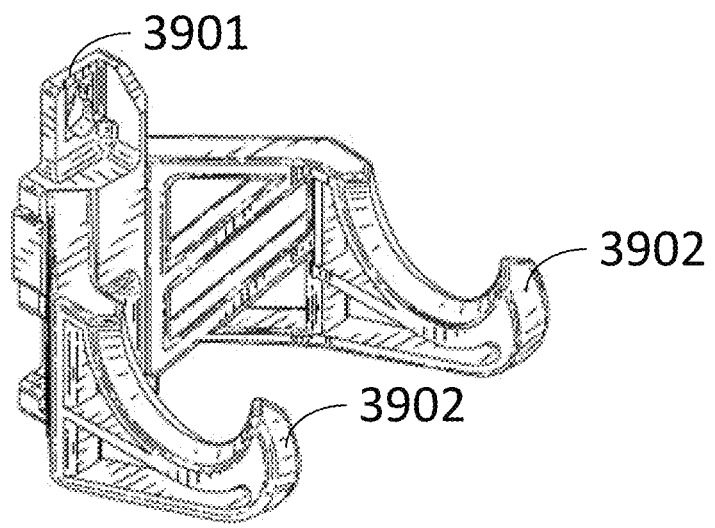
FIGS. 39A and 39B are front (FIG. 39A) and rear (FIG. 39B) perspective views of a bracket, according to still another example embodiment.
Figure 39B:
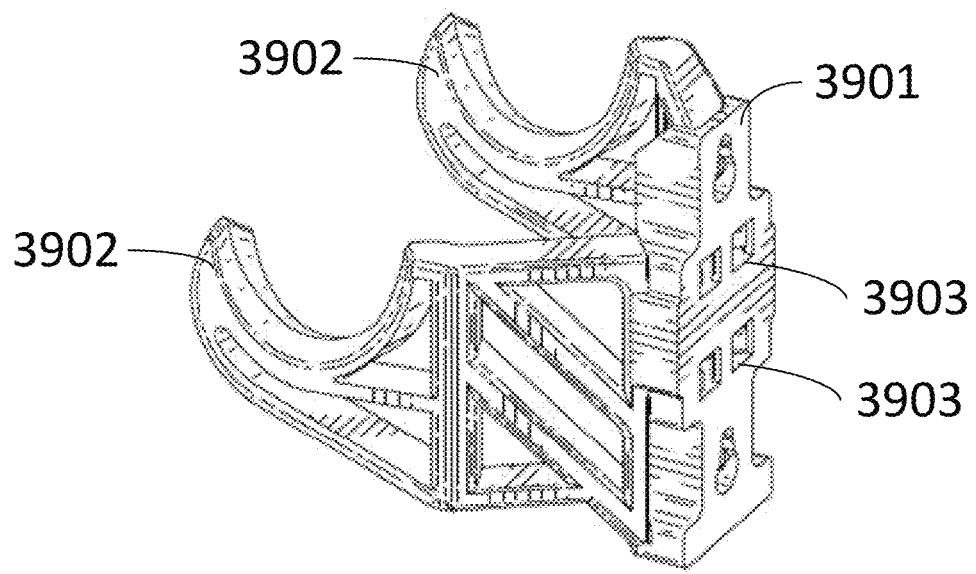

FIGS. 39A-39B show front and rear perspective views of an example bracket assembly that may be used to support various objects (e.g., an umbrella, a dumbbell, etc.), according to an example embodiment. FIGS. 39A-39B show the bracket assembly including a bracket base 3901 (which in this example is structured as the universal base 2000 described herein), a plurality of support members 3902 coupled to the base 3901, and a plurality of bracket couplers 3903 of the base 3901 that couple to the support members 3902 (as described herein with respect to the coupling structure of the universal base to various support members).

Figure 40:
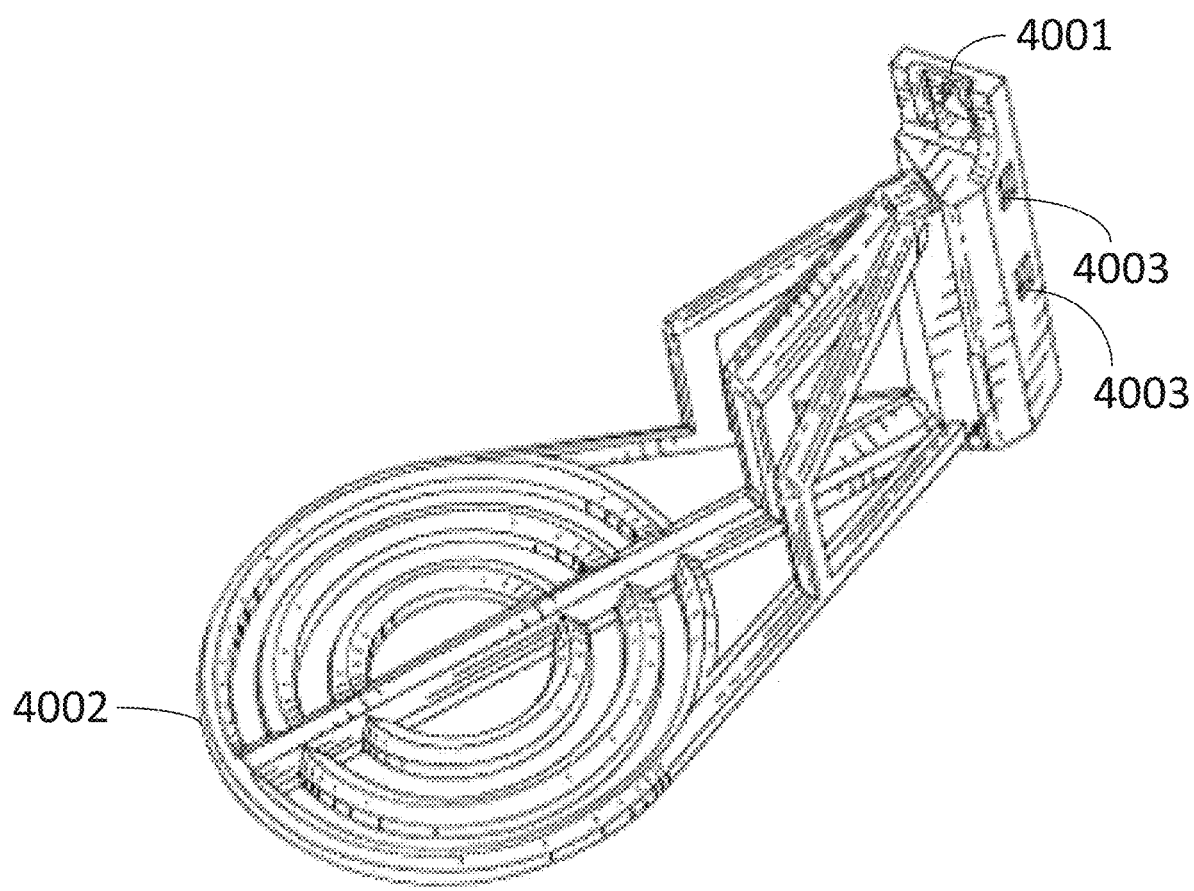
FIG. 40 is a front perspective view of a bracket, according to yet another example embodiment.

FIG. 40 shows a front perspective view of an example bracket assembly that may be used to support a various objects/items (e.g., foam roller, a pot, a pan, etc.), according to an example embodiment. In particular, the bracket assembly of FIG. 40 may be used to support a base of a foam roller used in physical therapy and fitness settings. FIG. 40 shows the bracket assembly including a bracket base 4001, a support member 4002 coupled to and extending away from the base 4001, and a plurality of bracket couplers 4003 of the base 4001 that receive a projection of the support member 4002 to couple to the base 4001.

Figure 41:
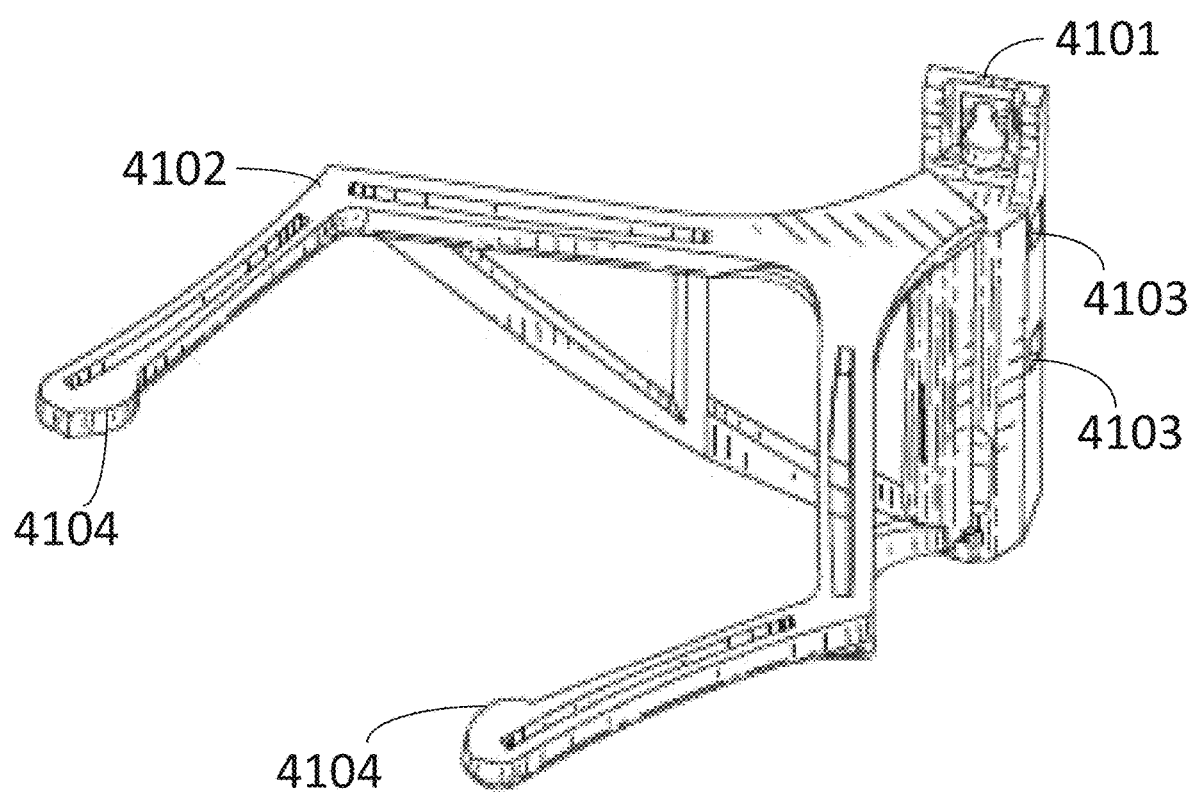
FIG. 41 is a front perspective view of a bracket, according to still yet another example embodiment.

FIG. 41 shows a front perspective view of an example bracket assembly that may be used to support various objects, such as a foam roller, according to an example embodiment. In one embodiment, the bracket assembly of FIG. 41 can be used in combination with the bracket assembly of FIG. 40 to support a foam roller used in physical therapy and fitness settings. More specifically, the bracket assembly of FIG. 41 can be configured to support a cylindrical body of a foam roller. FIG. 41 shows the bracket assembly including a bracket base 4101, a support member 4102 coupled to and extending away from the base 4101, and a plurality of bracket couplers 4103 of the base that receive a projection of the support member 4102 to couple the support member to the base 4101. The support member 4102 may include a plurality of low-contact features or objects 4104, according to an exemplary embodiment. In particular, the low-contact features 4104 can contact a cylindrical body of a foam roller at two points, thereby minimizing contact between the support member 4102 and the foam roller.

Figure 42A:
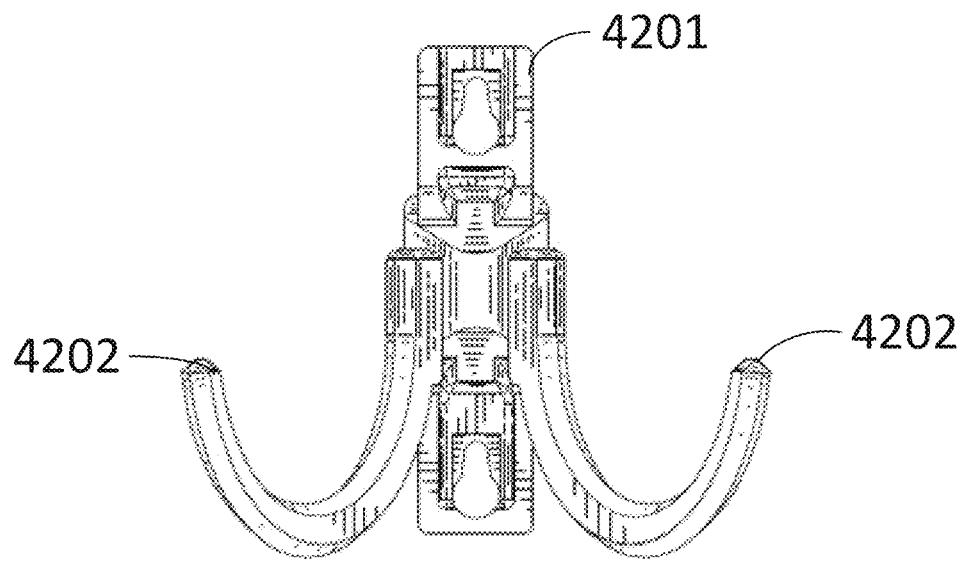
FIGS. 42A and 42B are front (FIG. 42A) and rear (FIG. 42B) elevation views of a bracket, according to yet another example embodiment.
Figure 42B:
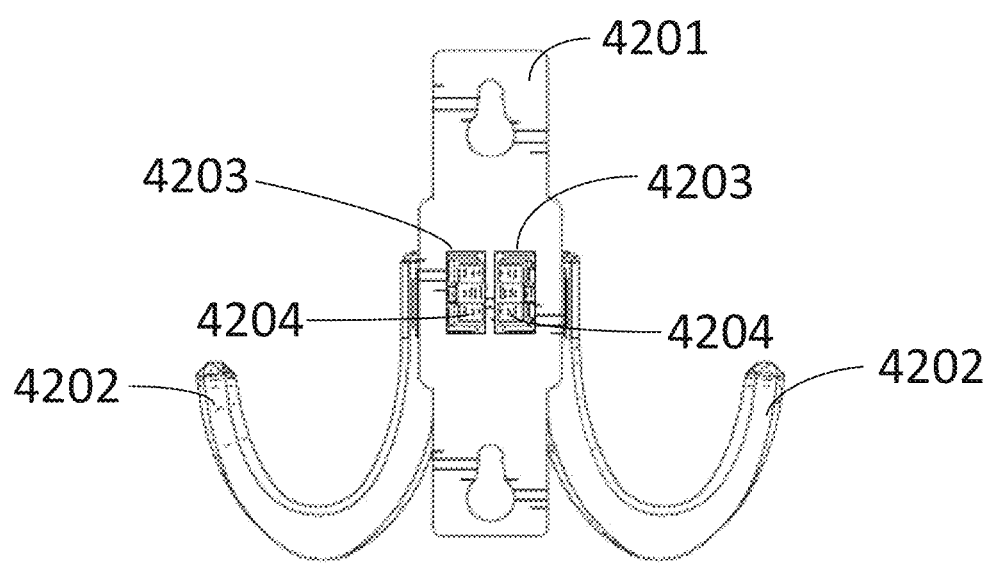

FIGS. 42A-42B show front and rear perspective views of an example bracket assembly that may be used to support various objects/items (e.g., hats, massage devices, etc.), according to an example embodiment. FIGS. 42A-42B show the bracket assembly including a bracket base 4201, a plurality of support members 4202 coupled to and extending away from the base 4201, and a plurality of bracket couplers 4203 of the base that couple the support members 4202 to the base 4201. The support members 4204 can include at least one projection 4204 extending therefrom and configured to be received by the bracket couplers 4203 in order to couple the support member to the base, as described herein.

As shown in each of the bracket couplers (e.g., 2503, 4203), the bracket couplers may be configured to receive at least one projection (e.g., 2804, 3306, 3307, 3505, 4204) of the support member (e.g., 2802, 3602, 3603, 3502, 4202). The at least one projection (e.g., extension, protruding member, extending member, extension etc.) may be coupled to and extend from an end of the support member (e.g., 2802, 3602, 3603, 3502, 4202) and/or be integral with the bracket attachment (i.e., a unitary or solitary component). The at least one projection may extend outward and away from an end of the support member. The at least one projection may include one or more raised portions that project outward and away from at least a portion of the projection. The projection is configured to couple to the bracket base 2000 (or bracket bases 2801, 3601, 3501, 4201, etc.) to couple the support member to the universal bracket base 2000, which is described herein below.

The support member (e.g., 2802, 3602, 3603, 3502, 4202) extends into an interior of the cabinet (e.g., cabinet 1800, 1900). The support member (e.g., 2502, 4202) is configured to support, suspend, or otherwise hold one or more objects within the cabinet. As shown in FIGS. 25A-42B, a variety of support member are depicted that have a variety of different shapes and sizes. The shapes and sizes are used to accommodate a variety of objects (e.g., dumbbells, wires, goggles/eye ware, keyboards, mobile phones, laptop computers, gloves, stethoscopes, etc.). Those of ordinary skill in the art will appreciate the high configurability of the shapes and sizes that may be used to accommodate various objects, even the same type of object (i.e., multiple shapes and sizes may be used to accommodate wire objects).

Many support members (e.g., 2502, 4102) are shown to include low-contact features (e.g., 2504, 3804, 4104). For example, FIGS. 25, 38, and 41 show a support member 2502, 3802, 4102 including a plurality of points 2504, 3804, 4104 extending away from the support member 2502, 3802, 4102. The support members can also include a plurality of ridges. The low-contact features/objects are configured to reduce a surface area contact zone for the object and the respective bracket attachment/support member (and, bracket in general). That way and beneficially, the sterilization and/or disinfection cycle is more likely to impact most of the object/item. It should be understood that a variety of low-contact features may be utilized, such that the points and ridges depicted are not meant to be limiting with other structures having other shapes and sized envisioned.

In some embodiments, the support members of the various bracket assemblies shown in FIGS. 25A-42B can include securing members configured to secure the object to the support member in order to reduce a movement of object with respect to the support member while the object is supported on the bracket assembly. For example, the securing member can include a plurality of sprung metal clips (e.g., alligator clips, electrical clips, and the like) that can clip to (i.e., apply a clamping force to) an object supported by the bracket assembly. The securing members could be directly coupled to the support members in one embodiment (e.g., rotationally coupled via rivets to the support members). In another embodiment, the securing members could be indirectly coupled with the support members. For example, the securing members could be coupled with a tether (e.g., a rope, string, etc.), where tether is coupled to the support member. In various embodiments, the securing member can be configured to substantially ensure the object does not move during a disinfection cycle, particularly when the interior framework of the cabinet is in motion (i.e., a rotating carrousel is rotating) and/or when air is circulated within an interior of the cabinet.

Multiple base configurations/structures are shown in FIGS. 25A-42B with some embodiments showing the universal base 2000. While different base shapes and sizes are shown, the coupling mechanism of the support member to the base is substantially consistent throughout, which is described in more detail below with respect to the universal base 2000.

Based on the foregoing, coupling of the bracket/support member to the universal base 2000 may be described as follows. The apertures 2050 of the universal bracket base 2000 may be configured to receive projections (e.g., 2804, 3306, 3307, 3504, 4204) of a support member/bracket attachment (e.g., 2802, 3602, 3603, 3502, 4202). Each of the aforementioned projections of a bracket attachments may be inserted into a bracket coupler (e.g., 2050, 2803, 3604, 3605, 3503, 4203 that is shown as an aperture/opening) where, in doing so, causes the projection (and any raised portions associated therewith) to flex or move because the size of the aperture 2050 or bracket coupler (cross-sectional size) may be relatively smaller than the cross-sectional size of the projection (and any raised portions associated therewith). Once a substantial portion of the projection is pushed through the aperture 2050 or bracket coupler, the projection (and any raised portions associated therewith may spring, expand, flex, or otherwise move back to a non-flexed position. This causes the raised portions associated with the projection to engage with the universal bracket 2000 (e.g., contact, etc.) in a way that prevents the projection and bracket attachment from being removed from the universal bracket 2000 (i.e., clip into place). To remove the bracket and insert a new bracket to the bracket 2000, a user may move the projection inward to enable that portion to be slid or moved out of the apertures 2050 to disconnect the bracket from the base 2000.

Figures 21, 22:
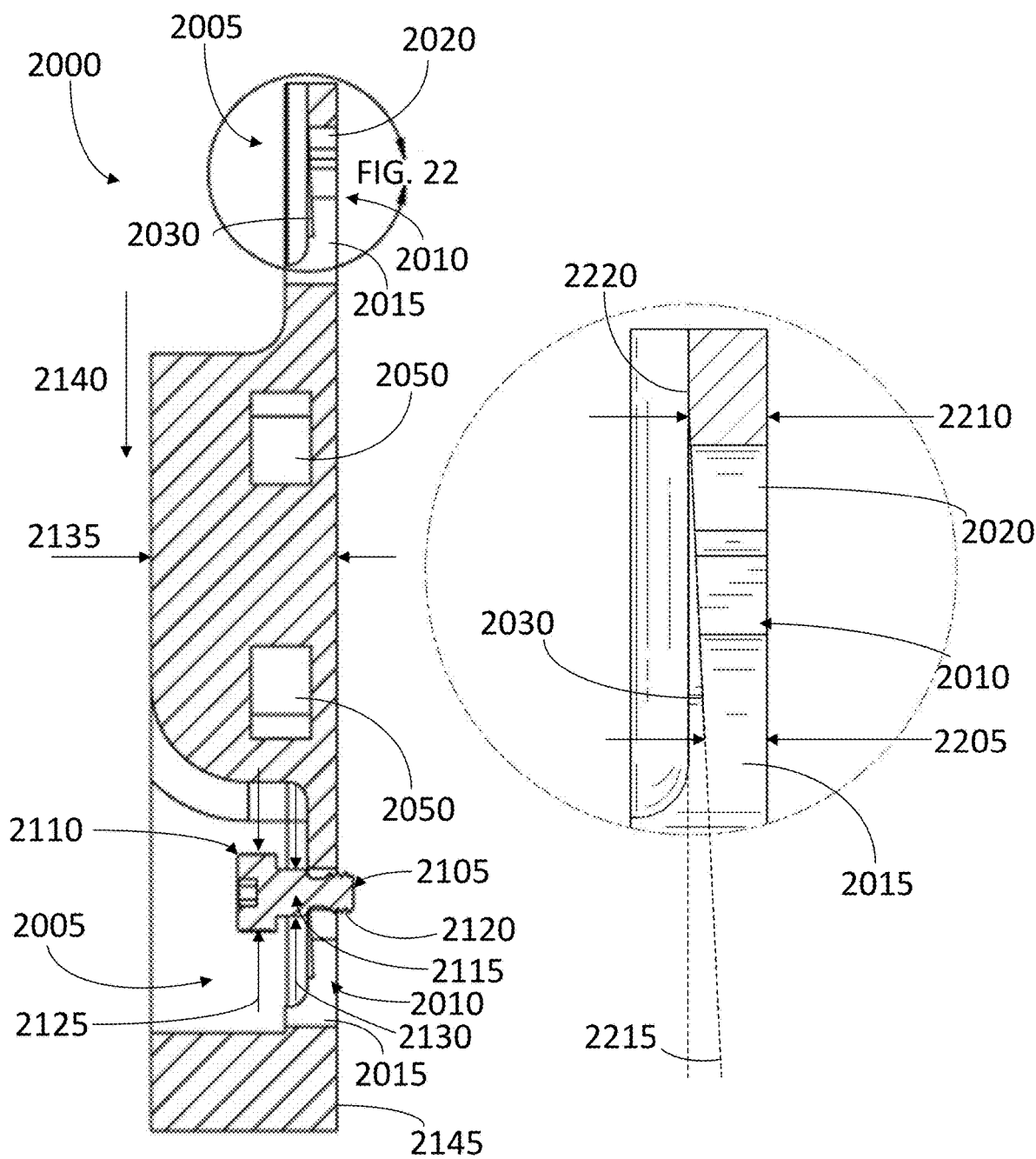
FIG. 21 is a cross-sectional view of the universal bracket base of FIG. 20, according to an example embodiment.
FIG. 22 is a detail view of the coupling structure of the universal bracket base of FIG. 21, according to an example embodiment.

Whether apertures, protrusions, or other coupling means are employed, in one embodiment, the bracket couplers of the base can be angled or offset with respect to a back surface of the universal bracket base 2000 (shown as back surface 2145 of FIG. 21). As a result, the support member can be angled (i.e., offset) with respect to the back surface 2145 of the universal bracket base 2000. As discussed above with reference to FIG. 9, the support members may desirably be offset with respect to the back surface 2145 and the interior framework of the cabinet in order to optimize exposure to vaporized/atomized chemicals, UV light, heated air, etc. during a disinfection and/or sterilization cycle within the cabinet. In some embodiments, both the bracket attachment coupling means and the bracket attachment itself will be oriented such that the object supported by the bracket within the cabinet is "offset" as herein described. In another embodiment, the base 2000 may not include the offset/angle yet the support member itself includes a body portion coupled to the projection to offset the support member (put at an angle) relative to the base 2000. The angling/offset may enable relatively more objects to be included in the cabinet.

In various embodiments, the universal bracket base 2000 and/or the support member can comprise a semi-malleable or ductile material. For example, each of the universal bracket base 2000 and the bracket attachment/support member can be or comprise plastic material. In another embodiment, a portion of the universal bracket base 2000 and/or the bracket attachment/support member can comprise a plastic material, while a remainder of the universal bracket base 2000 and the bracket attachment comprise another material (e.g., a metal material). For example, the coupling structure 2005 of the universal bracket base 2000 and the protruding member of the bracket attachment can comprise a plastic material while the remainder of the universal bracket base 2000 and the bracket attachment comprise some other material.

Referring now to FIG. 21, a cross-sectional view of the base 2000 is depicted, according to an example embodiment. A shown, the base 2000 includes a fastener 2105. The fastener 2105 (e.g., screw, bolt, etc.) can be inserted within the opening 2010 of one or more couplers 2005 of the universal bracket base 2000 described above with respect to FIG. 20. A plurality of fasteners 2105 are coupled to the carrousel structure to facilitate coupling to a plurality of bases 2000. The fastener 2105 can have a head 2110, a shaft 2115, and a threaded portion 2120. The head 2110 has a head diameter 2125. The shaft 2115 can a shaft diameter 2130. According to one embodiment, the head diameter 2125 is less than the first diameter 2035 of the universal bracket base 2000, but larger than the second diameter 2040 of the universal bracket base 2000. The shaft diameter 2130 can be less than both the first diameter 2035 and the second diameter 2040 of the universal bracket base 2000, according to various embodiments. In some embodiments, the shaft diameter 2130 can be greater than the protrusion distance 2045. The threaded portion 2120 can be configured to thread into an aperture of the interior framework of a cabinet, according to one embodiment. In other embodiments, the fastener may be coupled to the interior framework of the cabinet by some other means (e.g., welding, press-fitting, adhesive,) or may be integrally formed with the interior framework of the cabinet.

The universal bracket base 2000 can be installed to the internal cabinet framework by securing the universal bracket base 2000 over one or more fasteners 2105 (e.g., pegs, etc.). With one or more fasteners 2105 coupled with the interior framework (e.g., a rotating carrousel having a plurality of wings extending radially from an axis of rotation, the wings coupled to one or more vertically-oriented shafts, columns, or posts, where the shafts, columns, or posts are configured to couple with a universal bracket base) of the cabinet, the head 2110 of each fastener 2105 may be inserted through the first opening 2015 such that the head 2110 extends beyond surface 2030. In one embodiment, the universal bracket base 2000 can be translated in direction 2140 relative to the fasteners 2105 while the fasteners 2105 remain coupled with the interior framework of the cabinet. As the universal bracket base 2000 is translated, the shaft 2115 of each fastener 2105 passes or extends through the two protrusions 2025 of each coupler 2005. As noted above, the protrusion distance 2045 is less than the shaft diameter 2130. According to an exemplary embodiment, the protrusions 2025 can be configured to deform slightly in order to allow the shaft 2115 of a fastener 2105 to pass between the protrusions 2025. As noted above, each protrusion 2025 may comprise a malleable or ductile material that can deform slightly to allow the shaft 2115 to pass between the protrusions 2025 before substantially returning to its original shape. After the shaft 2115 of each fastener 2105 passes though the protrusions 2025, the shaft 2115 of each fastener 2105 can extend through the second opening 2020 of each respective coupling means 2005. Furthermore, with the shaft 2115 extending through the second opening 2020, the protrusions 2025 of the coupler 2005 are beneath the shaft 2115 and can retain the shaft 2115 within the second opening 2020, according to an exemplary embodiment. In this way, the universal bracket base 2000 is substantially kept from moving relative to the shaft 2115 because the shaft 2115 (and the fastener 2015 more generally) are bounded by the protrusions 2025 and the second opening 2020. When the shaft 2115 is bounded by the protrusions 2025 and the second opening 2020, the universal bracket base 2000 is in an installed position.

As indicated above, the surface 2030 can be a pitched or angled surface, as shown in detail in FIG. 22. According to an exemplary embodiment, the surface 2030 can be pitched or angled such that a wall thickness 2205 of the coupler 2005 at the first opening 2015 is smaller than a wall thickness 2210 of the coupler 2005 at the second opening 2020. The surface 2030 can be pitched at an angle 2215 relative to a flat surface 2220, according to an exemplary embodiment. Moreover, the wall thickness 2215 of the coupler 2005 proximate to the second opening 2020 can be substantially similar to a distance from the head 2110 of a fastener to the interior framework of the cabinet. In this way, as the universal bracket base 2000 is translated in direction 2140 relative to the fasteners 2105 towards the aforementioned installed position, the coupler 2005 tightens against the head 2110 of the fastener 2105. Specifically, when the universal bracket base 2000 is in the installed position (i.e., when the fastener shaft 2115 is within the second opening and has passed between the protrusions 2025), the surface 2030 contacts (e.g., engages) a back surface of the head 2110, further securing the universal bracket base 2000 to the fastener 2105 and interior framework of the cabinet.

Figure 23:
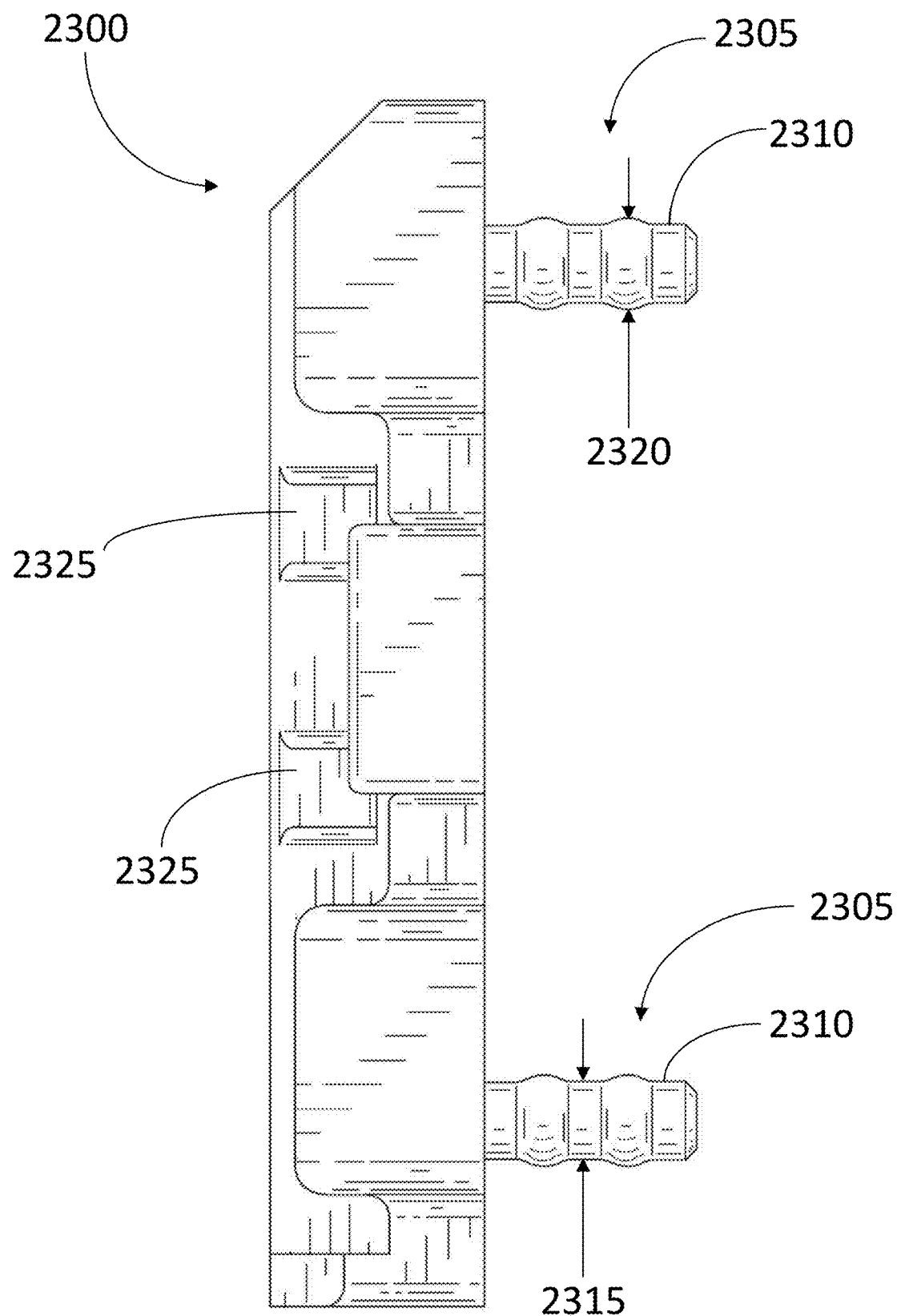
FIG. 23 is a side view of a universal bracket base, according to an example embodiment.

Referring now to FIG. 23, a universal bracket base 2300 is shown, according to another example embodiment. The universal bracket base 2300 can be configured to couple with an interior framework (e.g., rotating carrousel) of a disinfection and sterilization cabinet, as herein described. The universal bracket base 2300 can include one or more coupling structures, couplers, coupling elements, etc. 2305. In contrast to the opening 2010 of the universal bracket base 2000 shown in FIGS. 20-22 and discussed above, the coupling structures 2305 of the universal bracket base 2300 are configured as protruding members 2310. In this example, two protruding members 2310 are included with the base 2300. In other example embodiments, fewer or more than two protruding members 2310 are included with the base 2000. The protruding member 2310 can be configured to be received by one or more apertures of the interior framework of the cabinet, such as an aperture defined by a post or beam of the internal cabinet framework (e.g., the wing frame 1105 as shown in FIG. 11). Each protruding member 2310 can include a minor diameter 2315 that is smaller than a diameter of the aperture of the interior framework. Furthermore, each protruding member 2310 can include a major diameter 2320 that is greater than the diameter of the interior framework. According to an exemplary embodiment, portions of the protruding member 2310 including the major diameter 2320 may slightly deform as the protruding member 2310 is inserted into the aperture of the interior framework. Once inserted into the aperture of the interior framework, the portion of the protruding member 2310 including the major diameter 2320 may substantially return to its original shape (i.e., expand), thereby preventing the protruding member 2310 from being removed from the aperture of the interior framework. According to an exemplary embodiment, a resistance force must be overcome before the portions of the protruding member 2310 having the major diameter 2320 can be deformed to insert the protruding member 2310 into or remove the protruding member 2310 from the aperture of the interior framework.

The universal bracket base 2300 can also include bracket attachment coupling means, shown as apertures 2325. According to an exemplary embodiment the apertures 2325 can be similar to the apertures 2050 shown in FIGS. 20 and 21 and described above. In various embodiments, the protruding members 2310 can be integrally formed with the universal bracket base 2300 such that the universal bracket base 2300 and the protruding members 2310 comprise a single part, according to one embodiment. In another embodiment, the protruding members 2310 can be fastened to or coupled with the universal bracket base 2300.

In another embodiment, the protruding members 2310 of the universal bracket base 2300 can be received clipping members of the interior framework of the cabinet. More specifically, the interior framework can include one or more electrical clips, alligator clips, spring-loaded metal or plastic clip with serrated jaws, or other clip device that is configured to apply a clamping force to an object placed within a pair of clip jaws. Serrated teeth of clip jaws may apply a clamping force to one or more of the protruding members 2310 of the universal bracket base 2300, according to one embodiment. In another embodiment, a universal bracket base (e.g., universal bracket base 2000) can have a clipping device (e.g., alligator clip, sprung metal clip with serrated jaws, etc.) as coupling members that are configured to clip to shafts, protrusions, protruding members, pins, etc. of the interior framework of the cabinet.

Figure 24:
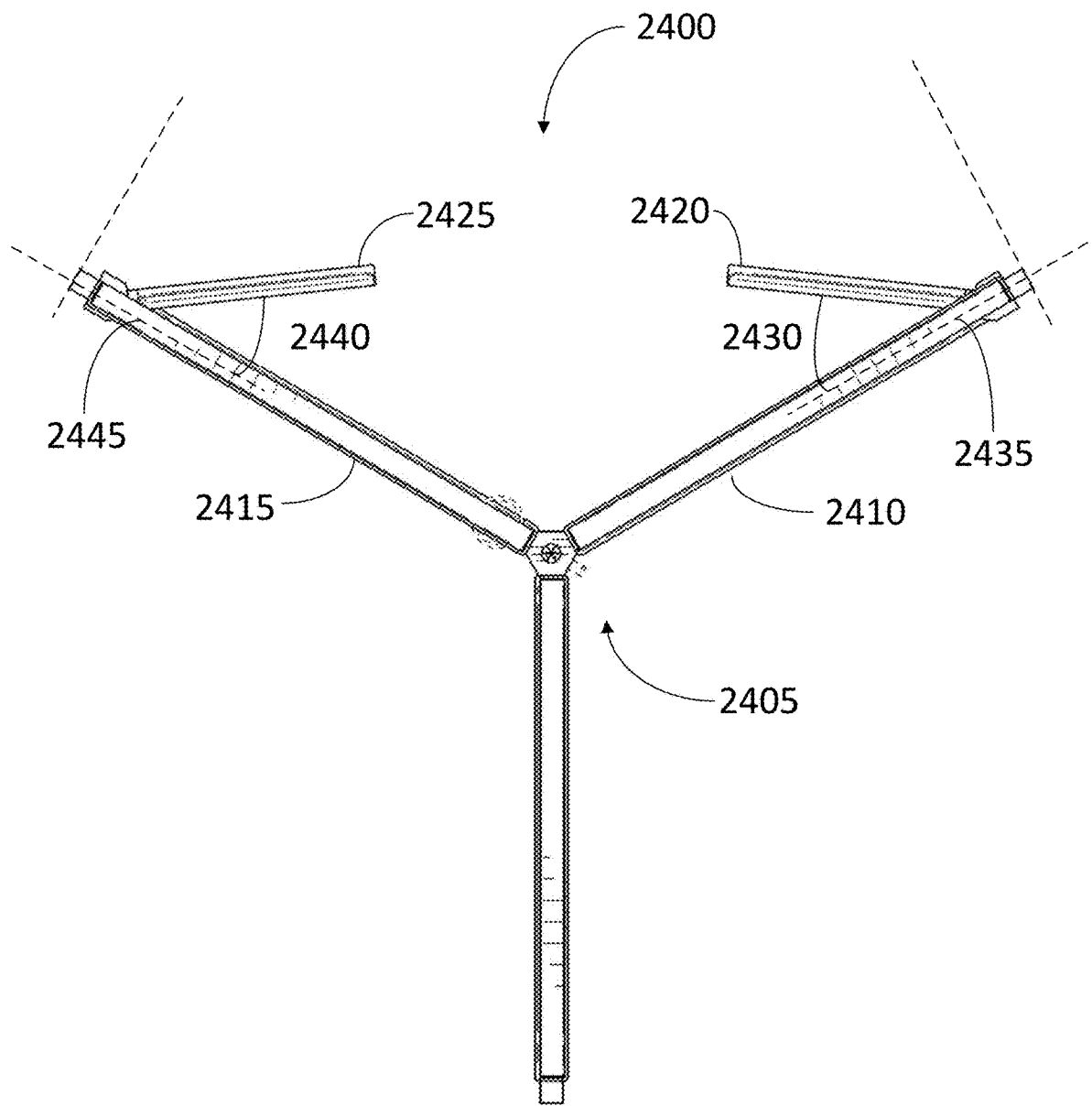
FIG. 24 is a top view of an interior framework of a cabinet, according to an example embodiment.

Referring now to FIG. 24, an interior framework 2400 of a disinfection or sterilization cabinet is shown, according to an exemplary embodiment. The interior framework 2400 can include a carrousel 2405 that can be configured to rotate about a central axis, according to an exemplary embodiment. As described above with reference to FIG. 11 and others, the carrousel may be driven via a drive-clutch that allows the carrousel to rotate in one direction with and allows for appropriate safety slippage in the event the carrousel 2405 crashes into an object within the cabinet. The drive-clutch may be communicably coupled to the display device (e.g., display device 1840 or 1940) such that a user may control the rotation of the carrousel 2405 via the display device. The rotating carrousel 2405 can include a plurality of wings, such as wings 2410 and 2415. In an exemplary embodiment, the rotating carrousel 2405 can include three wings. As described above, a bracket may be coupled the interior framework, namely to posts or beams positioned proximate to a distal end of each wing (e.g., to wing frames 1105 as shown in FIG. 11). More specifically, the one or more brackets may be coupled to the interior framework of the cabinet such that the bracket is "offset" from the frame, as discussed in detail above with reference to FIGS. 9 and 20. In some embodiments, the object to be disinfected or sterilized is too large, heavy, or bulky to be supported by a single bracket or by multiple brackets coupled along a single wing of the carrousel. Accordingly, circumstances may arise where it may be desirable to support an object (e.g., a lead vest) using a plurality of brackets coupled with the interior framework of the cabinet via multiple wings.

More specifically, and as shown in FIG. 24, a first bracket or bracket assembly 2420 can be coupled to the first wing 2410 of the carrousel 2405, while a second bracket or bracket assembly 2425 can be coupled to the second wing 2415 of the carrousel 2405. Rather than each bracket or bracket assembly 2420, 2425 being offset in the same direction (i.e., clockwise or counterclockwise) relative to wings 2410, 2415, respectively, bracket assemblies 2420 and 2425 are offset in opposite directions. In particular, the first bracket or bracket assembly 2420 is offset relative to wing 2410 in a first direction, while the second bracket or bracket assembly 2425 is offset from wing 2415 in a second direction. According to one embodiment, the two bracket assemblies 2420, 2425 can be offset in a direction facing the other bracket assembly 2425, 2520. The first bracket 2420 can be offset at a first angle 2430 from a wing centerline 2445. The second bracket 2425 can be offset from at a second angle 2440 from a second wing centerline 2445. According to an exemplary embodiment, the first angle 2430 and the second angle 2440 may be substantially similar (albeit in different directions).

Although substantially similar offset angles of multiple brackets can be used prevent one supported object from obscuring or occluding another supported object from exposure to vaporized/atomized chemicals, UV light, heated air, etc. during a sterilization or disinfection cycle as noted above with reference to FIG. 9, the example of FIG. 24 represents an instance where differing offset angles of various brackets may be necessary. When large, heavy, or bulky objects are supported within the cabinets as shown in FIG. 24, it may also be necessary to remove the center shaft (e.g., center shaft 1103 shown in FIG. 11) of the carrousel 2405 to bolster exposure to vaporized/atomized chemicals, UV light, heated air, etc.

One embodiment provides a new and improved item disinfection system and method which provides the operator with an operator viewing window that is safety glass and UV-C resistant thereby allowing the operator to observe the interior of the cabinet at all times.

One embodiment provides a new and improved item disinfection system and method which provides the operator with an operator screen that allows the selection of cycle modes, settings, timings, as well as system status communication methods whereby the operator can see the current status, error messages, instructions and more.

One embodiment provides a new and improved item disinfection system and method which has lights and indicators on both operating sides of the cabinet whereby the lights and screens communicate the machine status (e.g. "Dirty/Ready for Loading", "In-Use", "Clean/Ready for Unloading", etc.) using colors and words to easily convey to the operator a status.

One embodiment provides a new and improved item disinfection system and method which features a full system test cycle upon powering up the cabinet. A test cycle tests all disinfection subsystems and sensors for proper working order and asks the operator to confirm a success. This test cycle provides confidence that all subsequent activity is being performed properly.

One embodiment provides a new and improved item disinfection system and method which includes dynamic control software that contains actions and decisions using sensor inputs to perform the selected disinfection treatment cycle.

One embodiment provides a new and improved item disinfection system and method which has a smooth exterior surface on all sides with no exposed wires or cords or protruding parts that could be caught during operation or transportation of the cabinet.

One embodiment provides a new and improved item disinfection system and method which requires only a single 120v 15a power connection to accomplish all operations and is easily powered by external power generators or a battery pack.

One embodiment provides a new and improved item disinfection system and method which enables matching the disinfection treatment plan to the items (and their materials) requiring disinfection. A disinfection treatment plan is based upon [contaminant×materials×disinfection method×duration]. The ability to include (or exclude) a disinfection method based upon a material match (or conflict) is part of this embodiment.

One embodiment provides a new and improved item disinfection system and method which provides operating software controls that assure a disciplined/metered treatment efficacy for the varied items and materials and contaminants requiring disinfection, operate and communicate system and cycle status.

One embodiment provides a new and improved item disinfection system and method which can be self-operated by the institution, requiring no 3rd party expense or dependency.

One embodiment provides a new and improved item disinfection system and method which is a "closed system" whereby no air or vapor may be evacuated outside the enclosure for any purpose during or following the operation of the cabinet. The system is self-contained and inert at the end of any cycle whereby the enclosure, items, contaminants, and disinfection materials used in the treatment cycle do not affect the cabinet's operator or item's user or the cabinet's operating environment whereby additional precautions may be taken post-treatment or post-cycle.

One embodiment provides a new and improved item disinfection system and method which provides multiple disinfection methods and item manipulation whereby the cabinet maintains a sound level of 85 decibels or less and cannot be detected from outside a sealed operating area.

One embodiment provides a new and improved item disinfection system and method which allows the operator to place and remove items within the cabinet without having to step into the enclosure or reach or bend or stoop in a manner that causes physical strain or long-term fatigue or injury. A further object is to allow 100% access to the entire enclosure from any door whereby there are no physical panels or barriers between any portion of the interior workspace and the outside when the door is opened (this means the doors can be 100% of the side of the enclosure).

One embodiment provides a new and improved item disinfection system and method which allows an item to fall from its original mounted position inside the enclosure to the bottom of the enclosure whereby the system can continue to operate without damaging the item else the system will stop operating. A further object is to have no moving parts, technology, or any component at the bottom of the enclosure whereby items or fluids could interfere with a disinfection cycle or damage the enclosure or its components.

One embodiment provides a new and improved item disinfection system and method which is susceptible to a low cost of manufacture with regard to both materials and labor, and which accordingly is then susceptible to low prices of sale to the consuming industry, thereby making such cabinet economically available to those in the industry.

One embodiment provides a new and improved item disinfection system and method which provides all of the advantages of the prior art, while simultaneously overcoming some of the disadvantages normally associated therewith.

CONCLUSION

Although the subject matter has been described in terms of certain embodiments, other embodiments that may or may not provide various features and aspects set forth herein shall be understood to be contemplated by this disclosure. The specific embodiments described above are disclosed as examples only, and the scope of the patented subject matter is defined by the claims that follow. In the claims, the terms "based upon" and "based on" shall include situations in which a factor is taken into account directly and/or indirectly, and possibly in conjunction with other factors, in producing a result or effect. In the claims, a portion shall include greater than none and up to the whole of a thing.

Although this description may discuss a specific order of method steps, the order of the steps may differ from what is outlined. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

It is important to note that the construction and arrangement of the electromechanical variable transmission as shown in the exemplary embodiments is illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claims.

What is claimed is:

1. A disinfection or sterilization cabinet, comprising:
  a cabinet frame defining an interior cabinet space;
  at least one door coupled to the cabinet frame, the at least one door movable between a first position that substantially prevents access to the interior cabinet space and a second position spaced apart from the cabinet frame that enables access to the interior cabinet space;
  an internal cabinet framework coupled to the cabinet frame and disposed within the interior cabinet space, the internal cabinet framework comprising at least one bracket coupling structure;
  at least one bracket removably coupled to the internal cabinet framework via the at least one bracket coupling structure, the at least one bracket including a support member detachably coupled with a bracket base, the bracket base defining a back surface and an opening extending at least partially toward the back surface, the back surface positioned proximate the bracket coupling structure of the interior cabinet framework with the bracket coupled to the internal cabinet framework, the support member including a projection, the opening to receive the projection of the support member to position the support member at an angle relative to the back surface of the bracket base, wherein the support member includes a low contact object configured to reduce a contact area of an object supported by the at least one bracket; and
  at least one disinfectant or sterilization element configured to at least partially disinfect or sterilize the object supported by the at least one bracket.

2. The disinfection or sterilization cabinet of claim 1, wherein the bracket coupling structure includes a fastener coupled with and extending from the internal cabinet framework, wherein the at least one bracket defines a second opening configured to receive the fastener.

3. The disinfection or sterilization cabinet of claim 2, the at least one bracket further comprising a protrusion extending into the second opening, wherein the second opening comprises a first portion having a first diameter, a second portion having a second diameter, and a protrusion distance, wherein the protrusion is positioned between first portion and the second portion.

4. The disinfection or sterilization cabinet of claim 3, the fastener further comprising a head having a head diameter and a shank having a shank diameter, wherein the head diameter is less than the first diameter but greater than the second diameter, wherein the shank diameter is less than the second diameter but greater than the protrusion distance.

5. The disinfection or sterilization cabinet of claim 4, wherein the protrusion comprises a malleable material that is configured to deform as the fastener is received by the second opening and is moved from the first portion to the second portion past the protrusion.

6. The disinfection or sterilization cabinet of claim 1, wherein the bracket coupling structure comprises an aperture, wherein the at least one bracket comprises a protrusion configured to be received by the aperture.

7. The disinfection or sterilization cabinet of claim 6, wherein the protrusion comprises a projection extending away from the protrusion, the projection configured to move to couple the bracket to the internal cabinet framework.

8. The disinfection or sterilization cabinet of claim 1, wherein the cabinet frame includes support structures that define a duct, the duct configured to direct air towards the interior cabinet space.

9. The disinfection or sterilization cabinet of claim 1, wherein the internal cabinet framework comprises a carrousel comprising a shaft, the carrousel configured to rotate about an axis, the shaft spaced apart from the axis wherein the shaft comprises the bracket coupling structure.

10. The disinfection or sterilization cabinet of claim 9, wherein the opening of the bracket base is oriented at an oblique angle relative to the back surface of the bracket base such that the support member is positioned at an oblique angle relative to the back surface of the bracket base, the support member extending at least partially toward the axis when coupled with the bracket coupling structure.

* * * * *